United States Patent
Gretzke et al.

(10) Patent No.: US 7,148,246 B2
(45) Date of Patent: Dec. 12, 2006

(54) CYCLOALKYL DERIVATIVES HAVING BIOISOSTERIC CARBOXYLIC ACID GROUPS, PROCESSES FOR THEIR PREPARATION AND THEIR USE AS PHARMACEUTICALS

(75) Inventors: Dirk Gretzke, Frankfurt (DE); Heiner Glombik, Hofheim (DE); Eugen Falk, Frankfurt (DE); Jochen Goerlitzer, Frankfurt am Main (DE); Stefanie Keil, Hofheim (DE); Hans-Ludwig Schaefer, Hochheim (DE); Christian Stapper, Mainz (DE); Wolfgang Wendler, Selters (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 10/789,865

(22) Filed: Feb. 27, 2004

(65) Prior Publication Data

US 2004/0198786 A1   Oct. 7, 2004

Related U.S. Application Data

(60) Provisional application No. 60/487,432, filed on Jul. 15, 2003.

(30) Foreign Application Priority Data

Feb. 27, 2003  (DE) ................. 103 08 354

(51) Int. Cl.
C07D 277/04 (2006.01)
C07D 209/54 (2006.01)
C07D 257/04 (2006.01)
C07D 413/00 (2006.01)
A61K 31/42 (2006.01)

(52) U.S. Cl. .................. 514/374; 548/146; 548/215; 548/250; 548/408

(58) Field of Classification Search ............. 548/215, 548/146, 250, 408; 514/374
See application file for complete search history.

(56) References Cited

U.S. PATENT DOCUMENTS

| | | | | |
|---|---|---|---|---|
| 5,468,762 A | * | 11/1995 | Malamas et al. | ........... 514/376 |
| 5,532,256 A | * | 7/1996 | Malamas et al. | ........... 514/361 |
| 6,221,633 B1 | | 4/2001 | Ertl et al. | |
| 6,221,897 B1 | | 4/2001 | Frick et al. | |
| 6,245,744 B1 | | 6/2001 | Frick et al. | |
| 6,277,831 B1 | | 8/2001 | Frick et al. | |
| 6,342,512 B1 | | 1/2002 | Kirsch et al. | |
| 6,710,063 B1 | | 3/2004 | Choa et al. | |
| 6,723,740 B1 | | 4/2004 | Choa et al. | |

FOREIGN PATENT DOCUMENTS

EP    0 462 884 A1    12/2001

| | | |
|---|---|---|
| WO | WO 94/18183 | 8/1994 |
| WO | WO 94/18184 | 8/1994 |
| WO | WO 96/38428 | 12/1996 |
| WO | WO 97/26265 | 7/1997 |
| WO | WO 97/41097 | 11/1997 |
| WO | WO 98/08871 | 3/1998 |
| WO | WO 98/19998 | 5/1998 |
| WO | WO 99/03861 | 1/1999 |
| WO | WO 99/15525 | 4/1999 |
| WO | WO 99/61431 | 12/1999 |
| WO | WO 99/62871 | 12/1999 |
| WO | WO 99/62872 | 12/1999 |
| WO | WO 99/67278 | 12/1999 |
| WO | WO 99/67279 | 12/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 A1 | 12/2000 |
| WO | WO 01/04146 A2 | 1/2001 |
| WO | WO 01/09111 A1 | 2/2001 |
| WO | WO 01/21602 A1 | 3/2001 |
| WO | WO 01/40169 A1 | 6/2001 |
| WO | WO 01/40171 A1 | 6/2001 |
| WO | WO 01/72290 A2 | 10/2001 |

(Continued)

OTHER PUBLICATIONS

Malamas et al., "New Azolidinediones as Inhibitors of Protein Tyrosine Phosphatase 1B with Antihyperglycemic Properties," Sep. 17, 1999, J. Med. Chem., vol. 43, pp. 995-1010.*

(Continued)

*Primary Examiner*—Kamal A. Saeed
*Assistant Examiner*—Susannah L. Chung
(74) *Attorney, Agent, or Firm*—Barbara E. Kurys

(57) ABSTRACT

Cycloalkyl derivatives having bioisosteric carboxylic acid groups, processes for their preparation and their use as pharmaceuticals The invention relates to cycloalkyl derivatives having bioisosteric carboxylic acid groups and to their physiologically acceptable salts and physiologically functional derivatives.

What is described are compounds of the formula I,

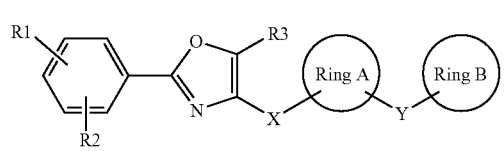

in which the radicals are as defined, and their physiologically acceptable salts and processes for their preparations. The compounds are suitable for the treatment and/or prevention of disorders of fatty acid metabolism and glucose utilization disorders as well as of disorders in which insulin resistence is involved.

13 Claims, No Drawings

FOREIGN PATENT DOCUMENTS

| | | |
|---|---|---|
| WO | WO 01/81327 A1 | 11/2001 |
| WO | WO 01/83451 | 11/2001 |
| WO | WO 01/85695 A1 | 11/2001 |
| WO | WO 01/91752 A1 | 12/2001 |
| WO | WO 01/94300 | 12/2001 |
| WO | WO 02/38541 A1 | 5/2002 |
| WO | WO 02/46146 A1 | 6/2002 |
| WO | WO 02/50027 | 6/2002 |
| WO | WO 02/051820 | 7/2002 |
| WO | WO 02/064549 A1 | 8/2002 |
| WO | WO 02/096864 | 12/2002 |
| WO | WO 03/004458 A1 | 1/2003 |
| WO | WO 03/020269 | 3/2003 |
| WO | WO 03/040174 A2 | 5/2003 |
| WO | WO 03/066581 A1 | 8/2003 |
| WO | WO 03/084922 | 10/2003 |
| WO | WO 03/084923 | 10/2003 |
| WO | WO 03/104188 | 12/2003 |

OTHER PUBLICATIONS

Momose et al., "Novel 5-Substituted 1,4-Thiazolidinedione and 2,4-Oxazolidinedione Derivatives as Insulin Sensitizers with Antidiabetic Activities," Oct. 22, 2001, J. Med. Chem., vol. 45, p. 1518-1534.*

Malamas et al., titled "New Azolidinediones as Inhibitors of Protein Tyrosine Phophatase 1B with Antihyperglycemic Properties," J. Med. Chem., vol. 43 (2000), pp. 995-1010, especially p. 996, Compound 15.*

Asakawa, A., et. al., Cocaine-Amphetamine-Regulated Transcript Influences Energy Metabolism Anxiety and Gastric Emptying in Mice, Hormone and Metabolic Research; vol. 33(9); 2001; pp. 554-558.

Berger, J., et. al., The Mechanisms of Action of PPARs, Annul. Rev. Med.; vol. 53; 2002; pp. 409-435.

Fruchart, J.C., et. al., PPARs, Metabolic Disease and Atherosclerosis, Pharmacological Research; vol. 44, No. 5; 2001' pp. 345-352.

Kersten, S., et. al., Roles of PPARs in Health and Disease, Nature; vol. 405; May 25, 2000; pp. 421-424.

Kliewer, S.A., et. al., Peroxisome Proliferator-Activated Receptors: From Genes to Physiology, Recent Prog. Horm Res.; vol. 56; 2001; pp. 239-263.

Lee, D.W., et. al., Leptin agonists as a potential approach to the treatment of obesity, Drugs of the Future; vol. 26(9); 2001; pp. 873-881.

Motojima, K., et. al. Peroxisome Proliferator-Activated Receptor (PPAR): Structure, Mechanisms of Activation and Diverse Functions, Cell Structure and Function; vol. 18; 1993; pp. 267-277.

Okada, H., et. al., Synthesis and Antitumor Activities of Prodrugs of Benzoylphenylureas, Chem. Pharm. Bull.; vol. 42(1); 1994; pp. 57-61.

Pineda Torra, I., et. al., Peroxisome Proliferator-activated Receptors: from Transcriptional Control to Clinical Practice, Curr. Opin. Lipidol; vol. 12; 2001; pp. 245-254.

Pineda Torra, I., et. al., Peroxisome proliferator-activated receptor alpha in metabolic disease, inflammation, atherosclerosis and aging, Curr. Opin. Lipidol; vol. 10; 1999; pp. 151-159.

Vidal-Puig, A., et. al., Regulation of PPAR γ Gene Expression by Nutrition and Obesity in Rodents, J. Clin. Invest.; vol. 97, No. 11, 1996; pp. 2553-2561.

Willson, T., M., et. al., The PPARs: From Orphan Receptors to Drug Discovery, Journal of Medicinal Chemistry; vol. 43, No. 4; 2000; pp. 527-550.

Zunft, H.J.F., et. al., Carob Pulp Preparation for Treatment of Hypercholesterolemia, Advances in Natural Therapy; vol. 18, No. 5; Sep.-Oct., 2001; pp. 230-236.

* cited by examiner

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 1
cggagtactg tcctccgag                                                    19

<210> SEQ ID NO 2
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 2
ctcggaggac agtactccg                                                    19

CYCLOALKYL DERIVATIVES HAVING BIOISOSTERIC CARBOXYLIC ACID GROUPS, PROCESSES FOR THEIR PREPARATION AND THEIR USE AS PHARMACEUTICALS

This application claims the benefit of U.S. Provisional Application No. 60/487,432, filed. Jul. 15, 2003 and priority to German Patent Application No.10308354.5, Filed Feb. 27, 2003.

The invention relates to cycloalkyl derivatives having bioisosteric carboxylic acid groups and to their physiologically acceptable salts and physiologically functional derivatives.

Compounds of a similar structure have already been described in the prior art for the treatment of hyperlipidemia and diabetes (WO 2000/64876).

The invention was based on the object of providing compounds which permit therapeutically utilizable modulation of lipid and/or carbohydrate metabolism and are thus suitable for the prevention and/or treatment of diseases such as type 2 diabetes and atherosclerosis and the diverse sequelae thereof.

A series of compounds which modulate the activity of PPA receptors has surprisingly been found. The compounds are suitable in particular for activating PPARalpha and PPARgamma, it being possible for the extent of the relative activation to vary depending on the compounds.

Accordingly, the invention relates to compounds of the formula I

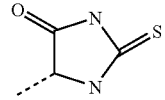

wherein
Ring A is $(C_3-C_8)$-cycloalkanediyl or $(C_3-C_8)$-cycloalkenediyl, wherein one or more of the carbon atoms of said $(C_3-C_8)$-cycloalkanediyl and $(C_3-C_8)$-cycloalkenediyl groups are optionally replaced by an oxygen atom;

$R_1$, $R_2$ are each independently H, F, Br, $CF_3$, $OCF_3$, $(C_1-C_6)$-alkyl, O—$(C_1-C_6)$-alkyl, $SCF_3$, $SF_5$, $OCF_2$—$CHF_2$, O-phenyl, OH, or $NO_2$; or $R_1$ and $R_2$, taken together with the carbon atoms of the phenyl ring to which they are attached, form a fused, unsaturated or completely or partially saturated bicyclic $(C_9-C_{12})$-aryl or $(C_9-C_{11})$-heteroaryl ring system;

R3 is H, $CF_3$, $(C_1-C_6)$-alkyl, $(C_1-C_6)$-alkoxy, $(C_3-C_8)$-cycloalkyl or phenyl;

X is $(C_1-C_6)$-alkanediyl, wherein one or more carbon atoms therein is optionally replaced by an oxygen atom;

Y is $(C_1-C_6)$-alkanediyl or $(C_1-C_6)$-alkenediyl, wherein one or more carbon atoms therein is optionally replaced by O, CO, S, SO or $SO_2$, and wherein said $(C_1-C_6)$-alkanediyl and $(C_1-C_6)$-alkenediyl groups are optionally substituted by OH;

Ring B is a group selected from (a), (b) or (c):
  (a) phenyl optionally mono- or disubstituted by $NO_2$, $Cl$, $CN$,$(C_1-C_6)$-alkyl or $(C_1-C_6)$-alkoxy
  (b) tetrazole
  (c) pyrrolidin-2-one wherein the pyrrolidinyl ring of said pyrrolidin-2-one group contains an additional nitrogen atom or a sulfur atom and is substituted by oxo or thioxo, and is optionally substituted on a nitrogen atom therein by R4;

R4 is $(C_1-C_6)$-alkyl, phenyl or benzyl;

and pharmaceutically acceptable salts thereof.

Preference is given to compounds of the formula I in which

Ring A is $(C_3-C_8)$-cycloalkanediyl or $(C_3-C_8)$-cycloalkenediyl, wherein one of the carbon atoms of said $(C_3-C_8)$-cycloalkanediyl and $(C_3-C_8)$-cycloalkenediyl groups is optionally replaced by an oxygen atom;

R1, R2 are each independently H, F, Br, $CF_3$, $OCF_3$, $(C_1-C_6)$-alkyl, O—$(C_1-C_6)$-alkyl, $SCF_3$, $SF_5$, $OCF_2$—$CHF_2$, O-phenyl, OH or $NO_2$; or $R_1$ and $R_2$, taken together with the carbon atoms of the phenyl ring to which they are attached, form a fused, unsaturated or completely or partially saturated bicyclic $(C_9-C_{12})$-aryl or $(C_9-C_{11})$-heteroaryl ring system;

R3 is H, $CF_3$, $(C_1-C_6)$-alkyl, $(C_3-C_8)$-cycloalkyl or phenyl;

X is $(C_1-C_6)$-alkanediyl, wherein one carbon atom therein is optionally replaced by an oxygen atom;

Y is $(C_1-C_6)$-alkanediyl or $(C_1-C_6)$-alkenediyl, wherein one or two carbon atoms of said $(C_1-C_6)$-alkanediyl and $(C_1-C_6)$-alkenediyl groups are optionally replaced by O, CO, S, SO or $SO_2$, and wherein said $(C_1-C_6)$-alkanediyl and $(C_1-C_6)$-alkenediyl groups are optionally substituted by OH;

Ring B is a group selected from (a), (b) or (c):
  (a) phenyl optionally mono- or disubstituted by $NO_2$, $Cl$, $CN$,$(C_1-C_6)$-alkyl or $(C_1-C_6)$-alkoxy
  (b) tetrazole
  (c) pyrrolidin-2-one wherein the pyrrolidinyl ring of said pyrrolidin-2-one group contains an additional nitrogen atom or a sulfur atom in the 4-position and is substituted by oxo or thioxo in the 5-position, and is optionally substituted on the nitrogen atom in the 1-position by R4;

R4 is $(C_1-C_6)$-alkyl, phenyl or benzyl;

and pharmaceutically acceptable salts thereof.

Particular preference is given to compounds of the formula I in which

Ring A is $(C_3-C_8)$-cycloalkanediyl wherein one carbon atom therein is replaced by an oxygen atom;

$R_1$, $R_2$ are each independently H, F, Br, $CF_3$, $OCF_3$, $(C_1-C_6)$-alkyl, O—$(C_1-C_6)$-alkyl, $SCF_3$, $SF_5$, $OCF_2$—$CHF_2$, O-phenyl, OH or $NO_2$; or $R_1$ and $R_2$, taken together with the carbon atoms of the phenyl ring to which they are attached, form a fused, unsaturated or completely or partially saturated bicyclic $(C_9-C_{12})$-aryl or $(C_9-C_{11})$-heteroaryl ring system;

R3 is H, $CF_3$, $(C_1-C_6)$-alkyl, $(C_3-C_8)$-cycloalkyl or phenyl;

X is $(C_1-C_6)$-alkanediyl, wherein the carbon atom in the 1-position is replaced by an oxygen atom;

Y is $(C_1-C_6)$-alkanediyl or $(C_1-C_6)$-alkenediyl, wherein one or two carbon atoms of said $(C_1-C_6)$-alkanediyl and $(C_1-C_6)$-alkenediyl groups are optionally replaced by O, CO or $SO_2$, and wherein said $(C_1-C_6)$-alkanediyl and $(C_1-C_6)$-alkenediyl groups are optionally substituted by OH;

Ring B is a group selected from (a), (b) or (c):
  (a) phenyl optionally mono- or disubstituted by $NO_2$, $Cl$, $CN$,$(C_1-C_6)$-alkyl or $(C_1-C_6)$-alkoxy
  (b) tetrazole
  (c) pyrrolidin-2-one wherein the pyrrolidinyl ring of said pyrrolidin-2-one group contains an additional nitrogen atom or a sulfur atom in the 4-position and is substituted by oxo or thioxo in the 5-position, and is optionally substituted on the nitrogen atom in the 1-position by R4;

R4 is $(C_1-C_6)$-alkyl, phenyl or benzyl;

and pharmaceutically acceptable salts thereof.

Very particular preference is given to compounds of the formula I in which

Ring A is cyclohexane-1,3-diyl;

$R_1$, $R_2$ are each independently H, F, Br, $CF_3$, $OCF_3$, $(C_1-C_6)$-alkyl, O—$(C_1-C_6)$-alkyl, $SCF_3$, $SF_5$, $OCF_2$—$CHF_2$, O-phenyl, OH or $NO_2$; or R1 and R2, taken together with the carbon atoms of the phenyl ring to which they are attached, form a fused, unsaturated bicyclic $(C_9-C_{10})$-aryl or $(C_9-C_{10})$-heteroaryl ring system;

R3 is H, $CF_3$, $(C_1-C_6)$-alkyl, $(C_3-C_6)$-cycloalkyl or phenyl;

X is $CH_2$—O;

Y is $(C_1-C_4)$-alkanediyl, O—$(C_1-C_4)$-alkenediyl, $(C_1-C_4)$-alkenediyl, O—$(C_1-C_4)$-alkenediyl, O—$SO_2$ or O—CO, wherein said $(C_1-C_4)$-alkanediyl group is optionally substituted by OH;

Ring B is a group selected from (a), (b) or (c):
  (a) phenyl optionally mono- or disubstituted by $NO_2$, Cl, CN, $(C_1-C_6)$-alkyl or $(C_1-C_6)$-alkoxy
  (b) tetrazole
  (c) thiazolidin-1,4-dione optionally substituted by R4 on the nitrogen in the 3-position-atom;

R4 is $(C_1-C_6)$-alkyl, phenyl or benzyl;

and pharmaceutically acceptable salts thereof.

Also preferred are compounds of the formula I in which

Ring A is cyclohexane-1,3-diyl;

$R_1$, $R_2$ are each independently H, F, Br, $CF_3$, $(C_1-C_6)$-alkyl or O—$(C_1-C_6)$-alkyl; or $R_1$ and $R_2$, taken together with the carbon atoms of the phenyl ring to which they are attached, form naphthyl;

R3 is $(C_1-C_6)$-alkyl, $(C_5-C_6)$-cycloalkyl or phenyl;

X is $CH_2$—O;

Y is $(C_1-C_4)$-alkanediyl, O—$(C_1-C_4)$-alkanediyl, $(C_1-C_4)$-alkenediyl, O—$(C_1-C_4)$-alkenediyl, O—$SO_2$ or O—CO, where said $(C_1-C_4)$-alkanediyl group is optionally substituted by OH;

Ring B is a group selected from (a), (b) or (c):
  (a) phenyl optionally mono- or disubstituted by $NO_2$, Cl, CN, $(C_1-C_6)$-alkyl or $(C_1-C_6)$-alkoxy
  (b) tetrazole
  (c) thiazolidin-2,4-dione optionally substituted by R4 on the nitrogen in the 3-position;

R4 is $(C_1-C_6)$-alkyl, phenyl or benzyl;

and pharmaceutically acceptable salts thereof.

Very particular preference is also given to the compounds of the formula I wherein:

Ring A is cyclohexane-1,3-diyl;

R2 is hydrogen;

X is $CH_2$—O—;

Y is —$CH_2$—$CH_2$—; and

Ring B is thiazolidine-2,4-dione.

Very particular preference is also given to the compounds of the formula I wherein:

R2 hydrogen and R1 is attached to the carbon of the phenyl ring that is meta- or para- to the carbon by which the phenyl ring is attached to the oxazole ring.

This invention also encompasses all combinations of preferred aspects of the invention described herein.

The alkyl radicals in the substituents R1, R2, R3 and R4 may be either straight-chain or branched.

Aryl means an aromatic carbocyclic mono- or bicyclic ring system which comprises 6 to 10 atoms in the ring or rings.

Heteroaryl is a mono- or bicyclic aromatic ring system having 4 to 11 ring members, in which at least one atom in the ring system is a heteroatom from the series N, O and S.

The compounds of the formula I comprise at least two centers of asymmetry and may comprise more in addition. The compounds of the formula I may therefore exist in the form of their racemates, racemic mixtures, pure enantiomers, diastereomers and mixtures of diastereomers. The present invention encompasses all these isomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57–61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

This invention relates further to the use of compounds of the formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct. 1993 October; 18(5): 267–77).

Two variants of PPARgamma exist, PPARgamma$_1$ and gamma$_2$, which are the result of alternative use of promoters and differential mRNA splicing (Vidal-Puig et al. J. Clin. Invest., 97:2553–2561, 1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409–435; Timothy Wilson et al. J. Med. Chem., 2000, Vol.43, No. 4, 527–550; Steven Kliewer et al., Recent Prog Horm Res. 2001; 56: 239–63.

The present invention relates to compounds of the formula I suitable for modulating the activity of PPARs, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med. 2002, 53, 409–435; Timothy Wilson et al. J. Med. Chem., 2000, Vol. 43, No. 4, 527–550; Steven Kliewer et al., Recent Prog Horm Res. 2001; 56: 239–63; Jean-Charles Fruchart, Bart Staels and Patrick Duriez: PPARS, Metabolic Disease and Arteriosclerosis, Pharmacological Research, Vol. 44, No. 5, 345–52; 2001; Sander Kersten, Beatrice Desvergne & Walter Wahli: Roles of PPARs in health and disease, NATURE, VOL 405, 25 MAY 2000; 421–4; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245–254).

Compounds of this type are particularly suitable for the treatment and/or prevention of 1. disorders of fatty acid metabolism and glucose utilization disorders
   disorders in which insulin resistance is involved
2. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Other disorders or conditions in which inflammatory reactions or cell differentiation may for example be involved are:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   pancreatitis
   other inflammatory states
   retinopathy
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
   neurodegenerative disorders
   Alzheimer's disease
   multiple sclerosis
   Parkinson's disease
   erythemato-squamous dermatoses such as, for example, psoriasis
   acne vulgaris other skin disorders and dermatological conditions which are modulated by PPAR eczemas and neurodermitis dermatitis such as, for example, seborrheic dermatitis or photodermatitis keratitis and keratoses such as, for example, seborrheic keratoses, senile keratoses, actinic keratosis, photo-induced keratoses or keratosis follicularis keloids and keloid prophylaxis warts, including condylomata or condylomata acuminata human papilloma viral (HPV) infections such as, for example, venereal papillomata, viral warts such as, for example, molluscum contagiosum, leukoplakia popular dermatoses such as, for example, Lichen planus skin cancer such as, for example, basal-cell carcinomas, melanomas or cutaneous T-cell lymphomas localized benign epidermal tumors such as, for example, keratoderma, epidermal naevi chilblains high blood pressure syndrome X polycystic ovary syndrome (PCOS)

asthma osteoarthritis lupus erythematosus (LE) or inflammatory rheumatic disorders such as, for example, rheumatoid arthritis vasculitis wasting (cachexia)

gout ischemia/reperfusion syndrome acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1–10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1 % to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantus® (see www-.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones', thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188)

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl4-oxo-2-quinazolinylmethoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)4-fluoro-1-[[(2-hydroxy-1, 1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. Nos. 6,245,744, US 6,221,897, US 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY ( 2001 September–October), 18(5), 230–6.) Caromax is a carob-containing product from Nutrinova, Nutrition Specialties & Food Ingredients GmbH, Industriepark Höechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist. In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein(a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554–558), NPY antagonists, e.g. naphthalene-1-sulfonic acid {4-[(4-aminoquinazolin-2-ylamino)methyl]-cyclohexylmethyl}amide hydrochloride (CGP 71 683A)), MC4 agonists (e.g. 1-amino-1,2,3,4-tetrahydronaphthalene-2-carboxylic acid[2-(3a-benzyl-2-methyl-3-oxo-2,3,3a ,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl) piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds was tested as follows:

Determination of EC50 Values of PPAR Agonists in the Cellular PPARalpha Assay

Principle

The potency of substances which bind to human PPARalpha and activate in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is integrated in the genome of the cell line. There is only little expression of the luciferase reporter gene without addition of a PPARalpha ligand if fatty acid-depleted fetal calf serum (cs-FCS) is used in the assay. PPARalpha ligands bind and activate the PPARalpha fusion protein and thereby bring about expression of the luciferase reporter gene. The luciferase which is formed can be detected by means of chemiluminescence via an appropriate substrate.

Construction of the Cell Line

The PPARalpha reporter cell line was prepared in 2 stages. Firstly, the luciferase reporter element was constructed and stably transfected into HEK cells. For this purpose, five binding sites of the yeast transcription factor GAL4 (each 5'-CGGAGTACTGTCCTCCGAG-3') (SEQ ID No.1) were cloned in 5'-upstream of a 68 bp-long minimal MMTV promoter (Genbank Accession #V01175). The minimal MMTV promoter section contains a CCMT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete Photinus pyralis gene (Genbank Accession #M15077) was cloned in 3'-downstream of the GAL4-MMTV element. After sequencing, the luceriferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1–3, John Wiley & Sons, Inc., 1995). Then zeocin-containing medium (0.5 mg/ml) was used to select a suitable stable cell clone which showed very low basal expression of the luceriferase gene. In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Genbank Accession #P04150) was linked to the cDNA section coding for amino acids 1–147 of the yeast transcription factor GAL4 (Genbank Accession #P04386). The cDNA of the ligand-binding domain of the human PPARalpha receptor (amino acids S167–Y468; Genbank Accession #S74349) was cloned in at the 3'-end of this GR-GAL4 construct. The fusion construct prepared in this way (GR-GAL4-humanPPARalpha-LBD) was recloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalphareporter cell line is cultivated to 80% confluence in DMEM (#41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (#353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin). Test substances are tested in 11 different concentrations in the range from 10 μM to 100 pM. More potent compounds are tested in concentration ranges from 1 μM to 10 pM or between 100 nM and 1 pM. The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. The DMSO concentration in the assay is less than 0.1 % v/v in order to avoid cytotoxic effects of the solvent. Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 μl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

The PPARalpha EC50 values for the compounds of Examples 1 to 68 in this assay are in the range from 3 nM to >10 μM.

The results for the activity of some compounds of the invention of the formula I are indicated in Table I below:

TABLE I

| Example No. | EC50 PPARalpha [nM] |
| --- | --- |
| VIII | 91 |
| XX | 1931 |
| XXI | 1251 |
| XXIV | 227 |
| XXVI | 709 |
| XXVII | 726 |
| XXXIV | 114 |
| XXXV | 187 |

It is evident from Table I that the compounds of the invention of the formula I activate the PPARalpha receptor and thus bring about for example in analogy to fibrates in clinical use a lowering of triglycerides in the body (see, for example, J.-Ch. Fruchard et al.: PPARS, Metabolic Disease and Atherosclerosis, Pharmacological Research, Vol. 44, No. 5, 345–52, 2001; S. Kersten et al.: Roles of PPARs in health and disease, NATURE, VOL 405, 25 MAY 2000, 421–4; I. Pineda et al.: Peroxisome proliferator-activated receptors: from transcriptional control to clinical practice, Curr Opin Lipidol 12: 2001, 245–254).

Determination of EC50 Values of PPAR Agonists in the Cellular PPARgamma Assay

Principle

A transient transfection system is employed to determine the cellular PPARgamma activity of PPAR agonists. It is based on the use of a luciferase reporter plasmid (pGL3basic-5xGAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5xGAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3' (SEQ ID No. 2), together with a 160 bp-long thymidine kinase promoter section (Genbank Accession #AF027128) 5'-upstream into pGL3basic. 3'-downstream of the thymidine kinase promoter is the complete luciferase gene from Photinus pyralis (Genbank Accession #M15077) which is already a constituent of the plasmid pGL3basic used. The cloning and sequencing of the reporter plasmid pGL3basic-5xGAL4-TK took place in analogy to the description in Sambrook J. et. al. (Molecular cloning, Cold Spring Harbor Laboratory Press, 1989). The PPARgamma expression plasmid pcDNA3-GAL4-humanPPARgammaLBD was prepared by first cloning the cDNA coding for amino acids 1–147 of the yeast transcription factor GAL4 (Genbank Accession #P04386) into the plasmid pcDNA3 (from Invitrogen) 3'-downstream of the cytomegalovirus promoter. Subsequently, the CDNA of the ligand-binding domain (LBD) of the human PPARgamma receptor (amino acids I152-Y475; Accession #g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5xGAL4-TK and the PPARgamma expression plasmid pcDNA3-GAL4-humanPPARgammaLBD, also used for the cellular PPARgamma assay are the reference plasmid PRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (#41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM, is prepared. The following amounts are used to make up 3 ml of solution A for each 96 well microtiter plate for an assay: 2622 μl of antibiotic- and serum-free DMEM (#41965–039, Invitrogen), 100 μl of reference plasmid PRL-CMV (1 ng/μl), 100 μl of luciferase reporter plasmid pGL3basic-5xGAL4-TK (10 ng/μl), 100 μl of PPARgamma expression plasmid pcDNA3-GAL4-humanPPARgammaLBD (100 ng/μl) and 78 μl of plasmid pBluescript SK(+) (500 ng/μl). Then 2 ml of solution B are prepared by mixing 1.9 ml of DMEM (#41965-039, Invitrogen) with 100 μl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min. 80%-confluent HEK cells from a cell culture bottle with a capacity of 175 cm$^2$ are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (#41965-039, Invitrogen) which is mixed with 10% FCS (#16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 μl of the suspension are seeded in each well of a 96 well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM (#41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 μM to 100 pM. More potent compounds are tested in concentration ranges from 1 μM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% $CO_2$.

Day 4

After removal of the medium by aspiration, 50 μl of Dual-Glo™ reagent (Dual-Glo™ Luciferase Assay System; Promega) are added to each well in accordance with the manufacturer's instructions in order to lyze the cells and provide the substrate for the firefly luciferase (Photinus pyralis) formed in the cells. After incubation at room temperature in the dark for 10 minutes, the firefly luciferase-mediated chemiluminescence is measured in a measuring instrument (measuring time/well 1 sec; Trilux from Wallac). Then 50 μl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid PRL-CMV. After incubation at room temperature in the dark for a further 10 minutes, a chemiluminescence mediated by the Renilla luciferase is again measured for 1 sec/well in the measuring instrument.

Evaluation

The crude data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS).

PPARgamma EC50 values in the range from 15 nM to >10 μM were measured for the PPAR agonists described in this application.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The examples given below serve to illustrate the invention, but without limiting it.

TABLE II

I

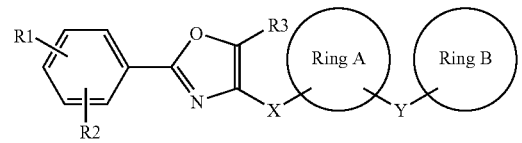

| | Ring A | Ring B | R1 | R2 | R3 | X | Y |
|---|---|---|---|---|---|---|---|
| I | 1,3-Cy | 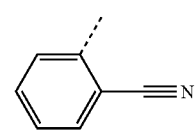 | 4-F | H | Me | CH2-O | --O—CH2-- |

TABLE II-continued

I

| | Ring A | Ring B | R1 | R2 | R3 | X | Y |
|---|---|---|---|---|---|---|---|
| II | 1,3-Cy | 3-cyanophenyl | 4-F | H | Me | CH2-O | --O—CH2-- |
| III | 1,3-Cy | 4-cyanophenyl | 4-F | H | Me | CH2-O | --O—CH2-- |
| IV | 1,3-Cy | 2-(tetrazol-5-yl)phenyl | 4-F | H | Me | CH2-O | --O—CH2-- |
| V | 1,3-Cy | 3-(tetrazol-5-yl)phenyl | 4-F | H | Me | CH2-O | --O—CH2-- |
| VI | 1,3-Cy | 4-(tetrazol-5-yl)phenyl | 4-F | H | Me | CH2-O | --O—CH2-- |
| VII | 1,3-Cy | 2-nitrophenyl | 4-F | H | Me | CH2-O | --O—CH2-- |
| VIII | 1,3-Cy | 3-nitrophenyl | 4-F | H | Me | CH2-O | --O—CH2-- |
| IX | 1,3-Cy | 4-nitrophenyl | 4-F | H | Me | CH2-O | --O—CH2-- |
| X | 1,3-Cy | 2-methoxy-4-nitrophenyl | 4-F | H | Me | CH2-O | --O—CH2-- |
| XI | 1,3-Cy | 2,4-dinitrophenyl | 4-F | H | Me | CH2-O | --O—C(=O)-- |

TABLE II-continued
I
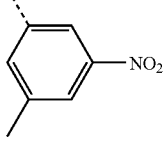
| | Ring A | Ring B | R1 | R2 | R3 | X | Y |
|---|---|---|---|---|---|---|---|
| XII | 1,3-Cy | 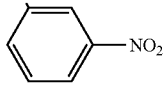 | 4-F | H | Me | CH2-O | --O—C(=O)-- |
| XIII | 1,3-Cy | 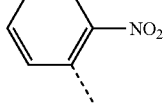 | 4-F | H | Me | CH2-O | --O—C(=O)-- |
| XIV | 1,3-Cy | 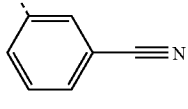 | 4-F | H | Me | CH2-O | --O—C(=O)-- |
| XV | 1,3-Cy | 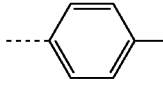 | 4-F | H | Me | CH2-O | --O—C(=O)-- |
| XVI | 1,3-Cy | 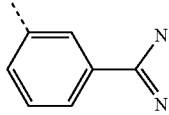 | 4-F | H | Me | CH2-O | --O—C(=O)-- |
| XVII | 1,3-Cy | 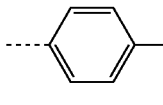 | 4-F | H | Me | CH2-O | --O—C(=O)-- |
| XVIII | 1,3-Cy | 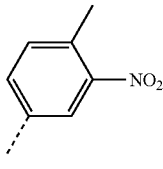 | 4-F | H | Me | CH2-O | --O—C(=O)-- |
| XIX | 1,3-Cy | 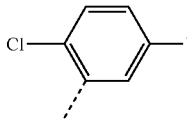 | 4-F | H | Me | CH2-O | --O—S(=O)2-- |
| XX | 1,3-Cy |  | 4-F | H | Me | CH2-O | --O—S(=O)2-- |

TABLE II-continued

I

| | Ring A | Ring B | R1 | R2 | R3 | X | Y |
|---|---|---|---|---|---|---|---|
| XXI | 1,3-Cy | 4-methoxy-2-nitrophenyl | 4-F | H | Me | CH2-O | --O—S(=O)2-- |
| XXII | 1,3-Cy | thiazolidine-2,4-dione-5-yl | 4-F | H | Me | CH2-O | --O—CH2-CH= |
| XXIII | 1,3-Cy | thiazolidine-2,4-dione-5-yl | 3-Me | H | Me | CH2-O | --O—CH2-CH= |
| XXIV | 1,3-Cy | imidazolidine-2,4-dione-5-yl | 4-F | H | Me | CH2-O | --O—CH2-CH= |
| XXV | 1,3-Cy | | 4-F | H | Me | CH2-O | --O—CH2-CH= |
| XXVI | 1,3-Cy | thiazolidine-2,4-dione-5-yl | 4-F | H | Me | CH2-O | --O—CH2-CH-- |
| XXVII | 1,3-Cy | thiazolidine-2,4-dione-5-yl | 3-Me | H | Me | CH2-O | --O—CH2-CH-- |
| XXVIII | 1,3-Cy | thiazolidine-2,4-dione-5-yl | 3-Me | H | Me | CH2-O | --CH2-CH(OH)-- |
| XXIX | 1,3-Cy | thiazolidine-2,4-dione-5-yl | 3-OMe | H | Me | CH2-O | --CH2-CH(OH)-- |
| XXX | 1,3-Cy | thiazolidine-2,4-dione-5-yl | 4-Me | H | Me | CH2-O | --CH2-CH(OH)-- |
| XXXI | 1,3-Cy | thiazolidine-2,4-dione-5-yl | 3-Me | H | Me | CH2-O | --CH2-CH2-- |

TABLE II-continued

I

| | Ring A | Ring B | R1 | R2 | R3 | X | Y |
|---|---|---|---|---|---|---|---|
| XXXII | 1,3-Cy | thiazolidinedione | 3-OMe | H | Me | CH2-O | --CH2-CH2-- |
| XXXIII | 1,3-Cy | thiazolidinedione | 4-Me | H | Me | CH2-O | --CH2-CH2-- |
| XXXIV | 1,3-Cy | thiazolidinedione | 4-Me | H | Me | CH2-O | --CH= |
| XXXV | 1,3-Cy | thiazolidinedione | 4-Me | H | Me | CH2-O | --CH2-- |
| XXXVI | 1,3-Cy | thiazolidinedione | 3-OMe | H | Cy | CH2-O | --CH2-CH2-- |
| XXXVII | 1,3-Cy | thiazolidinedione | 4-Me | H | Cy | CH2-O | --CH2-CH2-- |
| XXXVIII | 1,3-Cy | thiazolidinedione | 3-$CF_3$ | 5-$CF_3$ | Et | CH2-O | --CH2-CH2-- |
| XXXIX | 1,3-Cy | thiazolidinedione | 2-Me | 6-Me | Et | CH2-O | --CH2-CH2-- |
| XL | 1,3-Cy | thiazolidinedione | 2-$CF_3$ | H | Me | CH2-O | --CH2-CH2-- |
| XLI | 1,3-Cy | thiazolidinedione | 3-OMe | H | Et | CH2-O | --CH2-CH2-- |
| XLII | 1,3-Cy | thiazolidinedione | 2-$CF_3$ | H | Et | CH2-O | --CH2-CH2-- |

TABLE II-continued
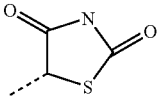
I
| | Ring A | Ring B | R1 | R2 | R3 | X | Y |
|---|---|---|---|---|---|---|---|
| XLIII | 1,3-Cy | 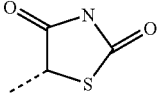 | 4-Me | H | Et | CH2-O | --CH2-CH2-- |
| XLIV | 1,3-Cy | 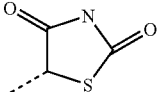 | 4-iPr | H | Et | CH2-O | --CH2-CH2-- |
| XLV | 1,3-Cy | 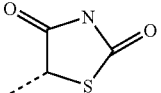 | 4-Me | H | iPr | CH2-O | --CH2-CH2-- |
| XLVI | 1,3-Cy | 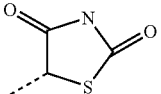 | 3-CF$_3$ | H | Me | CH2-O | --CH2-CH2-- |
| XLVIIa[1] | 1,3-Cy | 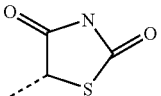 | 3-Me | H | Me | CH2-O | --CH2-CH2-- |
| XLVIIb[2] | 1,3-Cy | 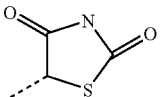 | 3-Me | H | Me | CH2-O | --CH2-CH2-- |
| XLVIIIa[2] | 1,3-Cy | 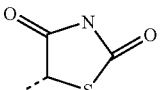 | 4-iPr | H | Et | CH2-O | --CH2-CH2-- |
| XLVIIIb[1] | 1,3-Cy | 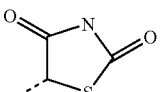 | 4-iPr | H | Et | CH2-O | --CH2-CH2-- |
| XLIXa[2] | 1,3-Cy | 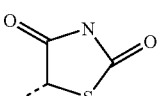 | 4-Me | H | Me | CH2-O | --CH2-CH2-- |
| XLIXb[1] | 1,3-Cy | 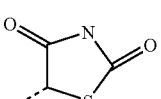 | 4-Me | H | Me | CH2-O | --CH2-CH2-- |
| L[2] | 1,3-Cy |  | 3-Me | 4-Me | Et | CH2-O | --CH2-CH2-- |

TABLE II-continued

I

![Structure: R1/R2-phenyl-oxazole(R3)-X-RingA-Y-RingB]

| | Ring A | Ring B | R1 | R2 | R3 | X | Y |
|---|---|---|---|---|---|---|---|
| LI[2] | 1,3-Cy | thiazolidine-2,4-dione | 4-CF₃ | H | Et | CH2-O | --CH2-CH2-- |
| LII[2] | 1,3-Cy | thiazolidine-2,4-dione | 2-Naphthyl | | Et | CH2-O | --CH2-CH2-- |
| LIII[2] | 1,3-Cy | thiazolidine-2,4-dione | 3-CF₃ | H | Et | CH2-O | --CH2-CH2-- |
| LIV[2] | 1,3-Cy | thiazolidine-2,4-dione | 4-ᵗBu | H | Et | CH2-O | --CH2-CH2-- |
| LV[2] | 1,3-Cy | thiazolidine-2,4-dione | 3-Me | 4-Me | ⁱPr | CH2-O | --CH2-CH2-- |
| LVI[2] | 1,3-Cy | thiazolidine-2,4-dione | 4-ⁱBu | H | Et | CH2-O | --CH2-CH2-- |
| LVII[2] | 1,3-Cy | thiazolidine-2,4-dione | 3-CF₃ | H | ⁱPr | CH2-O | --CH2-CH2-- |
| LVIII[2] | 1,3-Cy | thiazolidine-2,4-dione | 4-ᵗBu | H | ⁱPr | CH2-O | --CH2-CH2-- |
| LIX[2] | 1,3-Cy | thiazolidine-2,4-dione | 4-ⁱBu | H | ⁱPr | CH2-O | --CH2-CH2-- |
| LX[2] | 1,3-Cy | thiazolidine-2,4-dione | 4-CF₃ | H | ⁱPr | CH2-O | --CH2-CH2-- |
| LXI[2] | 1,3-Cy | thiazolidine-2,4-dione | 2-Naphthyl | | ⁱPr | CH2-O | --CH2-CH2-- |

TABLE II-continued

I

| | Ring A | Ring B | R1 | R2 | R3 | X | Y |
|---|---|---|---|---|---|---|---|
| LXII | 1,3-Cy | (N-Me thiazolidinedione) | 3-OMe | H | Me | CH2-O | --CH2-CH2-- |
| LXIII | 1,3-Cy | (N-Ph thiazolidinedione) | 3-OMe | H | Me | CH2-O | --CH2-CH2-- |
| LXIV | 1,3-Cy | (N-Me thiazolidinedione) | 4-Me | H | Me | CH2-O | --CH2-CH2-- |
| LXV | 1,3-Cy | (N-benzyl thiazolidinedione) | 4-Me | H | Me | CH2-O | --CH2-CH2-- |
| LXVI | 1,3-Cy | (N-Me thiazolidinedione) | 3-OMe | H | $^i$Pr | CH2-O | --CH2-CH2-- |
| LXVII | 1,3-Cy | (N-Me thiazolidinedione) | 3-OMe | H | Ph | CH2-O | --CH2-CH2-- |
| LXVIII | 1,3-Cy | (N-Ph thiazolidinedione) | 3-OMe | H | Ph | CH2-O | --CH2-CH2-- |

1,3-Cy is defined as:
cis-1,3-cyclohexanediol having the stereochemistry according to Cahn-Ingold-Prelog as stated in the examples.
The point of attachment of ring B to Y and the points of attachment of Y to ring A and ring B are shown as a broken line (--).
[1] (1R, 3R) enantiomer
[2] (1S, 3S) enantiomer Also described is a process for preparing the compounds of the formula I according to reaction schemes A to H below:

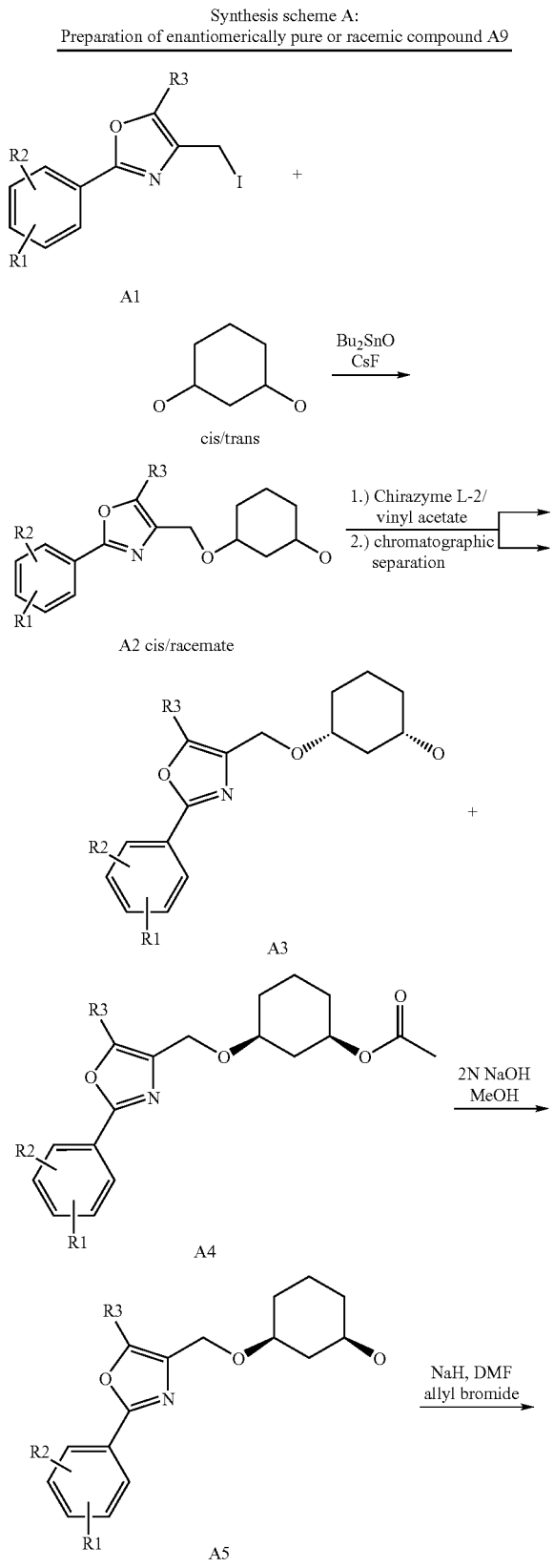

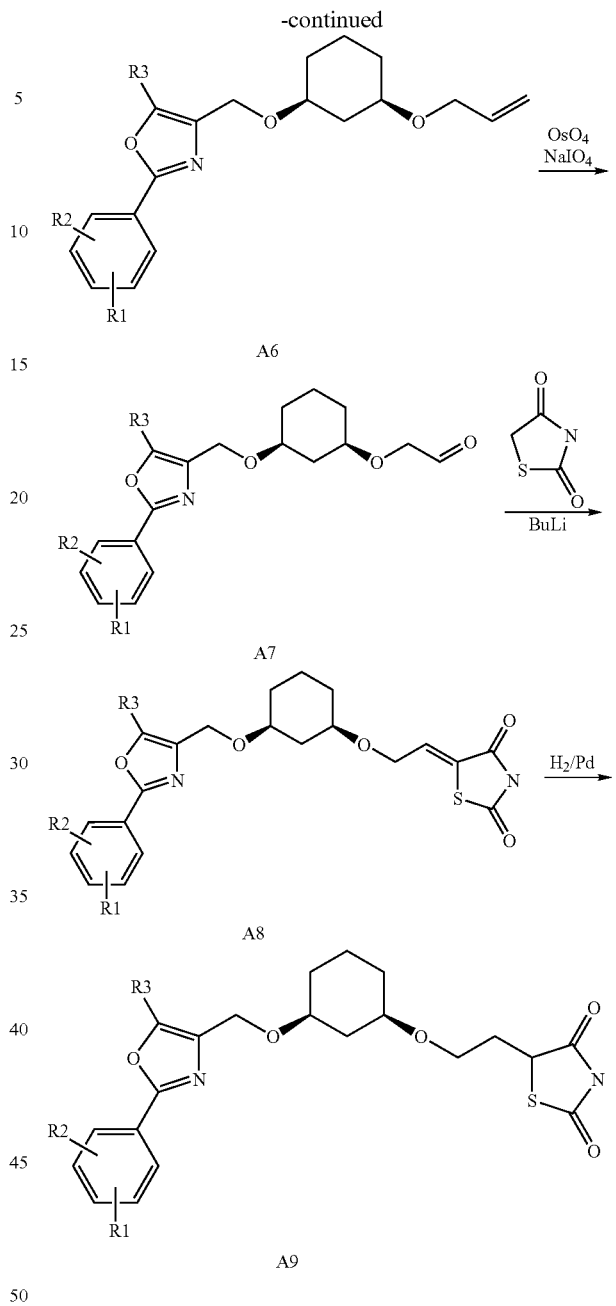

Initially, cyclohexanediol is heated with dibutyltin oxide in toluene on a water separator for a number of hours and then, with addition of dimethylformamide, cesium fluoride and an oxazole of the formula A1 in which R1, R2 and R3 are as defined above, converted by stirring at room temperature for a number of hours into a compound of the formula A2 in which R1, R2 and R3 are as defined above.

The compound of the formula A2 is reacted using Chirazyme L2 and vinyl acetate. This results in the formation of compounds A3 and A4, of which A4, after separation, is reacted with alkali metal hydroxides to give a compound of the structure A5 in which R1, R2 and R3 are as defined above.

The compound of the formula A5 or A2 is converted into an enantiomerically pure or racemic compound of the structure A6 in which R1, R2 and R3 are as defined above. To form the ether bond, A5 or A2 is deprotonated, for example in an aprotic solvent such as dimethylformamide, using strong bases, for example sodium hydride, and reacted with unsaturated bromides, for example allyl bromides.

The enantiomerically pure or racemic compound of the formula A6 is, using osmium tetroxide and sodium periodate, converted into the enantiomerically pure or racemic compound of the structure A7 in which R1, R2 and R3 are as defined above.

The enantiomerically pure or racemic compound of the formula A7 is converted into enantiomerically pure or racemic compounds of the structure A8 in which R1, R2 and R3 are as defined above. Here, thiazolidinedione is initially deprotonated in an inert solvent using a strong base, for example n-butyllithium, and then, at −70° C., reacted with component A7, giving, after acidic work-up, for example with 6N hydrochloric acid, the compound A8.

The enantiomerically pure or racemic compound A8 is, by hydrogenation, using, for example, palladium-on-carbon as catalyst in solvents such as methanol or ethyl acetate, converted into an enantiomerically pure or racemic compound of the formula A9 in which R1, R2 and R3 are as defined above.

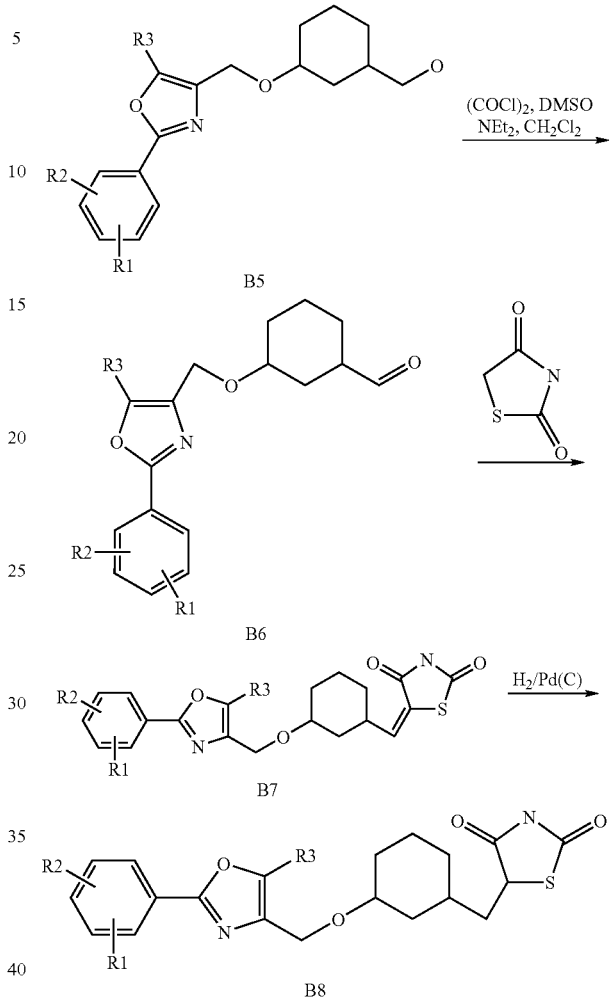

The compound of the formula B4 in which R1, R2 and R3 are as defined above is obtained from lactone B1 by lithium aluminum hydride reduction to diol B2, selective silylation at the primary alcohol function giving compound B3, deprotonation using strong bases, for example sodium hydride in an aprotic solvent such as dimethylformamide, and alkylation with phenyloxazoyl iodides of the formula A1, in which R1, R2 and R3 are as defined above.

The compound of the formula B4 in which R1, R2 and R3 are as defined above is converted into a compound of the structure B5 in which R1, R2 and R3 are as defined above, for example by removing the silyl protective group with fluoride, for example tetrabutylammonium fluoride.

Using osmium tetroxide and sodium periodate, the compound of the formula B5 is converted into the compound of the structure B6 in which R1, R2 and R3 are as defined above.

The compound of the formula B6 is converted into a compound of the structure B7 in which R1, R2 and R3 are as defined above. Here, thiazolidinedione is initially deprotonated in an inert solvent using a strong base, such as, for example, n-butyllithium, and then, at −70° C., reacted with component B6 giving, after acidic work-up, for example with 6N hydrochloric acid, compound B7.

Compound B7 is converted by hydrogenation, for example at a hydrogen pressure of 3 bar using palladium-on-carbon as catalyst in solvents such as methanol or ethyl acetate, into a compound of the formula B8 in which R1, R2 and R3 are as defined above.

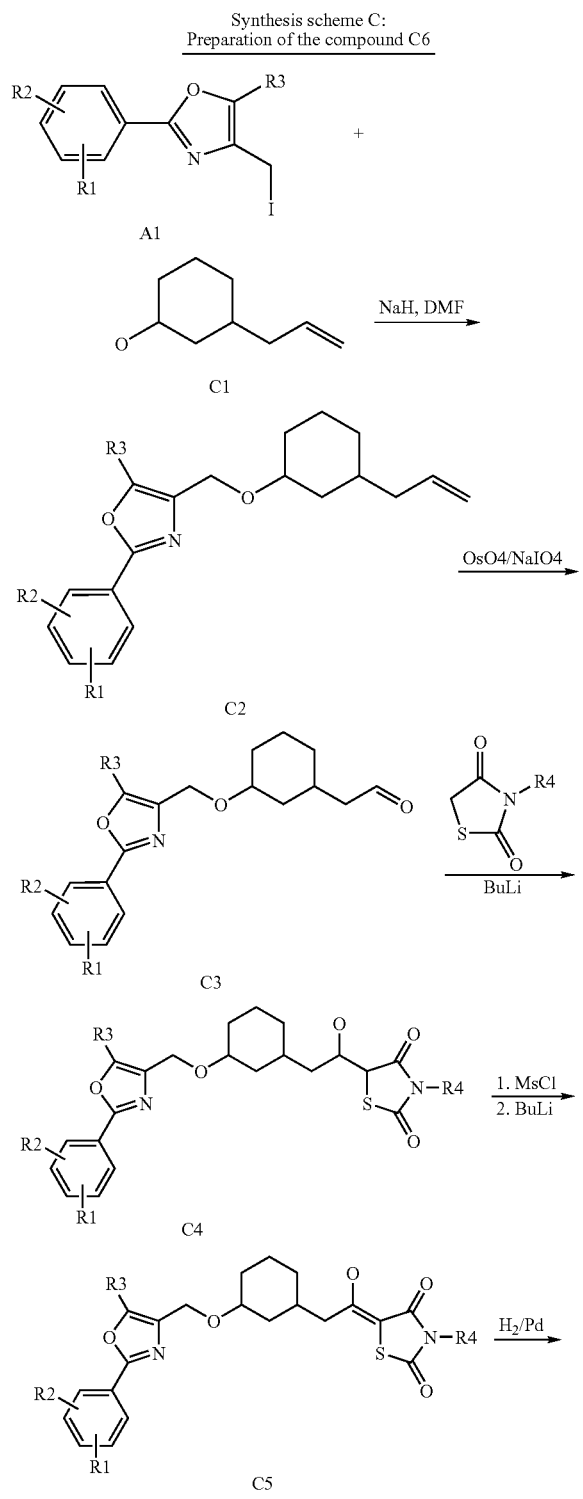

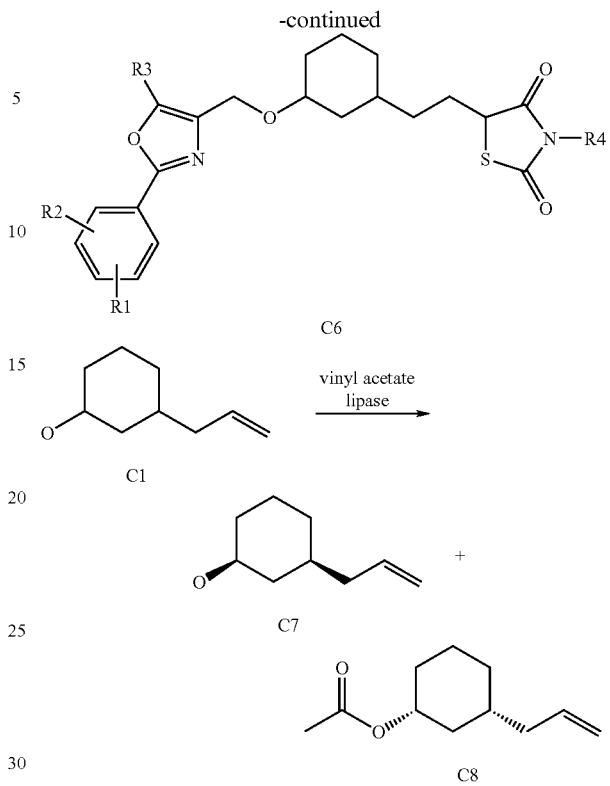

Compounds of the formula A1 in which R1, R2 and R3 are as defined above are dissolved with cis-3-allylcyclohexanol C1 (or optionally with (1 S,3S)-3-allylcyclohexanol C7) in aprotic solvents, such as dimethylformamide, and reacted with strong bases, such as, for example, sodium hydride, giving compounds of the formula C2 in which R1, R2 and R3 are as defined above.

The compound of the formula C2 is, using osmium tetroxide and sodium periodate, converted into the compound of the structure C3 in which R1, R2 and R3 are as defined above.

The compound of the formula C3 is converted into a compound of the structure C4 in which R1, R2, R3 and R4 are as defined above. Here, thiazolidinedione is initially deprotonated in an inert solvent using a strong base, such as, for example, n-butyllithium, and then, at −70° C., reacted with component C3, giving, after work-up, for example with 1N hydrochloric acid, a compound of the formula C4.

The compound C4 is converted into a compound of the formula C5 in which R1, R2, R3 and R4 are as defined above. Alcohol C4 is, for example, mixed with mesyl chloride and triethylamine in polar solvents, such as dichloromethane, and the crude product is, at −70° C., converted with n-butyllithium into C5.

The compound of the formula C5 is converted by hydrogenation, for example at a hydrogen pressure of 5 bar using palladium-on-carbon as catalyst in ethyl acetate, into a compound of the formula C6 in which R1, R2, R3 and R4 are as defined above.

Enantiomerically pure (1S,3S)-3-allylcyclohexanol C7 can be obtained from racemic C1 by treatment with lipase in vinyl acetate. The coproduct (1R,3R)-3-allylcyclohexanyl acetate C8 can be removed chromatographically.

Synthesis scheme D:
Preparation of compound D2

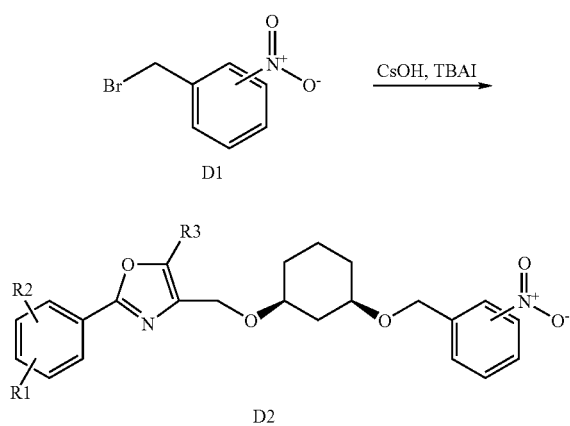

The compound of the formula A5 or A2 is converted using bases, for example cesium hydroxide in a mixture of water and acetonitrile, using a phase-transfer catalyst, for example tetrabutylammonium iodide, with nitrobenzyl bromides of the formula D1 into enantiomerically pure or racemic compounds of the structure D2 in which R1, R2 and R3 are as defined above.

Synthesis scheme E:
Preparation of enantiomerically pure or racemic compound E3

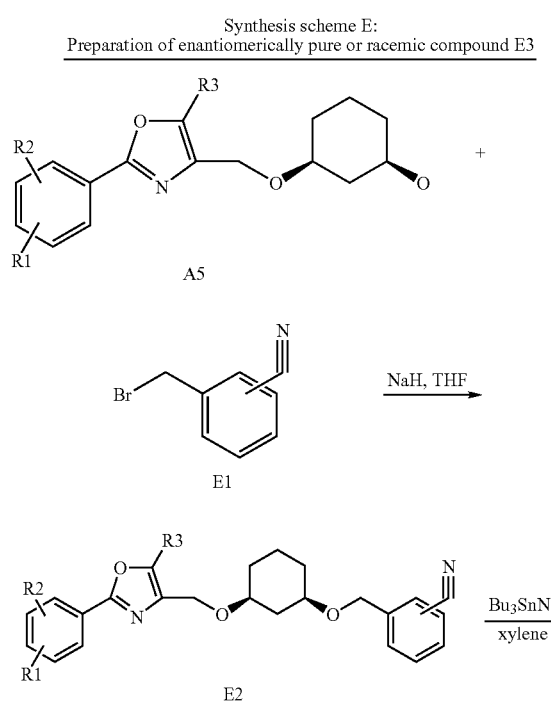

The compound of the formula A5 or A2 is, using strong bases, for example sodium hydride, deprotonated in an aprotic solvent and reacted with cyanobenzyl bromides of the formula E1, giving enantiomerically pure or racemic compounds of the structure E2 in which R1, R2 and R3 are as defined above. The compound of the formula E2 is, using a metal azide, for example tributyltin azide, converted into enantiomerically pure or racemic compounds of the structure E3 in which R1, R2, and R3 are as defined above.

Synthesis scheme F:
Preparation of enantiomerically pure or racemic compound F2

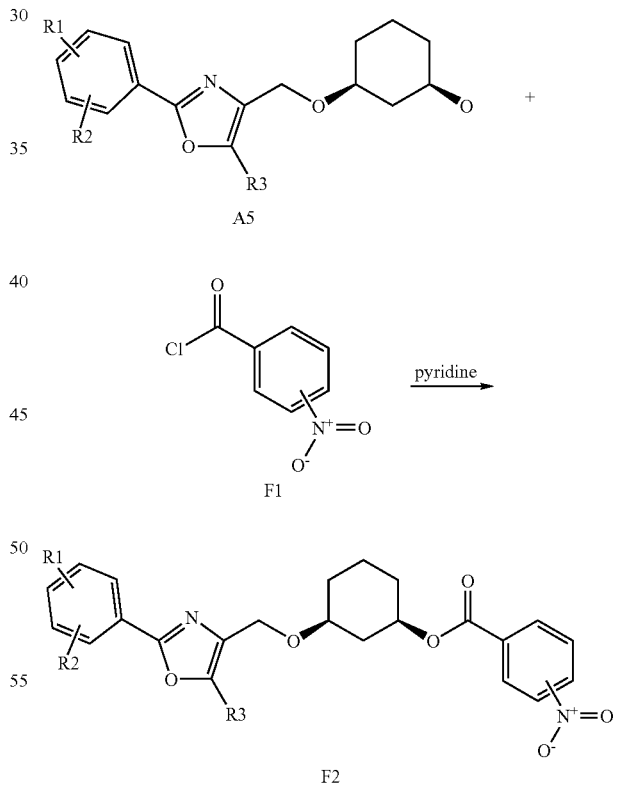

The compound of the formula A5 or A2 is, using bases, for example pyridine, reacted at about 50° C. with nitrobenzoyl chlorides of the formula F1, giving enantiomerically pure or racemic compounds of the formula F2 in which R1, R2 and R3 are as defined above.

Synthesis scheme G:
Preparation of enantiomerically pure or racemic compound G3

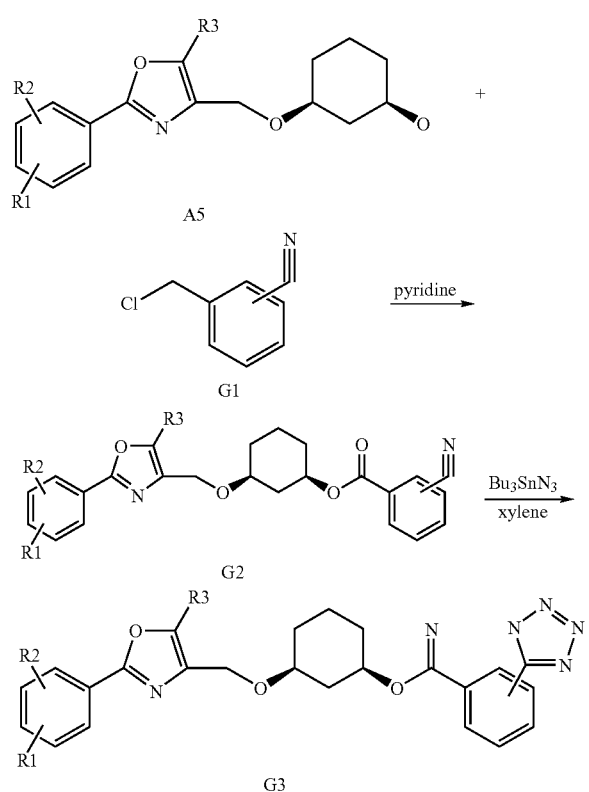

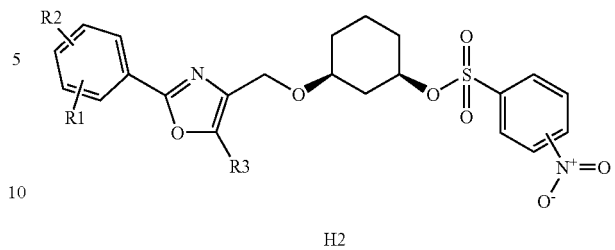

The compound of the formula A5 or A2 is, using bases, for example pyridine, reacted at about 50° C. with cyanobenzoyl chlorides of the formula G1, giving enantiomerically pure or racemic compounds of the formula G2 in which R1, R2 and R3 are as defined above.

The compound of the formula G2 is, using a metal azide, for example tributyltin azide, converted at about 160° C. into enantiomerically pure or racemic compounds of the structure G3 in which R1, R2 and R3 are as defined above.

Synthesis scheme H:
Preparation of enantiomerically pure or racemic compound H2

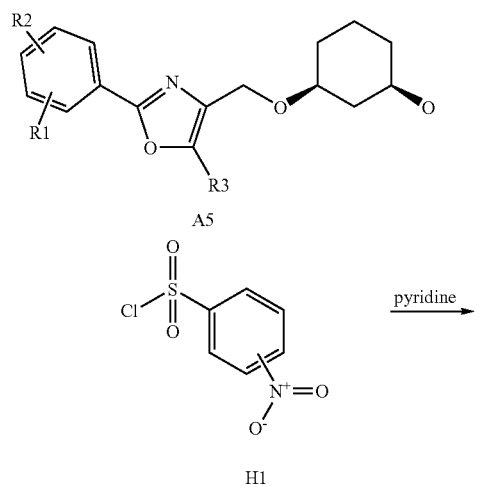

The compound of the formula A5 or A2 is, using bases, for example pyridine, reacted at room temperature with nitrobenzenesulfonyl chlorides of the formula G1, giving enantiomerically pure or racemic compounds of the formula G2 in which R1, R2 and R3 are as defined above.

The abbreviations used denote:
Ac acetyl
$^i$Bu isobutyl
$^t$Bu tert-butyl
BuLi n-butyllithium
Cy cyclohexyl
TLC thin-layer chromatography
DCI direct chemical ionization (MS)
DCM dichloromethane
DMAP 4-N,N-dimethylaminopyridine
DMF N,N-dimethylformamide
DMSO dimethyl sulfoxide
EA ethyl acetate
EDC N'-(3-dimethylaminopropyl)-N-ethylcarbodiimide×HCl
El electron impact ionization (MS)
eq equivalent
ESI electron spray ionization (MS)
Et ethyl
Sat. saturated
h hour
HATU O-(7-azabenzotriazol-1-yl)-N,N,N',N'-tetramethyluronium hexafluorophosphate
HOBt 1-hydroxy-1H-benzotriazole×H$_2$O
HPLC high pressure, high performance liquid chromatography
LC-MS liquid-chromatography-coupled mass spectroscopy
Me methyl
MS mass spectroscopy
MsCl methanesulfonyl chloride
NMR nuclear magnetic resonance spectroscopy
Pd/C palladium-on-carbon
$^i$Pr isopropyl
$^n$Pr n-propyl
R$_f$ retention time (TLC)
RT room temperature
TBAF tetrabutylammonium fluoride
TBAI tetrabutylammonium iodide
TBDPSCl tert-butyldiphenylsilyl chloride
THF tetrahydrofuran Other compounds of the formula I to be obtained by known processes are in accordance with the reaction schemes described above.

EXAMPLE I 2-(4-Fluorophenyl)-5-methyl-4-[cis-3-(2-cyanobenzyloxy)cyclohexyl-oxymethyl]oxazole rac-3-(cis-5-methyl-2-m-tolyloxazol-4-ylmethoxy)cyclohexanol

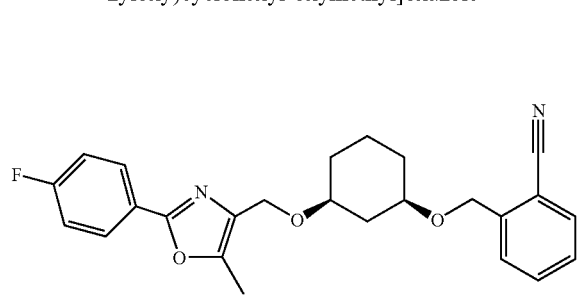

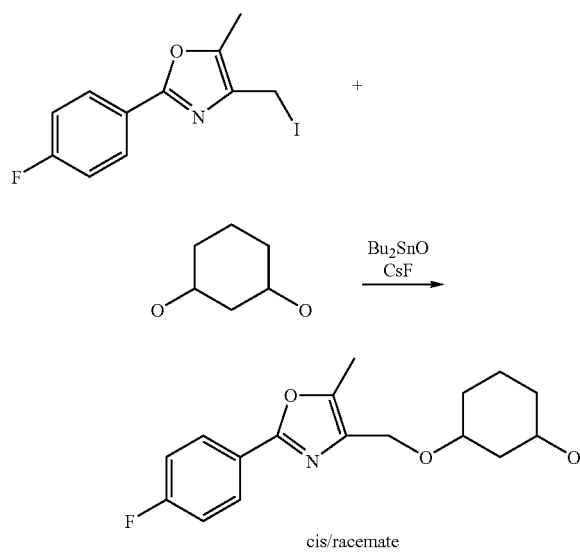

cis/racemate 21.7 g of 1,3-cyclohexanediol and 30.3 g of dibutyltin oxide are dissolved in 450 ml of toluene and, under reflux on a water separator, heated to boiling. During the reaction, the reaction volume is reduced to half the original volume. After 3 hours, the reaction mixture is cooled to room temperature, and 300 ml of dimethylformamide, 29 g of 2-(4-fluorophenyl)-4-iodomethyl-5-methyloxazole 1 and 23.5 g of cesium fluoride are added. The mixture is stirred at room temperature for 18 hours. The reaction mixture is diluted by addition of ethyl acetate and washed with saturated sodium chloride solution. The organic phase is dried over magnesium sulfate, the solvent is removed under reduced pressure and the residue is purified by flash chromatography on silica gel (n-heptane/ethyl acetate=10:1→1:4). This gives 58 g of rac-3-[2-(4-fluorophenyl)-5-methyloxazol-4-ylmethoxy]cyclohexanol as a yellowish solid which is recrystallized from n-heptane/ethyl acetate. $C_{17}H_{20}FNO_3$ (305.35), MS (ESI): 306 (M+H$^+$).

(1R,3S)-3-[2-(4-Fluorophenyl)-5-methyloxazol4-ylmethoxy]cyclohexanol

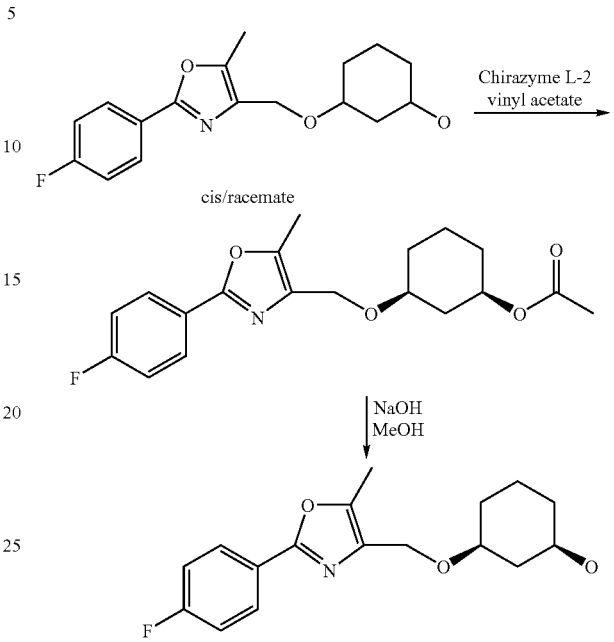

25 g of rac-cis-3-[2-(4-fluorophenyl)-5-methyloxazol-4-ylmethoxy]cyclohexanol are dissolved in 320 ml of vinyl acetate, and 1.3 g of Chirazyme L-2 Lyo (Boehringer Mannheim) are added. The mixture is stirred at room temperature for three hours (checked by LC-MS for 40–45% conversion) and the enzyme is then filtered off and washed with ethyl acetate, and the solvent is removed under reduced pressure. The residue is purified by flash chromatography on silica gel (n-heptane/ethyl acetate=3:1). This gives 8 g of (1 R, 3S)-3-[2-(4-fluorophenyl)-5-methyloxazyol-4-ylmethoxy]cyclohexyl acetate as a colorless oil. $C_{19}H_{22}FNO_4$ (347.39), MS (ESI): 348 (M+H$^+$). The acetate is taken up in 170 ml of methanol and, after addition of 27 ml of 2N aqueous sodium hydroxide solution, stirred at room temperature for one hour. Most of the solvent is removed under reduced pressure. After addition of in each case 150 ml of water and ethyl acetate, the organic phase is washed with sodium chloride solution. The organic phase is dried over magnesium sulfate and the solvent is removed under reduced pressure. This gives 6.7 g of 3-(1R,3S)-3-[2-(4-fluorophenyl)-5-methyloxazol4-ylmethoxy]cyclohexanol as a yellowish solid. $C_{17}H_{20}FNO_3$ (305.35), MS (ESI): 306 (M+H$^+$).

2-(4-Fluorophenyl)-5-methyl4-[cis-3-(2-cyanobenzyloxy)cyclohexyl-oxymethyl]oxazole

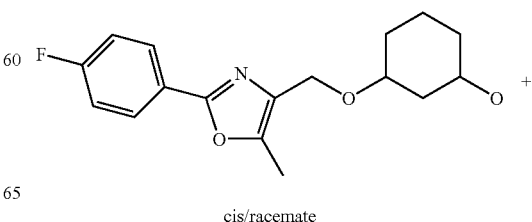

cis/racemate

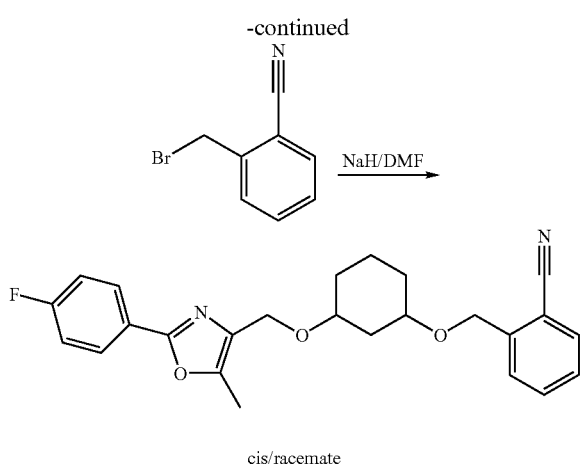

cis/racemate

In a 25 ml two-necked flask which had been dried by heating, 0.15 g of the alcohol 3-[2-(4-fluorophenyl)-5-methyloxazol-4-ylmethoxy]cyclohexanol is dissolved in 5 ml of dimethylformamide (dry), and 0.05 g of sodium hydride is added. The mixture is stirred for 15 minutes, 0.19 g of 2-(bromomethyl)benzonitrile is then added, and the mixture is stirred at room temperature for 24 hours. The reaction is terminated by addition of 2 ml of 1N hydrochloric acid and the mixture is extracted with ethyl acetate (2×10 ml). The combined organic phases are washed with saturated sodium chloride solution and dried over magnesium sulfate and the solvent is then removed under reduced pressure. Purification by preparative HPLC gives 0.07 g of the desired product 2-(4-fluorophenyl)-5-methyl-4-[cis-3-(2-cyanobenzyloxy)cyclohexyloxymethyl]oxazole as a colorless oil. $C_{25}H_{25}FN_2O_3$ (420.48), MS (ESI): 421 (M+H$^+$).

EXAMPLE II 2-(4-Fluorophenyl)-5-methyl4-[cis-3-(3-cyanobenzyloxy)cyclohexyloxy-methyl]oxazole Analogously to Example I, the alcohol 3-[2-(4-fluorophenyl)-5-methyloxazol4-ylmethoxy]cyclohexanol and 3-(bromomethyl)benzonitrile give the compound 2-(4-fluorophenyl)-5-methyl-4-[cis-3-(3-cyanobenzyloxy)-cyclohexyloxymethyl]oxazole:

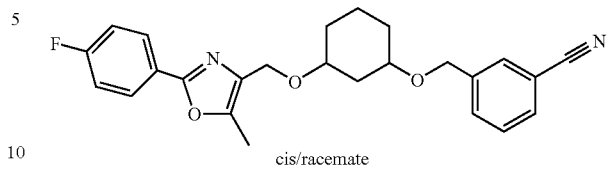

cis/racemate $C_{25}H_{25}FN_2O_3$ (420.48), MS (ESI): 421 (M+H$^+$).

EXAMPLE III 2-(4-Fluorophenyl)-5-methyl-4-[cis-3-(4-cyanobenzyloxy)cyclohexyl-oxymethyl]oxazole Analogously to Example I, the alcohol 3-[2-(4-fluorophenyl)-5-methyloxazol-4-ylmethoxy]cyclohexanol and 4-(bromomethyl)benzonitrile give the compound 2-(4-fluorophenyl)-5-methyl-4-[cis-3-(4-cyanobenzyloxy)-cyclohexyloxymethyl]oxazole:

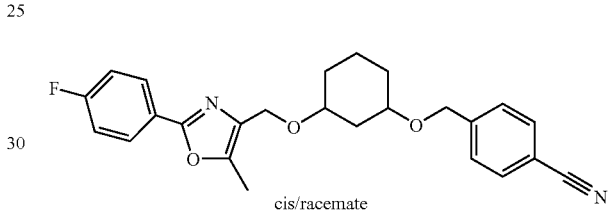

cis/racemate $C_{25}H_{25}FN_2O_3$ (420.48), MS (ESI): 421 (M+H$^+$).

The compounds synthesized in this manner (Example I–III) can be converted into the corresponding tetrazoles:

EXAMPLE IV 5-(2-{cis-3-[2-(4-Fluorophenyl)-5-methyloxazol-4-ylmethoxy]cyclo-hexyloxymethyl}phenyl)-1-H-tetrazole

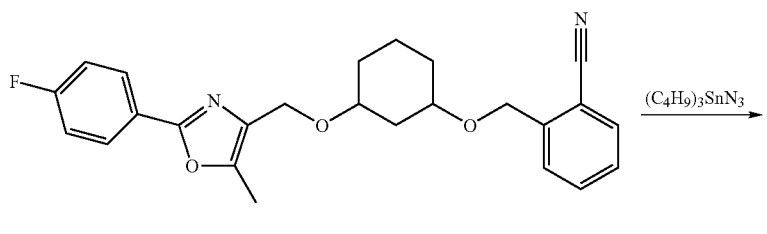

cis/racemate

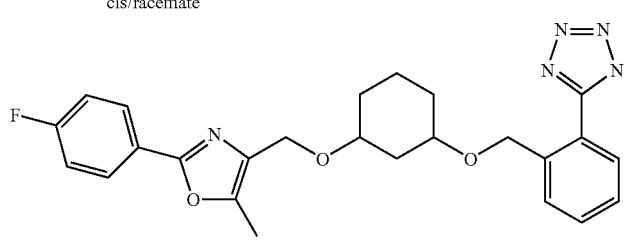

cis/racemate 0.03 g of the nitrile 2-(4-fluorophenyl)-5-methyl-4-[cis-3-(2-cyanobenzyloxy)cyclohexyloxymethyl]oxazole are dissolved in 5 ml of xylene, 50 μl of tributyltin azide are added and the mixture is heated under reflux at 160° C. for 24 hours. The reaction is terminated by addition of 1 ml of trifluoroacetic acid (in 1 ml of methanol), 3 ml of water are added and the mixture is extracted with ethyl acetate (2×10 ml). The combined organic phases are washed with saturated sodium chloride solution and dried over magnesium sulfate, and the solvent is then removed under reduced pressure. Purification by preparative HPLC gives 0.02 g of the desired 5-(2-{cis-3-[2-(4-fluorophenyl)-5-methyloxazol-4-ylmethoxy]cyclohexyloxy-methyl}phenyl)-1-H-tetrazole as an amorphous solid. $C_{25}H_{26}FN_5O_3$ (463.51), MS (ESI): 464 (M+H⁺).

EXAMPLE V 5-(3-{cis-3-[2-(4-Fluorophenyl)-5-methyloxazol4-ylmethoxy]cyclohexyloxymethyl}phenyl)-1H-tetrazole Analogously to Example IV, 2-(4-fluorophenyl)-5-methyl4-[cis-3-(3-cyanobenzyloxy)cyclohexyloxymethyl]oxazole from Example II gave, by reaction with tributyltin hydride, 5-(3-{cis-3-[2-(4-fluorophenyl)-5-methyloxazol4-ylmethoxy]cyclohexyloxymethyl}phenyl)-1H-tetrazole:

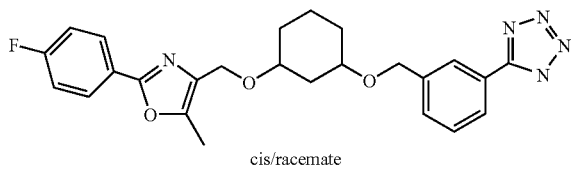

cis/racemate $C_{25}H_{26}FN_5O_3$ (463.51), MS (ESI): 464 (M+H⁺).

EXAMPLE VI 5-(4-{cis-3-[2-(4-Fluorophenyl)-5-methyloxazol4-ylmethoxy]cyclohexyloxymethyl}phenyl)-1H-tetrazole Analogously to Example IV, 2-(4-fluorophenyl)-5-methyl4-[cis-3-(4-cyanobenzyloxycyclohexloxymethyl]oxazole from Example III gave, by reaction with tributyltin hydride, 5-(4-{cis-3-[2-(4-fluorophenyl)-5-methyloxazol4-ylmethoxy]cyclohexyloxymethyl}phenyl)-1H-tetrazole:

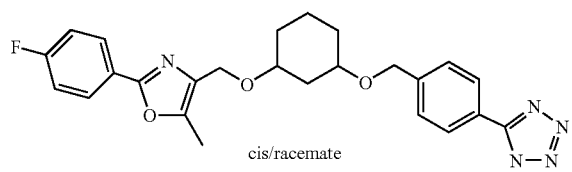

cis/racemate $C_{25}H_{26}FN_5O_3$ (463.51), MS (ESI): 464 (M+H⁺).

EXAMPLE VII 2-(4-Fluorophenyl)-5-methyl4-[cis-3-(2-nitrobenzyloxy)cyclohexyloxymethyl]oxazole

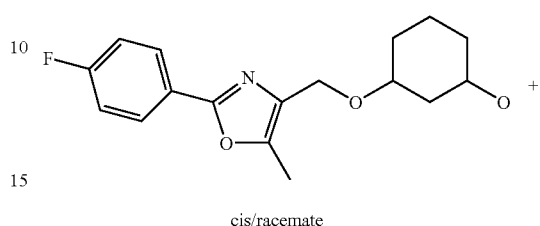

cis/racemate

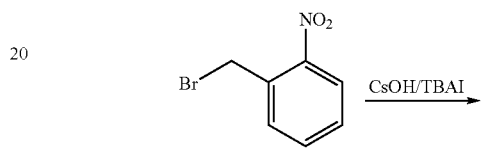

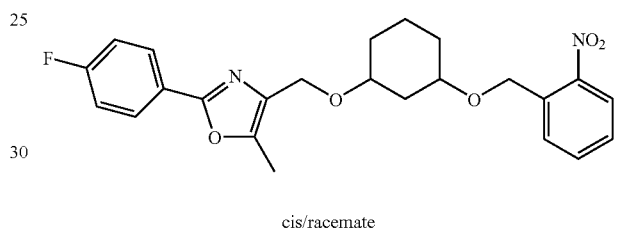

cis/racemate 0.1 g of 3-[2-(4-fluorophenyl)-5-methyloxazol-4-ylmethoxy]cyclohexanol is dissolved in 3 ml of acetonitrile, and 0.21 g of 2-nitrobenzyl bromide and 0.36 g of tetrabutylammonium iodide are added. 0.57 ml of cesium hydroxide solution (50% strength solution in water) is added dropwise, and the two-phase mixture is stirred vigorously at room temperature, for 12 hours. The reaction is checked (LCMS), showing the formation of the desired product, in addition to unreacted alcohol 3-[2-(4-fluorophenyl)-5-methyloxazol4-ylmethoxy]cyclohexanol. By addition of a further 0.2 g of 2-nitrobenzyl bromide (2 eq) at room temperature and stirring at room temperature for a further 12 hours, the reaction is terminated by addition of 2 ml of 1N hydrochloric acid and the mixture is extracted with ethyl acetate (2×10 ml). The combined organic phases are washed with saturated sodium chloride solution and dried over magnesium sulfate. Purification by HPLC gives 0.05 g of the compound 2-(4-fluorophenyl)-5-methyl4-[cis-3-(2-nitrobenzyloxy)cyclohexyloxymethyl]oxazole as a clear colorless oil.

$C_{24}H_{25}FN_2O_5$ (440.47), MS (ESI): 441 (M+H⁺).

EXAMPLE VIII 2-(4-Fluorophenyl)-5-methyl4-[cis-3-(3-nitrobenzyloxy)cyclohexyloxy-methyl]oxazole Analogously to Example VII, 3-[2-(4-fluorophenyl)-5-methyloxazol-4-ylmethoxy]cyclohexanol and 3-nitrobenzyl bromide gave the compound 2-(4-fluorophenyl)-5-methyl4-[cis-3-(3-nitrobenzyloxy)cyclohexyloxy-methyl]oxazole below:

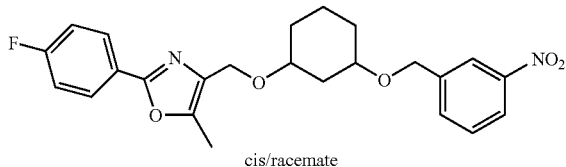

cis/racemate $C_{24}H_{25}FN_2O_5$ (440.47), MS (ESI): 441

EXAMPLE IX 2-(4-Fluorophenyl)-5-methyl4-[cis-3-(4-nitrobenzyloxy)cyclohexyloxy-methyl]oxazole Analogously to Example VII, 3-[2-(4-fluorophenyl)-5-methyloxazol-4-ylmethoxy]cyclohexanol and 4-nitrobenzyl bromide gave the compound 2-(4-fluorophenyl)-5-methyl4-[cis-3-(4-nitrobenzyloxy)cyclohexyloxy-methyl]oxazole below:

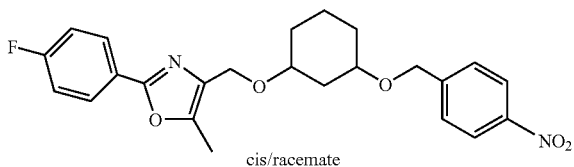

cis/racemate $C_{24}H_{25}FN_2O_5$ (440.47), MS (ESI): 441

EXAMPLE X 2-(4-Fluorophenyl )4-[cis-3-(2-methoxy-5-nitrobenzyloxy)cyclohexyloxy-methyl]-5-methyloxazole Analogously to Example VII, cis-3-[2-(4-fluorophenyl)-5-methyloxazol4-ylmethoxy]cyclohexanol and 2-methoxy-5-nitrobenzyl bromide gave the compound 2-(4-fluorophenyl)-4-[cis-3-(2-methoxy-5-nitrobenzyloxy)cyclohexyloxymethyl]-5-methyloxazole below:

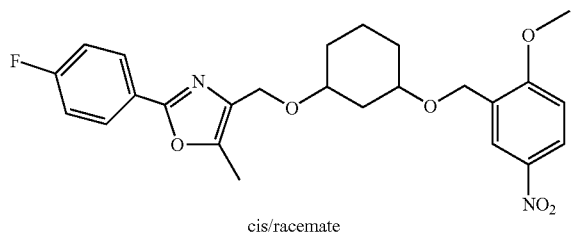

cis/racemate $C_{25}H_{27}FN_2O_6$ (470.50), MS (ESI): 471 (M+H⁺)

EXAMPLE XI cis-3-[2-(4-Fluorophenyl )-5-methyloxazol-4-yl methoxy]cyclohexyl 3,5-dinitrobenzoate

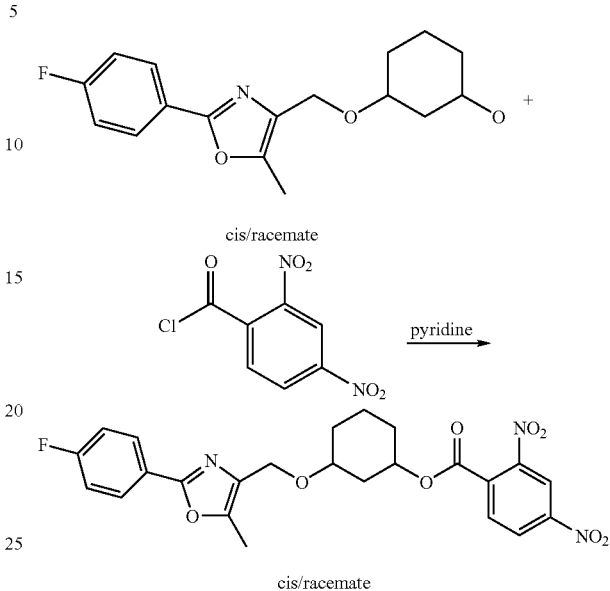

0.5 g of 3-[2-(4-fluorophenyl)-5-methyloxazol-4-ylmethoxy]cyclohexanol is dissolved in 3 ml of pyridine and, at 0° C., 0.6 g of 3,5-dinitrobenzoyl chloride is added. The reaction mixture is then heated at 50° C. for 10 minutes. The reaction is checked (LCMS) showing the formation of the desired product, in addition to unreacted alcohol cis-3-[2-(4-fluorophenyl)-5-methyloxazol-4-ylmethoxy]cyclohexanol. After a further 10 minutes of stirring at room temperature, the reaction is terminated by addition of 5 ml of concentrated hydrochloric acid, and the crude product is filtered off with suction, taken up in ethyl acetate, washed with saturated sodium bicarbonate and sodium chloride solution and dried over magnesium sulfate. Purification by HPLC gives 0.15 g of the compound cis-3-[2-(4-fluorophenyl )-5-methyloxazol4-ylmethoxy]cyclohexyl 3,5-dinitrobenzoate as yellow solid.

$C_{24}H_{22}FN_3O_8$ (499.46), MS (ESI): 500 (M+H⁺).

EXAMPLE XII cis-3-[2-(4-Fluorophenyl)-5-methyloxazol-4-ylmethoxy]cyclohexyl 3-methyl-5-nitrobenzoate Analogously to Example XI, cis-3-[2-(4-fluorophenyl)-5-methyloxazol-4-ylmethoxy]cyclohexanol and 3-methyl-5-nitrobenzoyl chloride gave the compound cis-3-[2-(4-fluorophenyl)-5-methyloxazol-4-ylmethoxy]cyclohexyl 3-methyl-5-nitrobenzoate below:

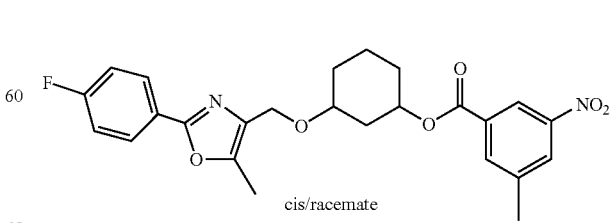

cis/racemate $C_{25}H_{25}FN_2O_6$ (468.48), MS (ESI): 469 (M+H⁺).

EXAMPLE XIII cis-3-[2-(4-Fluorophenyl)-5-methyloxazol-4-yl-methoxy]cyclohexyl 3-nitrobenzoate Analogously to Example XI, cis-3-[2-(4-fluorophenyl)-5-methyloxazol-4-ylmethoxy]cyclohexanol and 3-nitrobenzoyl chloride gave the compound cis-3-[2-(4-fluorophenyl)-5-methyloxazol-4-ylmethoxy]cyclohexyl 3-nitrobenzoate below:

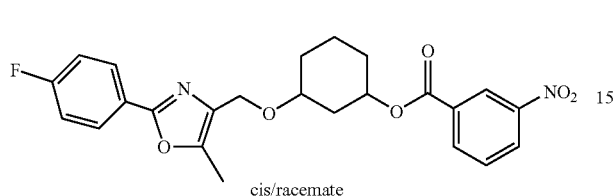

cis/racemate $C_{24}H_{23}FN_2O_6$ (454.46), MS (ESI): 455 (M+H$^+$).

EXAMPLE XIV cis-3-[2-(4-Fluorophenyl)-5-methyloxazol-4-yl-methoxy]cyclohexyl 2-nitrobenzoate Analogously to Example XI, cis-3-[2-(4-fluorophenyl)-5-methyloxazol-4-ylmethoxy]cyclohexanol and 2-nitrobenzoyl chloride gave the compound cis-3-[2-(4-fluorophenyl)-5-methyloxazol-4-ylmethoxy]cyclohexyl 2-nitrobenzoate below:

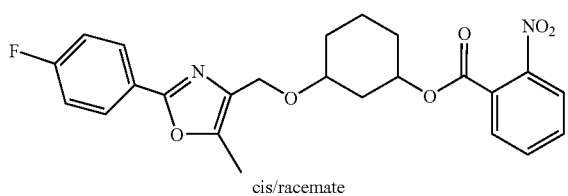

cis/racemate $C_{24}H_{23}FN_2O_6$ (454.46), MS (ESI): 455 (M+H$^+$).

EXAMPLE XV cis-3-[2-(4-Fluorophenyl)-5-methyloxazol-4-yl-methoxy]cyclohexyl 3-cyanobenzoate Analogously to Example XI, cis-3-[2-(4-fluorophenyl)-5-methyloxazol-4-ylmethoxy]cyclohexanol and 3-cyanobenzoyl chloride gave the compound cis-3-[2-(4-fluorophenyl)-5-methyloxazol-4-ylmethoxy]cyclohexyl 3-cyanobenzoate below:

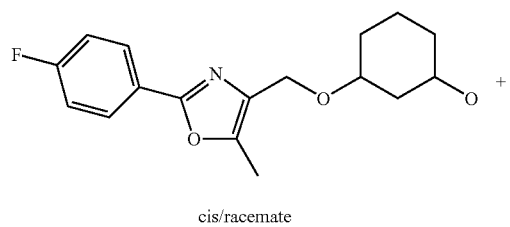

cis/racemate

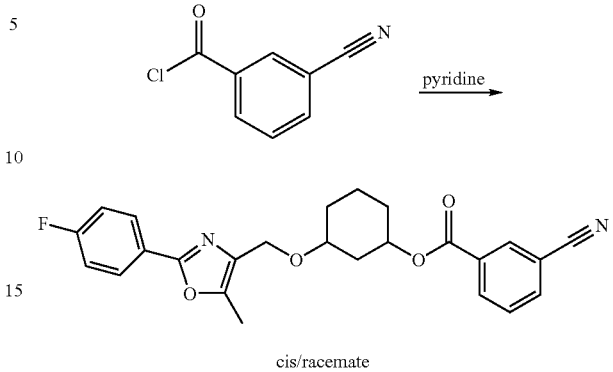

cis/racemate 0.1 g of 3-[2-(4-fluorophenyl)-5-methyloxazol-4-yl-methoxy]cyclohexanol is dissolved in 3 ml of pyridine and, at 0° C., 0.1 g of 3-cyanobenzoyl chloride is added. The reaction mixture is then heated at 50° C. for 10 minutes. The reaction is checked (LCMS), showing the formation of the desired product in addition to unreacted alcohol cis-3-[2-(4-fluorophenyl)-5-methyloxazol-4-ylmethoxy]cyclohexanol. After addition of a further 0.9 g of 3-cyanobenzoyl chloride and 30 minutes of stirring at room temperature, the reaction is terminated by addition of 5 ml of concentrated hydrochloric acid, the mixture is extracted with ethyl acetate and the organic phase is washed with saturated sodium bicarbonate and sodium chloride solution and dried over magnesium sulfate. Purification by HPLC gives 0.1 g of the compound cis-3-[2-(4-fluorophenyl)-5-methyloxazol-4-yl-methoxy]cyclohexyl 3-cyanobenzoate as a brown solid.

$C_{25}H_{23}FN_2O_4$ (434.47), MS (ESI): 435 (M+H$^+$).

EXAMPLE XVI cis-3-[2-(4-Fluorophenyl)-5-methyloxazol-4-yl-methoxy]cyclohexyl 4-cyanobenzoate Analogously to Example XI, cis-3-[2-(4-fluorophenyl)-5-methyloxazol-4-ylmethoxy]cyclohexanol and 4-cyanobenzoyl chloride gave the compound cis-3-[2-(4-fluorophenyl)-5-methyloxazol-4-ylmethoxy]cyclohexyl 4-cyanobenzoate below:

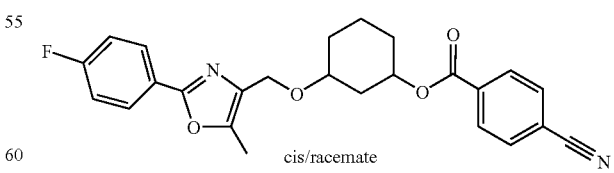

cis/racemate $C_{25}H_{23}FN_2O_4$ (434.47), MS (ESI): 435 (M+H$^+$).

The compounds synthesized in this manner (Examples XV–XVI) can be converted into the corresponding tetrazoles by reaction with tributyltin azide.

EXAMPLE XVII cis-3-[2-(4-Fluorophenyl)-5-methyloxazol-4-yl-methoxy]cyclohexyl 3-(1H-tetrazol-5-yl)benzoate

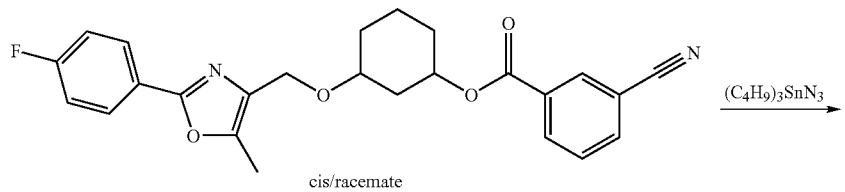

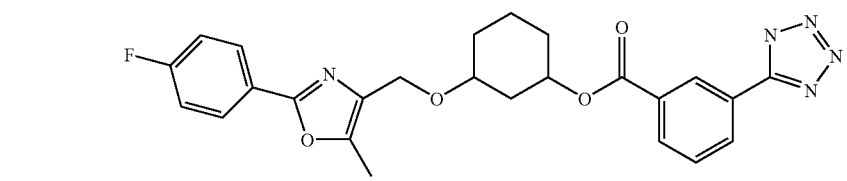

0.06 g of cis-3-[2-(4-fluorophenyl)-5-methyloxazol-4-yl-methoxy]cyclohexyl 3-cyanobenzoate is dissolved in 5 ml of xylene, 150 μm of tributyltin azide are added and the mixture is heated under reflux at 160° C. for 24 hours. The reaction is terminated by addition of 1 ml of trifluoroacetic acid (in 1 ml of methanol), 3 ml of water are added and the mixture is extracted with ethyl acetate (2×10 ml). The combined organic phases are washed with saturated sodium chloride solution and dried over magnesium sulfate, and the solvent is then removed under reduced pressure. Purification by preparative HPLC gives 0.04 g of the desired cis-3-[2-(4-fluorophenyl)-5-methyloxazol-4-ylmethoxy]cyclohexyl 3-(1H-tetrazol-5-yl)benzoate as an amorphous solid.

$C_{25}H_{24}FN_5O_4$ (477.49), MS (ESI): 478 (M+H$^+$).

EXAMPLE XVIII cis-3-[2-(4-Fluorophenyl)-5-methyloxazol-4-yl-methoxy]cyclohexyl 4-cyanobenzoate Analogously to Example XVII, cis-3-[2-(4-fluorophenyl)-5-methyloxazol-4-ylmethoxy]cyclohexyl 4-cyanobenzoate and tributyltin hydride gave cis-3-[2-(4-fluorophenyl)-5-methyloxazol-4-ylmethoxy]cyclohexyl 4-cyanobenzoate:

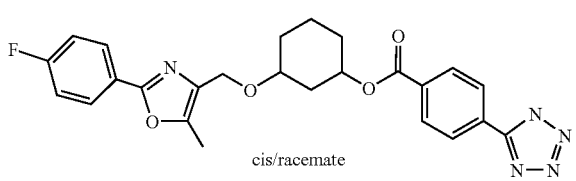

$C_{25}H_{24}FN_5O_4$ (477.49), MS (ESI): 478 (M+H$^+$).

EXAMPLE XIX cis-3-[2-(4-Fluorophenyl)-5-methyloxazol-4-yl-methoxy]cyclohexyl 4-methyl-3-nitrobenzene-sulfonate

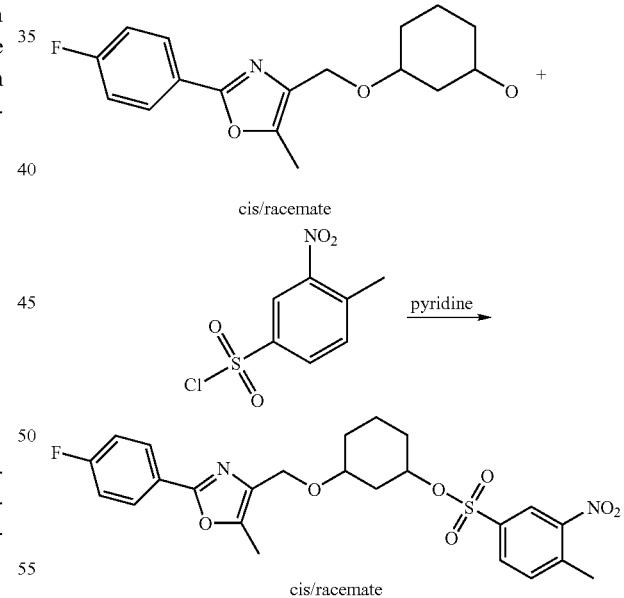

0.1 g of cis-3-[2-(4-fluorophenyl)-5-methyloxazol-4-yl-methoxy]cyclohexyl and 0.15 of 4-methyl-3-nitrobenzene-sulfonyl chloride are dissolved in 10 ml of dry chloroform and, at 0° C., 2 ml of pyridine are added. The reaction mixture is then stirred at room temperature for 12 hours. The reaction is checked (LCMS), showing the formation of the desired product, in addition to unreacted alcohol cis-3-[2-(4-fluorophenyl)-5-methyloxazol-4-ylmethoxy]cyclohex-anol. After a further 10 minutes of stirring at room temperature, the reaction is terminated by addition of 2 ml of concentrated hydrochloric acid, the mixture is extracted with dichloromethane and the extract is washed with saturated sodium bicarbonate and sodium chloride solution and dried over magnesium sulfate. Purification by HPLC gives 0.14 g of the compound cis-3-[2-(4-fluorophenyl)-5-methyloxazol-4-ylmethoxy]cyclohexyl 4-methyl-3-nitrobenzenesulfonate as a viscous oil $C_{24}H_{25}FN_2O_7S$ (504.53), MS (ESI): 505 (M+H$^+$).

EXAMPLE XX cis-3-[2-(4-Fluorophenyl )-5-methyloxazol-4-yl-methoxy]cyclohexyl 2-chloro-5-nitrobenzoate Analogously to Example XIX, cis-3-[2-(4-fluorophenyl)-5-methyloxazol-4-ylmethoxy]cyclohexyl and 2-chloro-5-nitrobenzenesulfonic acid gave the compound cis-3-[2-(4-fluorophenyl)-5-methyloxazol-4-ylmethoxy]cyclohexyl 2-chloro-5-nitrobenzenesulfonate:

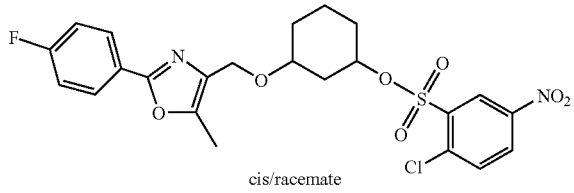

cis/racemate $C_{23}H_{22}FClN_2O_7S$ (524.95), MS (ESI): 525 (M+H$^+$).

EXAMPLE XXI cis-3-[2-(4-Fluorophenyl)-5-methyloxazol-4-yl-methoxy]cyclohexyl 4-methoxy-2-nitrobenzenesulfonate Analogously to Example XIX, cis-3-[2-(4-fluorophenyl)-5-methyloxazol-4-ylmethoxy]cyclohexanol and 4-methoxy-2-nitrobenzenesulfonic acid gave cis-3-[2-(4-fluorophenyl)-5-methyloxazol-4-ylmethoxy]cyclohexyl 4-methoxy-2-nitrobenzenesulfonate;

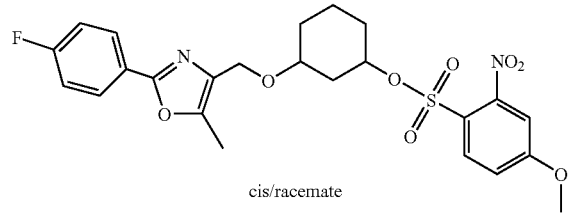

cis/racemate $C_{24}H_{25}FN_2O_8S$ (520.53), MS (ESI): 521 (M+H$^+$)

EXAMPLE XXII 5-(2-{cis-3-[2-(4-Fluorophenyl)-5-methyloxazol-4-ylmethoxy]cyclohexyloxy}-ethylidene)thiazolidine-2,4-dione 4-(cis-3-allyloxycyclohexyloxymethyl)-2-(4-fluorophenyl)-5-methyloxazole

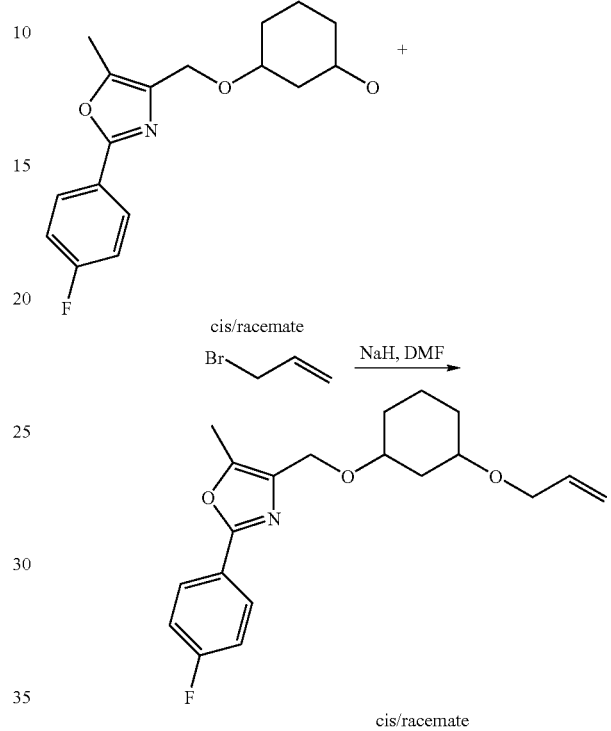

2 g of cis-3-[2-(4-fluorophenyl)-5-methyloxazol-4-ylmethoxy]cyclohexanol are dissolved in 15 ml of dimethylformamide, and 0.3 g of sodium hydride is added. After 30 minutes, 2.4 g of allyl bromide are added dropwise. The mixture is stirred at room temperature for 5 hours. 15 ml of 1N hydrochloric acid are then added to the reaction mixture, and the mixture is washed three times with 15 ml of ethyl acetate. The organic phase is dried over magnesium sulfate and the solvent is then removed under reduced pressure. The residue is purified by RP-HPLC. This gives 2.4 g of 4-(cis-3-allyloxycyclohexyloxymethyl)-2-(4-fluorophenyl)-5-methyloxazole as a yellowish oil. $C_{20}H_{24}FNO_3$ (345.42), MS (ESI): 346 (M+H$^+$)

[cis-3-[2-(4-Fluorophenyl)-5-methyloxazol-4-yl-methoxy]cyclohexyl]acetaldehyde

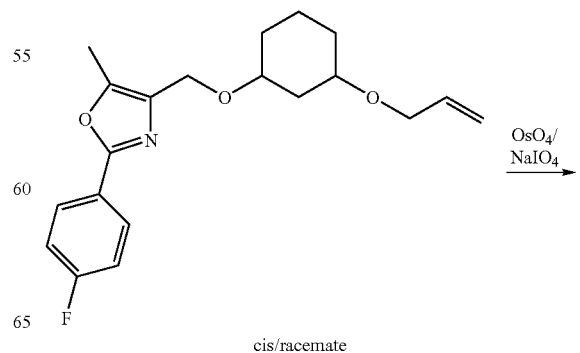

-continued

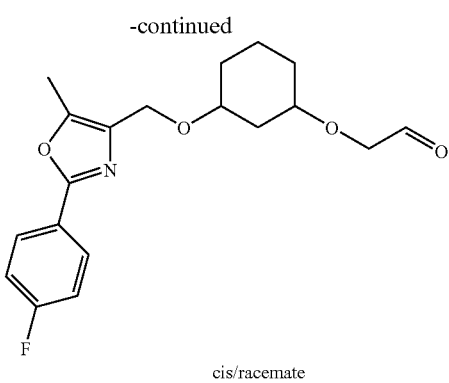

cis/racemate 2.0 g of 4-(cis-3-allyloxycyclohexyloxymethyl)-2-(4-fluorophenyl)-5-methyl-oxazole are dissolved in 50 ml of diethyl ether, and 3.8 g of sodium periodate, dissolved in 50 ml of water, are added. At 0° C., 1 ml of an osmium tetroxide solution (2.5% by weight in tert-butanol) is added, and the mixture is stirred vigorously at room temperature. After 8 hours, 100 ml of methyl tert-butyl ether are added, and the mixture is washed with a saturated sodium thiosulfate solution. The organic phase is dried over magnesium sulfate and the solvent is removed under reduced pressure. The residue is purified on silica gel (n-heptane:ethyl acetate=1:1→1:5). This gives 1.4 g of [cis-3-[2-(4-fluorophenyl)-5-methyloxazol-4-ylmethoxy]cyclohexyl]acetaldehyde as a colorless oil. $C_{20}H_{25}NO_4$ (343.42), MS (ESI): 344 (M+H$^+$), $R_f$(n-heptane:ethylacetate=1:1)=0.25.

5-(2-{cis-3-[2-(4-Fluorophenyl)-5-methyloxazol-4-ylmethoxy]cyclohexyloxy}-ethylidene)thiazolidine-2,4-dione

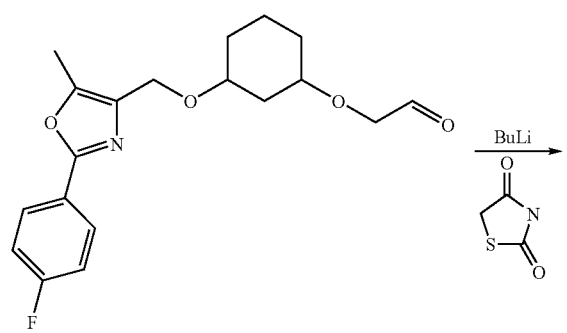

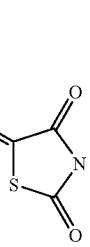

66 mg of thiazolidinedione are dissolved in 10 ml of tetrahydrofuran and, at −78° C., 0.11 ml of a 2.7 M solution of n-butyllithium in n-hexane is added. The mixture is stirred at −78° C. for 30 minutes, and 150 mg of [cis-3-[2-(4-fluorophenyl)-5-methyloxazol-4-ylmethoxy]cyclohexyl]acetaldehyde, dissolved in 5 ml of tetrahydrofuran, are then added. After 30 minutes of stirring at −78° C., the mixture is allowed to warm to room temperature. 5 ml of 1N hydrochloric acid are added, and the mixture is extracted three times with in each case 20 ml of ethyl acetate. The combined organic phases are dried over magnesium sulfate and the solvent is then removed under reduced pressure. The residue is purified by RP-HPLC. This gives 184 mg of 5-(2-{cis-3-[2-(4-fluorophenyl)-5-methyloxazol-4-ylmethoxy]cyclohexyl-oxy}ethylidene)thiazolidine-2,4-dione as a white solid. $C_{22}H_{23}FN_2O_5S$ (446.01), MS (ESI): 447 (M+H$^+$).

EXAMPLE XXIII

5-[2-[3-(5-Methyl-2-tolyloxazol-4-ylmethoxy)cyclohexyloxy]ethylidene]-thiazolidine-2,4-dione Analogously to Example XXII, [cis-3-(5-methyl-2-m-tolyloxazol-4-ylmethoxy)cyclohexyl]acetaldehyde and thiazolidinedione gave the compound 5-[2-[cis-3-(5-methyl-2-tolyloxazol-4-ylmethoxy)cyclohexyloxy}-ethylidene]thiazolidine-2,4-dione:

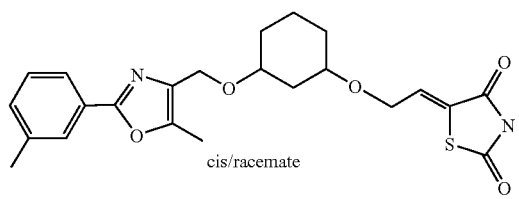

cis/racemate $C_{23}H_{26}N_2O_5S$ (442.53), MS (ESI): 443 (M+H$^+$).

EXAMPLE XXIV

5-[2-{cis-3-[2-(4-Fluorophenyl)-5-methyloxazol-4-ylmethoxy]cyclohexyloxy}-ethylidene]imidazolidine-2,4-dione Analogously to Example XXII, [3-[2-(4-fluorophenyl)-5-methyloxazol-4-ylmethoxy]cyclohexyl]acetaldehyde and hydantoin gave the compound 5-[2-{cis-3-[2-(4-fluorophenyl)-5-methyloxazol-4-ylmethoxy]cyclohexyloxy}-ethylidene]imidazolidine-2,4-dione:

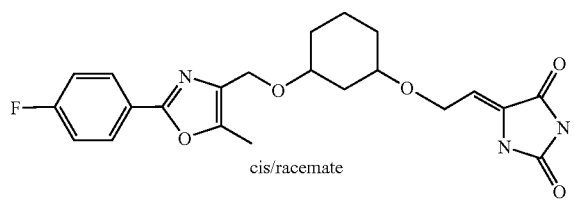

cis/racemate $C_{22}H_{24}FN_3O_5$ (429.45), MS (ESI): 430 (M+H$^+$)

EXAMPLE XXV

5-[2-{cis-3-[2-(4-Fluorophenyl)-5-methyloxazol-4-ylmethoxy]cyclohexyloxy}-ethylidene]-2-thioxoimidazolidine-2,4-dione Analogously to Example XXII, [cis-3-[2-(4-fluorophenyl)-5-methyloxazol-4-ylmethoxy]cyclohexyl]acetaldehyde and 2-thioxoimidazolidin-4-one gave 5-[2-{cis-3-[2-(4-fluorophenyl)-5-methyloxazol-4-ylmethoxy)cyclohexyloxy}-ethylidene)-2-thioxoimidazolidine-4-one:

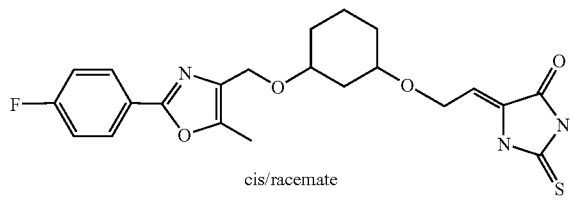

cis/racemate $C_{22}H_{24}FN_3O_4S$ (445.51), MS (ESI): 446 (M+H$^+$)

EXAMPLE XXVI 5-(2-{cis-3-[2-(4-Fluorophenyl)-5-methyloxazol-4-ylmethoxy]cyclohexyloxy}-ethyl)thiazolidine-2,4-dione Hydrogenation of the compound 5-(2-{cis-3-[2-(4-fluorophenyl)-5-methyloxazol-4-ylmethoxy]cyclohexyloxy}ethylidene)thiazolidine-2,4-dione, mentioned in Example Example XXII, with hydrogen gives the compound 5-(2-{cis-3-[2-(4-fluorophenyl)-5-methyloxazol-4-ylmethoxy]cyclohexyl-oxy}ethyl)thiazolidine-2,4-dione:

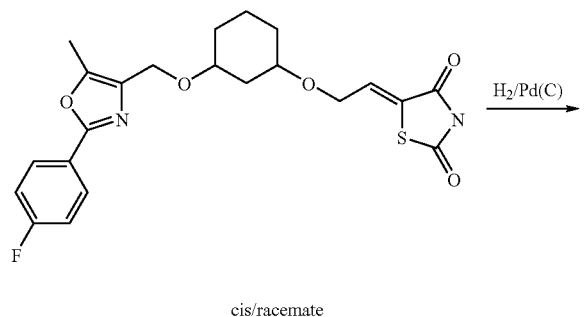

cis/racemate 180 mg of the unsaturated 5-(2-{cis-3-[2-(4-fluorophenyl)-5-methyloxazol-4-ylmethoxy]cyclohexyloxy}ethylidene)thiazolidine-2,4-dione is dissolved in 10 ml of ethyl acetate, and 20 mg of palladuium-on-carbon are added. The mixture is then stirred at room temperature under a hydrogen pressure of 2 bar for 2 hours. The catalyst is filtered off, the solvent is removed under reduced pressure and the residue is purified by RP-HPLC. This gives 140 mg of the compound 5-(2-{cis-3-[2-(4-fluorophenyl)-5-methyloxazol-4-ylmethoxy]cyclohexyloxy}ethyl)thiazolidine-2,4-dione as a yellowish solid.

$C_{22}H_{25}FN_2O_5S$ (448.01), MS (ESI): 449 (M+H$^+$)

EXAMPLE XXVII

5-{2-[(cis-3-(5-Methyl-2-tolyloxazol-4-ylmethoxy)cyclohexyloxy]ethyl}thiazolidine-2,4-dione As in Example XXVI, hydrogenation of the compound 5-[2-[cis-3-(5-methyl-2-tolyloxazol-4-ylmethoxy)cyclohexyloxy]ethylidene]thiazolidine-2,4-dione, mentioned in Example Example XXIII, with hydrogen gives the compound 5-{2-[(cis-3-(5-methyl-2-tolyloxazol-4-ylmethoxy)cyclohexyloxy]ethyl}thiazolidine-2,4-dione:

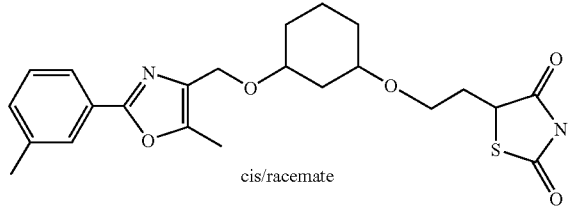

cis/racemate $C_{23}H_{28}N_2O_5S$ (444.55), MS (ESI): 445 (M+H$^+$)

EXAMPLE XXVIII

5-{2-[cis-3-(5-Methyl-2-m-tolyloxazol-4-ylmethoxy)cyclohexyl]ethyl}thiazol-idine-2,4-dione 4-(cis-3-Allylcyclohexyloxymethyl)-2-(3-methylphenyl)-5-methyloxazole

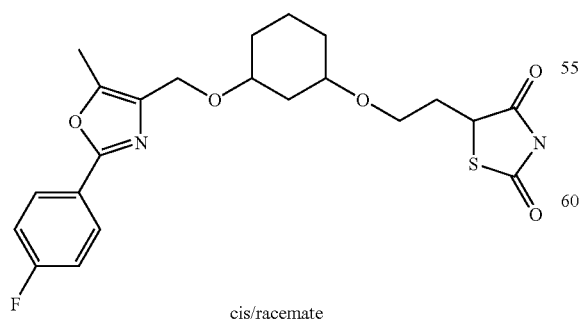

cis/racemate

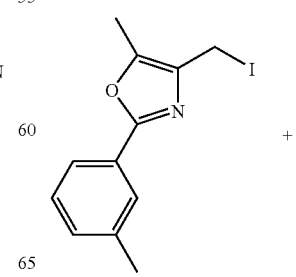

+

-continued

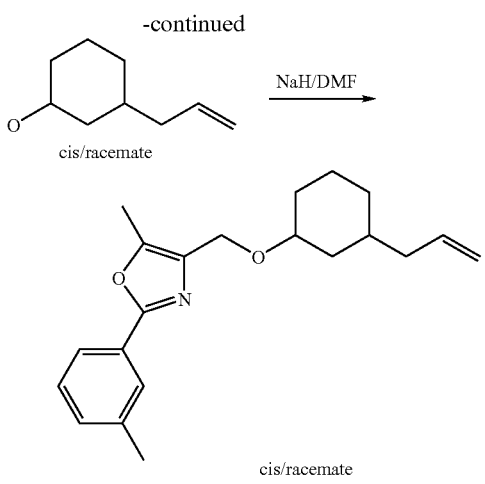

2 g of cis-3-allylcyclohexanol are dissolved in 30 ml of dimethylformamide, and 750 mg of sodium hydride (60% strength suspension in paraffin oil) are added. After 30 minutes, 6.7 g of 4-iodomethyl-5-methyl-2-(3-methylphenyl)oxazole, dissolved in 20 ml of dimethylformamide, are added dropwise. The mixture is stirred at room temperature for 1 hour. 200 ml of methy tert-buthyl ether are then added to the reaction mixture, and the mixture is washed three times with water. The organic phase is dried over magnesium sulfate and the solvent is then removed under reduced pressure. The residue is purified by RP-HPLC. This gives 1.56 g of 4-(cis-3-allylcyclohexyloxymethyl)-2-(3-methylphenyl)-5-methyloxazole as an oil. $C_{21}H_{27}NO_2$ (325.45), MS (ESI): 326 (M+H$^+$), $R_f$(n-heptane:ethylacetate=2:1)=0.28.

{cis-3-[2-(3-Methylphenyl)-5-methyloxazol-4-yl-methoxy]cyclohexyl}-acetaldehyde

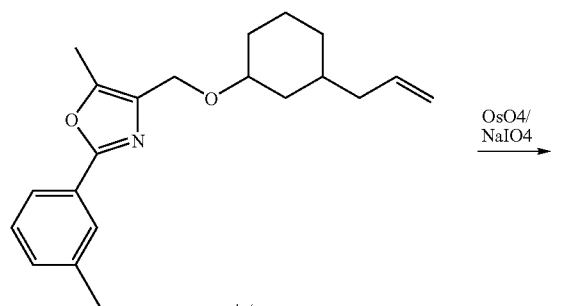

940 mg of 4-(cis-3-allylcyclohexyloxymethyl)-2-(3-methylphenyl)-5-methyloxazole are dissolved in 50 ml of diethyl ether, and 1.86 g of sodium periodate, dissolved in 50 ml of water, are added. At 0° C., 3 ml of an osmium tetroxide solution (2.5% by weight in tert-butanol) are added, and the mixture is stirred vigorously at room temperature. After 8 hours, 100 ml of methyl tert-butyl ether are added and the mixture is washed with a saturated sodium thiosulfate solution. The organic phase is dried over magnesium sulfate and the solvent is then removed under reduced pressure. The residue is purified on silica gel using the mobile phase n-heptane:ethyl acetate=4:1. This gives 270 mg of {cis-3-[2-(3-methylphenyl)-5-methyloxazol-4-ylmethoxy]cyclohexyl}acetaldehyde as a yellow-brown oil.

$C_{20}H_{25}NO_3$ (327.43), MS (ESI): 328 (M+H$^+$), $R_f$(n-heptane:ethylacetate=2:1)=0.07.

5-{1-Hydroxy-2-[cis-3-(5-methyl-2-m-tolyloxazol-4-ylmethoxy)cyclohexyl]-ethyl}thiazolidine-2,4-dione

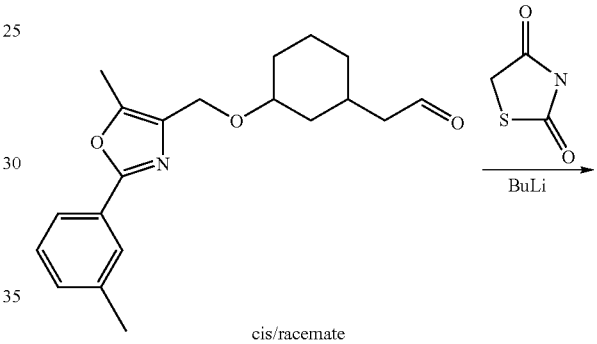

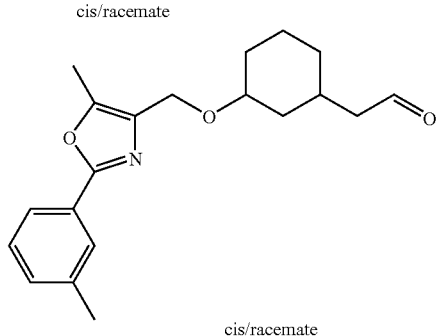

214 mg of thiazolidinedione are dissolved in 20 ml of tetrahydrofuran and, at −78° C., 1.4 ml of a 2.7 M solution of n-butyllithium in n-hexane are added. The mixture is stirred at −78° C. for 30 minutes, and 500 mg of {cis-3-[2-(3-methylphenyl)-5-methyloxazol-4-ylmethoxy]cyclohexyl}acetaldehyde, dissolved in 10 ml of tetrahydrofuran, are then added. After 30 minutes of stirring at −78° C., the mixture is allowed to warm to room temperature. 20 ml of 1N hydrochloric acid are added and the mixture is extracted three times with in each case 50 ml of ethyl acetate. The combined organic phases are dried over magnesium sulfate and the solvent is then removed under reduced pressure. The residue is purified by RP-HPLC. This gives 420 mg of 5-{1-hydroxy-2-[cis-3-(5-methyl-2-m-tolyloxazol-4-ylmethoxy)cyclohexyl]ethyl}thiazolidine-2,4-dione as a white solid. $C_{23}H_{28}N_2O_5S$ (444.45), MS (ESI): 445 (M+H$^+$)

EXAMPLE XXIX 5-(1-Hydroxy-2-{cis-3-[2-(3-methoxyphenyl)-5-methyloxazol-4-ylmethoxy]-cyclohexyl}ethyl)thiazolidine-2,4-dione Analogously to Example XXVIII, {cis-3-[2-(3-methylphenyl)-5-methyloxazol-4-ylmethoxy]cyclohexyl}acetaldehyde and thiazolididione give the compound 5-(1-hydroxy-2-{cis-3-[2-(3-methoxyphenyl)-5-methyloxazol-4-ylmethoxy]cyclohexyl}ethyl)thiazolidine-2,4-dione.

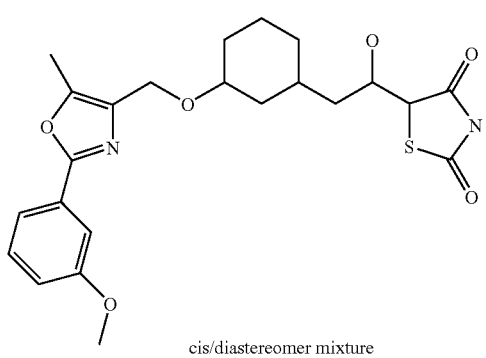

cis/diastereomer mixture $C_{23}H_{28}N_2O_6S$ (460.55), MS (ESI): 461 (M+H⁺).

EXAMPLE XXX

5-{1-Hydroxy-2-[cis-3-(5-methyl-p-tolyloxazol-4-ylmethoxy)-cyclohexyl]-ethyl}thiazolidine-2,4-dione Analogously to Example XXVIII, cis-[3-(5-methyl-2-p-tolyloxazol-4-ylmethoxy)cyclohexyl]acetaldehyde and thiazolididione gave the compound 5-{1-hydroxy-2-[cis-3-(5-methyl-2-p-tolyloxazol-4-ylmethoxy)cyclohexyl]-ethyl}thiazolidine-2,4-dione.

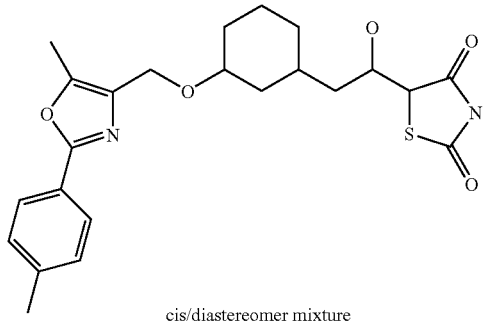

cis/diastereomer mixture $C_{23}H_{28}N_2O_5S$ (444.55), MS (ESI): 445 (M+H⁺).

EXAMPLE XXXI

5-{2-[cis-3-(5-Methyl-2-m-tolyloxazol-4-ylmethoxy)cyclohexyl]ethyl}-thiazolidine-2,4-dione

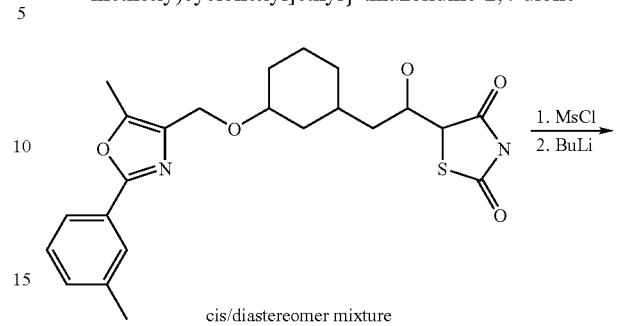

cis/diastereomer mixture

1. MsCl
2. BuLi
→

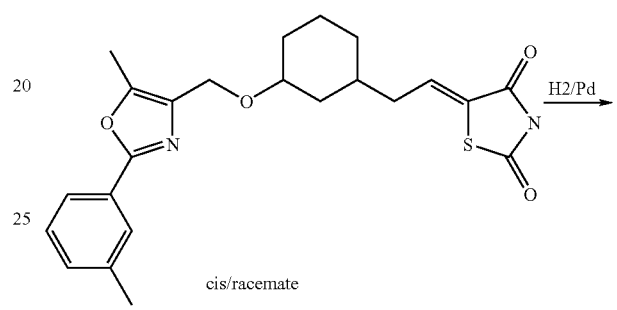

cis/racemate

H2/Pd
→

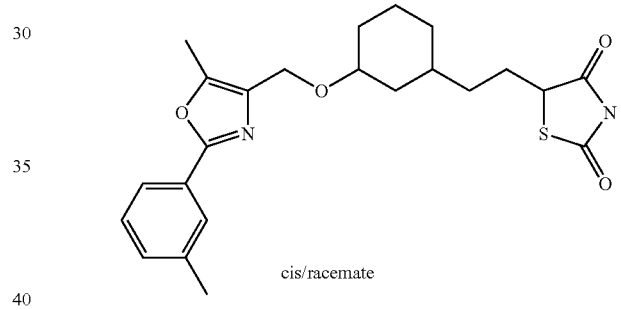

cis/racemate

5-{2-[cis-3-(5-Methyl-2-m-tolyloxazol-4-ylmethoxy)cyclohexyl]ethylidene}-thiazolidine-2,4-dione.

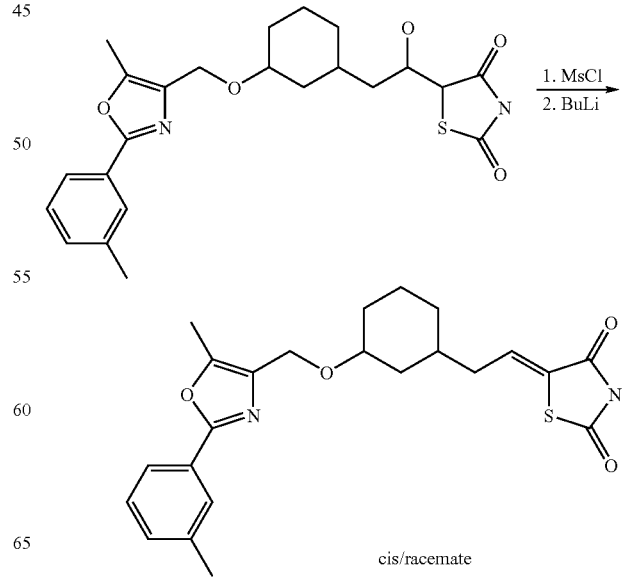

1. MsCl
2. BuLi
→ cis/racemate 344 mg of 5-{1-hydroxy-2-[cis-3-(5-methyl-2-m-tolyloxazol-4-ylmethoxy)cyclohexyl]ethyl}thiazolidine-2,4-dione are dissolved in 20 ml of dichloromethane, and 0.13 ml of triethylamine and and 0.12 ml of mesyl chloride are added. The mixture is stirred at room temperature for two hours, and another 0.13 ml of triethylamine and and 0.12 ml of mesyl chloride are added. The mixture is stirred at room temperature for 12 hours. 100 ml of dichloromethane are added, the mixture is washed with saturated sodium bicarbonate solution and dried over magnesium sulfate and the solvent is then removed under reduced pressure. The resulting residue is dissolved in 10 ml of tetrahydrofuran and, at −78° C., 0.22 ml of a 2.7 M solution of n-butyllithium in n-hexane is added. The mixture is stirred at 0° C. for 30 minutes, 20 ml of 1N hydrochloric acid are then added and the mixture is extracted three times with in each case 50 ml of ethyl acetate. The combined organic phases are dried over magnesium sulfate and the solvent is then removed under reduced pressure. The residue is purified by RP-HPLC. This gives 81 mg of 5-{2-[Cis-3-(5-methyl-2-m-tolyloxazol-4-ylmethoxy)cyclohexyl]ethylidene}thiazolidine-2,4-dione as a white solid.

$C_{23}H_{26}N_2O_4S$ (426.54), MS (ESI): 427 (M+H$^+$).

5-{2-[cis-3-(5-Methyl-2-m-tolyloxazol-4-yl-methoxy)cyclohexyl]ethyl}-thiazolidine-2,4-dione

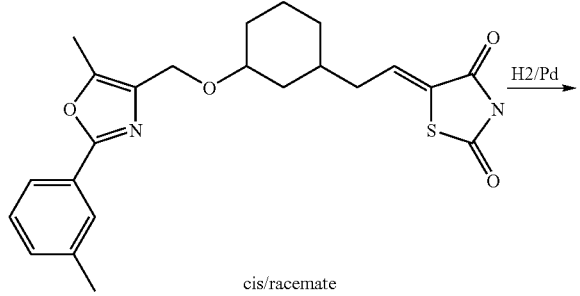

cis/racemate

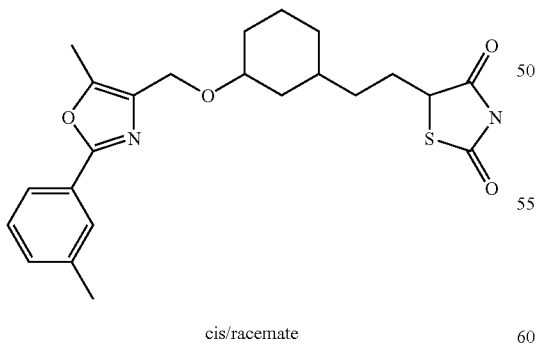

cis/racemate 81 mg of 5-{2-[cis-3-(5-methyl-2-m-tolyloxazol-4-yl-methoxy)cyclohexyl]-ethylidene}thiazolidine-2,4-dione are dissolved in 10 ml of ethyl acetate, and 10 mg of palladium (10% on activated carbon) are added. The mixture is stirred under an atmosphere of hydrogen (5 bar) for 9 hours. The catalyst is then filtered off through Celite and the filtrate is concentrated under reduced pressure. The residue is purified by RP-HPLC. This gives 60 mg of 5-{2-[cis-3-(5-methyl-2-m-tolyloxazol-4-ylmethoxy)cyclohexyl]-ethyl}thiazolidine-2,4-dione as a lyophilisate.

$C_{23}H_{28}N_2O_4S$ (428.55), MS (ESI): 429 (M+H$^+$).

EXAMPLE XXXII 5-(2-{cis-3-[2-(3-Methoxyphenyl)-5-methyloxazol-4-ylmethoxy]cyclohexyl}-ethyl)thiazolidine-2,4-dione Analogously to Example XXXI, 5-(1-hydroxy-2-{cis-3-[2-(3-methoxyphenyl)-5-methyloxazol-4-ylmethoxy]cyclohexyl}ethyl)thiazolidine-2,4-dione gave the compound 5-(2-{cis-3-[2-(3-methoxyphenyl)-5-methyloxazol-4-ylmethoxy]cyclohexyl}ethyl)thiazolidine-2,4-dione

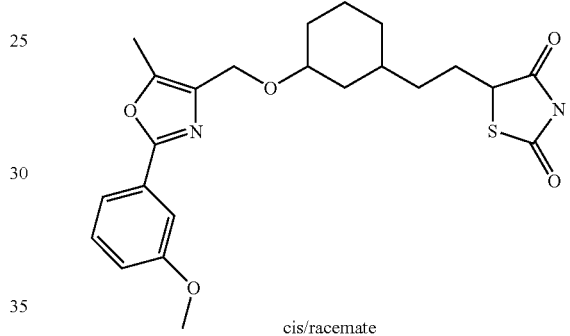

cis/racemate $C_{23}H_{28}N_2O_5S$ (444.55), MS (ESI): 445 (M+H$^+$).

EXAMPLE XXXIII

5-{2-[cis-3-(5-Methyl-2-p-tolyloxazol-4-ylmethoxy)cyclohexyl]ethyl}-thiazolidine-2,4-dione Analogously to Example XXXI, 5-{1-hydroxy-2-[cis-3-(5-methyl-2-p-tolyloxazol-4-ylmethoxy)cyclohexyl]ethyl}thiazolidine-2,4-dione gave the compound 5-{2-[cis-3-(5-methyl-2-p-tolyloxazol-4-ylmethoxy)cyclohexyl]ethyl}thiazolidine-2,4-dione.

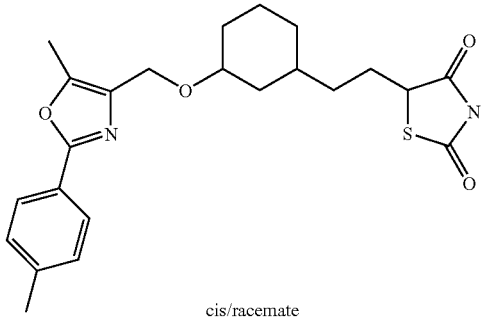

cis/racemate $C_{23}H_{28}N_2O_4S$ (428.55), MS (ESI): 429 (M+H$^+$).

EXAMPLE XXXIV

5-[1-[cis-3-(5-Methyl-2-tolyloxazol-4-ylmethoxy)cyclohexyl]methylidene]-thiazolidine-2,4-dione

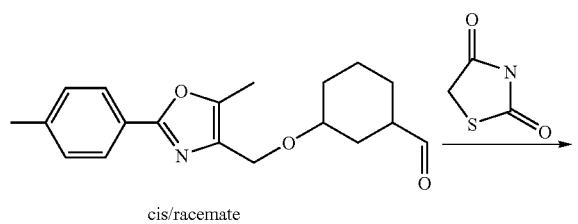
cis/racemate

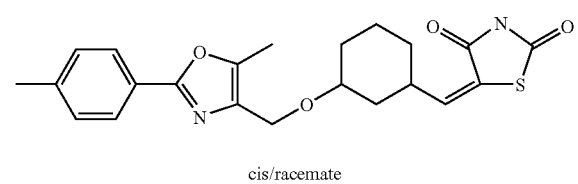
cis/racemate

↓ H₂/Pd(C)

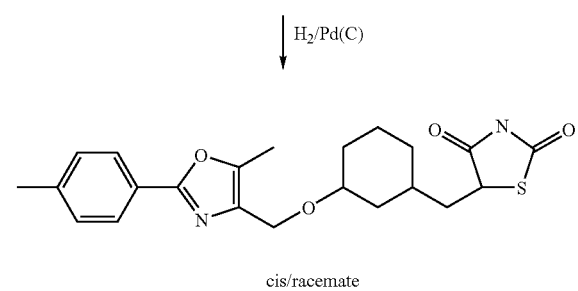
cis/racemate cis-3-Hydroxymethylcyclohexanol

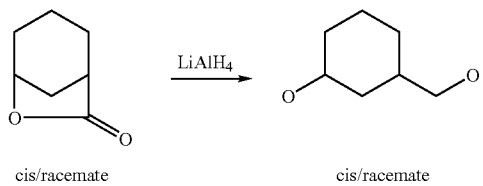
cis/racemate   cis/racemate 10 g of 6-oxabicyclo[3.2.1]octan-7-one are dissolved in 300 ml of tetrahydrofuran, and 160 ml of a 1 M solution of lithium aluminum hydride in tetrahydrofuran are added with ice-cooling. After 30 minutes of stirring at room temperature, a saturated ammonium chloride solution is added and the pH is adjusted to neutral by addition of a 5% strength citric acid solution. The tetrahydrofuran is removed under reduced pressure and the residue is extracted three times with in each case 150 ml of ethyl acetate. The combined organic phases are dried over magnesium sulfate and the solvent is then removed under reduced pressure. This gives 10.5 g of cis-3-hydroxymethylcyclohexanol as a colorless oil. $C_7H_{14}O_2$ (130.13), Rf(ethyl acetate)=0.14.

cis-3-(tert-Butyl-diphenyl-silanyloxymethyl)cyclohexanol

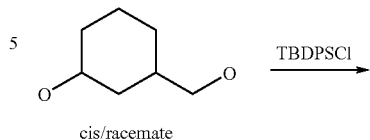
cis/racemate

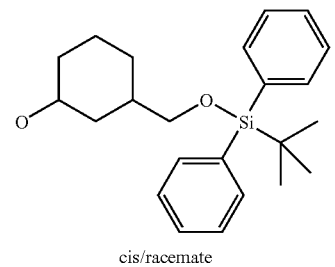
cis/racemate 10.5 g of cis-3-hydroxymethylcyclohexanol are dissolved in 300 ml of dimethylformamide, and 23 ml of tert-butyl-diphenyl-silanyl chloride, 8.0 g of imidazole and 200 mg of dimethylaminopyridine are added. The mixture is stirred at room temperature for 12 hours. The dimethylformamide is removed under reduced pressure and the residue is dissolved in 300 ml of ethyl acetate and washed five times with in each case 100 ml of water. The organic phase is dried over magnesium sulfate and the solvent is then removed under reduced pressure. This gives 27.0 g of cis-3-(tert-butyl-diphenyl-silanyloxymethyl)cyclohexanol as an oil. $C_{23}H_{32}O_2Si$ (368.6), Rf(n-heptane:ethyl acetate=1:1)=0.42.

cis-3-(tert-Butyl-diphenyl-silanyloxymethyl)cyclohexyloxymethyl]-5-methyl-2-p-tolyloxazole

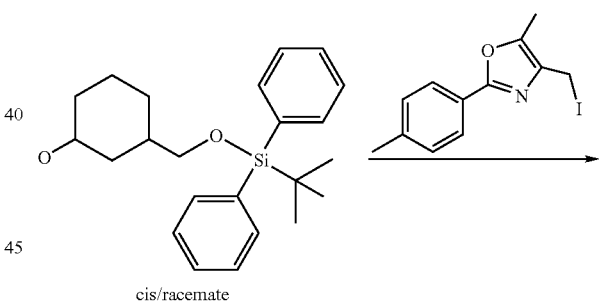
cis/racemate

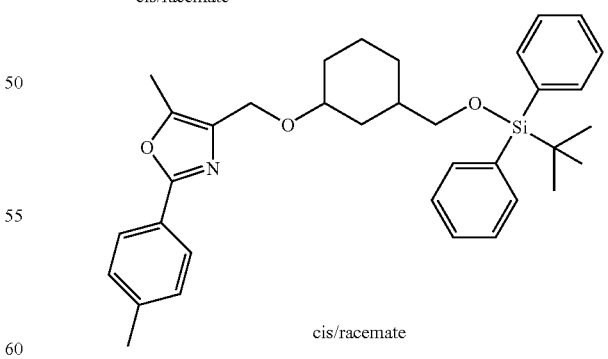
cis/racemate 6.4 g of cis-3-(tert-butyl-diphenyl-silanyloxymethyl)cyclohexanol and 6.5 g of 4-iodomethyl-5-methyl-2-p-tolyloxazole are dissolved in 200 ml of dimethylformamide, and 1 g of sodium hydride (60% strength suspension in mineral oil) is added. After 1 hour of stirring at room temperature, another 2 g of sodium hydride and 5 g of 4-iodomethyl-5- methyl-2-p-tolyloxazole are added. After 4 hours of stirring at room temperature, the reaction mixture is diluted by addition of 400 ml of ethyl acetate and washed five times with in each case 200 ml of water. The organic phase phase is dried over magnesium sulfate and the solvent is then removed under reduced pressure. The residue is purified on silica gel using the mobile phase n-heptane:ethyl acetate=10:1. This gives 6.8 g of 4-cis-3-(tert-butyl-diphenyl-silanyloxymethyl)cyclohexyloxymethyl]-5-methyl-2-p-tolyloxazole as an oil. $C_{35}H_{43}NO_3Si$ (553.28), Rf(n-heptane:ethyl acetate=2:1)=0.50.

[(cis-3-(5-Methyl-2-p-tolyloxazol-4-ylmethoxy)cyclohexyl]methanol

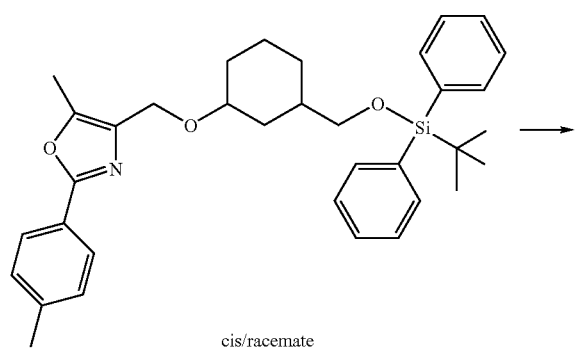

cis/racemate

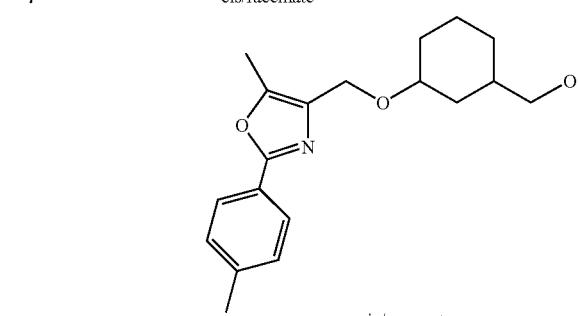

cis/racemate 6.8 g of 4-cis-3-(tert-butyl-diphenyl-silanyloxymethyl)cyclohexyloxymethyl]-5-methyl-2-p-tolyloxazole are dissolved in 40 ml of tetrahydrofuran, and 40 ml of a 1M solution of tetrabutylammonium fluoride are added. The mixture is heated at 50° C. for 1 hour and the solvent is then removed under reduced pressure and the resulting residue is purified on silica gel using the mobile phase n-heptane:ethyl acetate=5:1=>1:1. This gives 1.0 g of cis-3-(5-methyl-2-p-tolyloxazol-4-ylmethoxy)cyclohexyl]methanol as an oil. C19H25NO3 (315.42), Rf(n-heptane:ethyl acetate=1:1) =0.13.

cis-3-(5-Methyl-2-p-tolyloxazol-4-ylmethoxy)cyclohexanecarbaldehyde

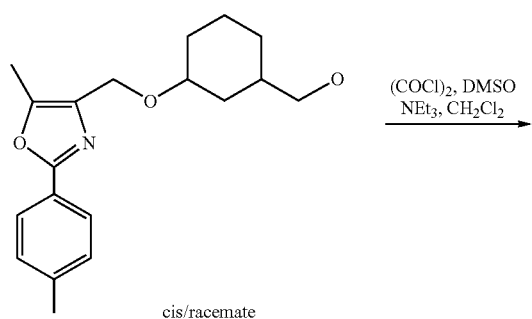

cis/racemate (COCl)₂, DMSO
NEt₃, CH₂Cl₂
→

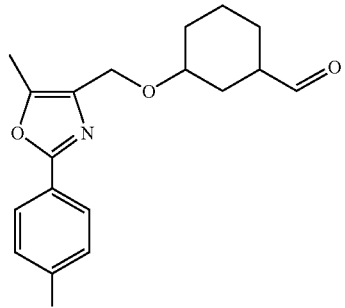

cis/racemate

At −78° C., 0.89 ml of DMSO in 1 ml of dichloromethane is added dropwise to 0.48 ml of oxalyl chloride in 15 ml of dichloromethane such that the temperature does not exceed −70° C. After the addition has ended, the solution is stirred at this temperature for 30 minutes. 1.5 g of cis-3-(5-methyl-2-p-tolyloxazol-4-ylmethoxy)cyclohexyl]methanol in 2 ml of dichloromethane are then added dropwise such that the temperature remains below −78° C. The solution is stirred at this temperature for 30 minutes. 3.2 ml of triethylamine are then added dropwise, the cooling bath is removed and the solution is warmed to 0° C. At this temperature, 10 ml of water are added and the mixture is stirred vigorously at room temperature. The aqueous phase is removed and extracted with dichloromethane. The combined organic phases are washed with saturated ammonium chloride solution, dried over magnesium sulfate and concentrated, which gives 1.50 g of cis-3-(5-methyl-2-p-tolyloxazol-4-ylmethoxy)cyclohexanecarbalde-hyde. $C_{19}H_{23}NO_3$ (313.40), LCMS (ESI): 314 (MH⁺).

5-[1-[cis-3-(5-Methyl-2-tolyloxazol-4-ylmethoxy)cyclohexyl]-methylidene]thiazolidine-2,4-dione

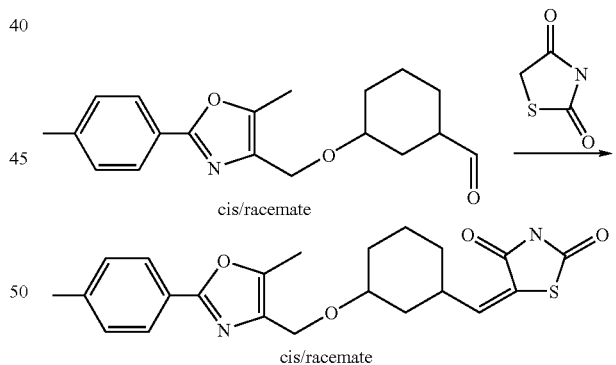

0.25 g of thiazolidinedione are initially charged in a three-necked flask, which had been dried by heating, dissolved in 15 ml of tetrahydrofuran and cooled to −78° C., and 2.4 ml of n-buthyllithium (1.6 M solution in n-hexane) are slowly added dropwise such that the internal temperature does not exceed −65° C. The solution is then warmed to room temperature, resulting in the color of the solution changing to yellow. The mixture is again cooled to −70° C., and 0.4 g of cis-3-(5-methyl-2-p-tolyloxazol-4-ylmethoxy) cyclohexanecarbaldehyde—dissolved in 5 ml of tetrahydrofuran—is then added dropwise, and the reaction mixture is warmed to room temperature. The tertiary alcohol is formed as an adduct (reaction control (TLC and LCMS) M=430 g/mol). Acidic work-up (5 ml 1 N HCl) and extraction with 2×10 ml of ethyl acetate gives the desired elimination product after removal of the solvent under reduced pressure. The crude product is taken up in acetonitrile and the mother liquor is filtered off, giving 0.5 g of 5-[1-[cis-3-(5-methyl-2-tolyloxazol-4-ylmethoxy)cyclohexyl]-methylidene]thiazolidine-2,4-dione as a white solid.

C$_{22}$H$_{24}$N$_2$O$_4$S (412.54), MS (ESI): 413 (M+H$^+$).

EXAMPLE XXXV

5-[cis-3-(5-Methyl-2-tolyloxazol-4-ylmethoxy)cyclohexylmethyl]thiazolidine-2,4-dione The compound 5-[1-[cis-3-(5-methyl-2-tolyloxazol-4-ylmethoxy)cyclohexyl]-methylidene]thiazolidine-2,4-dione, mentioned in Example XXXIV, is obtained by hydrogenation of the compound 5-[cis-3-(5-methyl-2-tolyloxazol-4-ylmethoxy)cyclohexylmethyl]thiazolidine-2,4-dione.

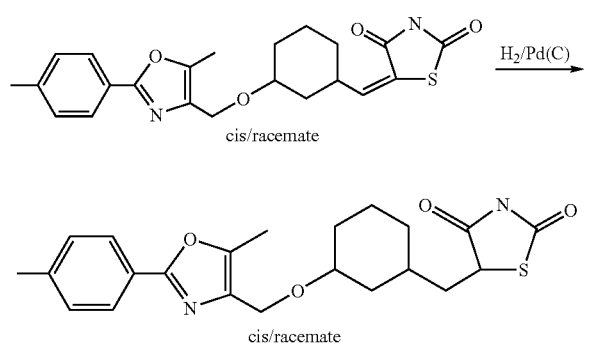

0.35 g of 5-[1-[cis-3-(5-methyl-2-tolyloxazol-4-ylmethoxy)cyclohexyl]-methylidene]thiazolidine-2,4-dione is dissolved in 12 ml of a solvent mixture of ethyl acetate and methanol (3:1), and 20 mg of palladium-on-carbon are added. The mixture is then hydrogenated at room temperature under a hydrogen pressure of 3 bar for 2 hours. The catalyst is filtered off and the solvent is then removed under reduced pressure and the residue is taken up in acetonitrile. The product can be filtered off, giving 0.3 g of 5-[cis-3-(5-methyl-2-tolyloxazol-4-ylmethoxy)cyclohexylmethyl]thiazolidine-2,4-dione as a white solid. C$_{22}$H$_{26}$N$_2$O$_4$S (414.52), MS (ESI): 415 (M+H$^+$).

EXAMPLE XXXVI 5-(2-{(cis-3-[5-cyclohexyl-2-(3-methoxyphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-cyclohexyl-2-(3-methoxyphenyl)oxazole gave the compound 5-(2-{(cis-3-[5-cyclohexyl-2-(3-methoxyphenyl)oxazol-4-ylmethoxy]cyclohexyl}ethyl)thiazolidine-2,4-dione.

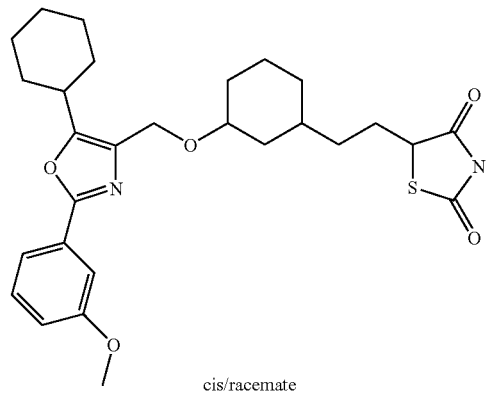

C28H36N2O5S (512.67), MS(ESI): 513 (M+H$^+$)

EXAMPLE XXXVII 5-(2-{(cis-3-[5-cyclohexyl-2-(4-methylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-cyclohexyl-2-(4-methylphenyl)oxazole gave the compound 5-(2-{(cis-3-[5-cyclohexyl-2-(4-methylphenyl)oxazol-4-ylmethoxy]-cyclohexyl}ethyl)thiazolidine-2,4-dione.

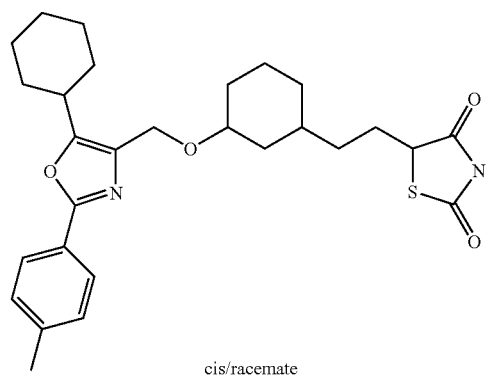

C28H36N2O4S (496.67), MS(ESI): 497 (M+H$^+$).

EXAMPLE XXXVIII 5-(2-{(cis-3-[5-ethyl-2-(3,5-bis-trifluoromethylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-ethyl-2-(3,5-bis-trifluoromethylphenyl)-oxazole gave the compound 5-(2-{(cis-3-[5-ethyl-2-(3,5-bis-trifluoromethylphenyl)oxazol-4-ylmethoxy]cyclohexyl}ethyl)thiazolidine-2,4-dione.

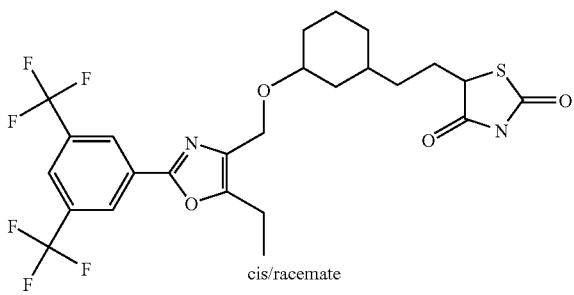

cis/racemate

C25H26F6N2O4S (564.55), MS(ESI): 565 (M+H⁺)

EXAMPLE XXXIX 5-(2-{(cis-3-[5-ethyl-2-(2,6-bis-dimethylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-ethyl-2-(2,6-dimethylphenyl)oxazole gave the compound 5-(2-{(cis-3-[5-ethyl-2-(2,6-dimethylphenyl)oxazol-4-ylmethoxy]cyclohexyl}ethyl)thiazolidine-2,4-dione.

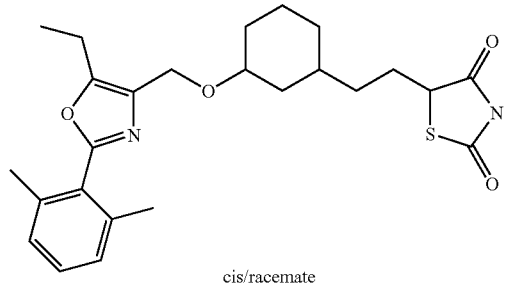

cis/racemate

C25H32N2O4S (456.64), MS(ESI): 457 (M+H⁺).

EXAMPLE XL 5-(2-{(cis-3-[5-methyl-2-(2-trifluoromethylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-methyl-2-(2-trifluoromethylphenyl)oxazole gave the compound 5-(2-{(cis-3-[5-methyl-2-(2-trifluoromethylphenyl)oxazol-4-ylmethoxy]cyclohexyl}ethyl)thiazolidine-2,4-dione.

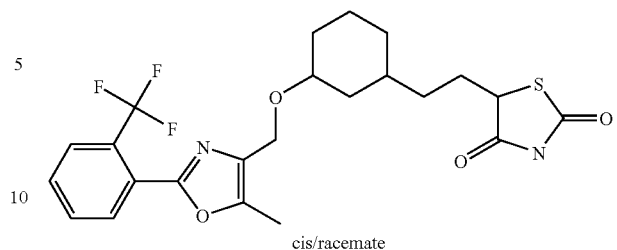

cis/racemate

C23H25F3N2O4S (482.53), MS(ESI): 483 (M+H⁺).

EXAMPLE XLI 5-(2-{(cis-3-[5-ethyl-2-(3-methoxyphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-ethyl-2-(3-methoxyphenyl)oxazole gave the compound 5-(2-{(cis-3-[5-ethyl-2-(3-methoxyphenyl)oxazol-4-ylmethoxy]cyclohexyl}ethyl)thiazolidine-2,4-dione.

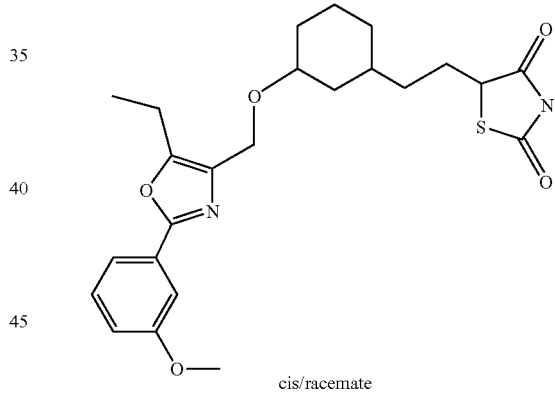

cis/racemate

C24H30N2O5S (458.58), MS(ESI): 459 (M+H⁺).

EXAMPLE XLII 5-(2-{(cis-3-[5-ethyl-2-(2-trifluoromethylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-ethyl-2-(2-trifluorophenyl)oxazole gave the compound 5-(2-{(cis-3-[5-ethyl-2-(2-trifluoromethylphenyl)oxazol-4-ylmethoxy]cyclohexyl}ethyl)thiazolidine-2,4-dione.

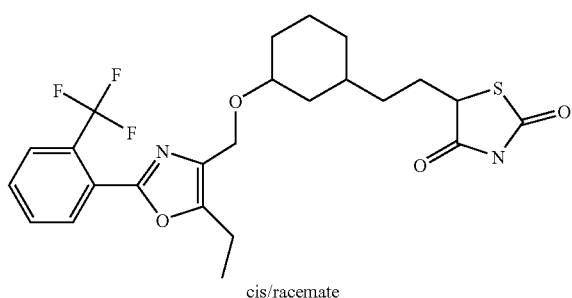

cis/racemate

C24H27F3N2O4S (496.55), MS(ESI): 497 (M+H⁺).

EXAMPLE XLIII

5-{2-[3-(5-ethyl-2-p-tolyloxazol-4-ylmethoxy]cyclohexyl}ethyl)thiazolidine-2,4-dione Analogously to Example XXVIII and Example XXXI, cis-3-allylcyclohexanol, thiazolidinedione and 4-iodomethyl-5-ethyl-2-(4-methylphenyl)oxazole gave the compound 5-{2-[cis-3-(5-ethyl-2-p-tolyloxazol-4-ylmethoxy)cyclohexyl]ethyl}-thiazolidine-2,4-dione.

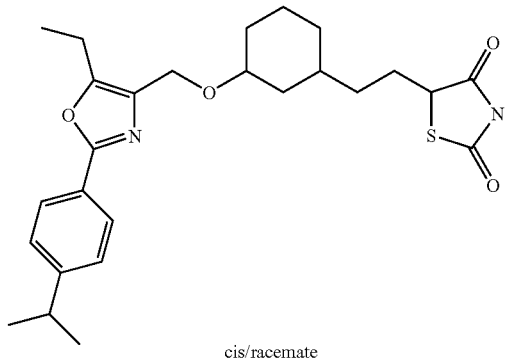

cis/racemate

C26H34N2O4S (470.64), MS(ESI): 471 (M+H⁺).

EXAMPLE XLV 5-(2-{(cis-3-[5-isopropyl-2-(4-methylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-ethyl-2-(4-isopropylphenyl)oxazole gave the compound 5-(2-{cis-3-[5-isopropyl-2-(4-methylphenyl)oxazol-4-ylmethoxy]cyclohexyl}ethyl)thiazolidine-2,4-dione.

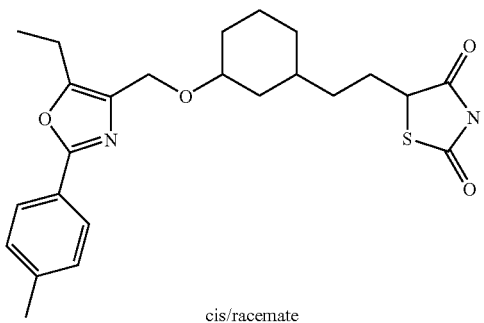

cis/racemate

C24H30N2O4S (442.58), MS(ESI): 443 (M+H⁺).

EXAMPLE XLIV 5-(2-{(cis-3-[5-ethyl-2-(4-isopropylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-ethyl-2-(4-isopropylphenyl)oxazole gave the compound 5-(2-{cis-3-[5-ethyl-2-(4-isopropylphenyl)oxazol-4-ylmethoxy]cyclohexyl}ethyl)thiazolidine-2,4-dione.

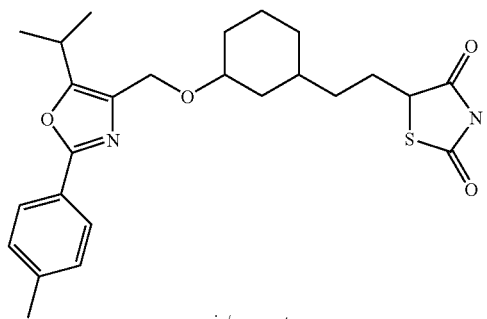

cis/racemate

C25H32N2O4S (456.61), MS(ESI): 457 (M+H⁺).

EXAMPLE XLVI 5-(2-{(cis-3-[5-methyl-2-(3-trifluoromethylphenyl)oxazol-4-ylmethoxy]-cyclohexyl}ethyl)thiazolidine-2,4-dione Analogously to Example XXVIII and Example XXXI, cis-3-allylcyclohexanol, thiazolidinedione and 4-iodomethyl-5-methyl-2-(3-trifluoromethylphenyl)oxazole gave the compound 5-(2-{(cis-3-[5-methyl-2-(3-trifluoromethylphenyl)oxazol-4-ylmethoxy]cyclohexyl}ethyl)thiazolidine-2,4-dione.

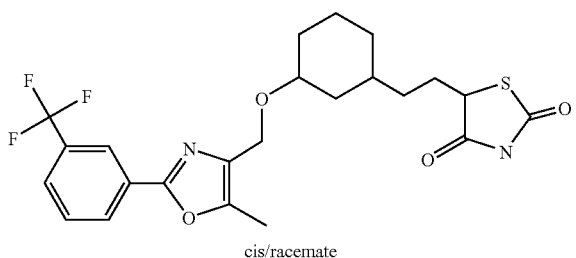

cis/racemate

C23H25F3N2O4S (482.53), MS(ESI): 483 (M+H⁺).

EXAMPLE XLVII

The compound 5-{2-[cis-3-(5-methyl-2-m-tolyloxazol-4-ylmethoxy)cyclohexyl]ethylidene}thiazolidine-2,4-dione from Example XXXI was separated by chromatography on a chiral phase into the compounds 5-{2-[(1S,3S)-3-(5-methyl-2-m-tolyloxazol-4-ylmethoxy)cyclohexyl]ethylidene}thiazolidine-2,4-dione and 5-{2-[(1R,3R)-3-(5-methyl-2-m-tolyloxazol-4-ylmethoxy)cyclohexyl]ethylidene}thiazolidine-2,4-dione.

5-{2-[(1R,3R)-3-(5-methyl-2-m-tolyloxazol-4-ylmethoxy)cyclohexyl]-ethylidene}thiazolidine-2,4-dione

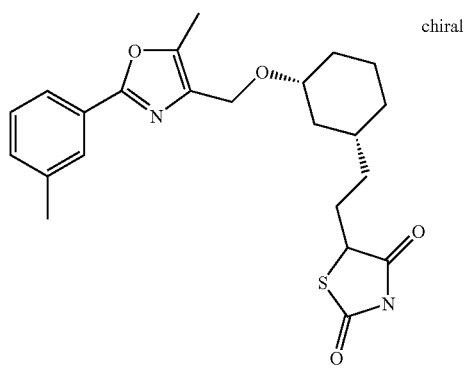

$C_{23}H_{28}N_2O_4S$ (428.55), MS(ESI): 429 (M+H⁺).

5-{2-[(1S,3S)-3-(5-methyl-2-m-tolyloxazol-4-ylmethoxy)cyclohexyl]-ethylidene}thiazolidine-2,4-dione

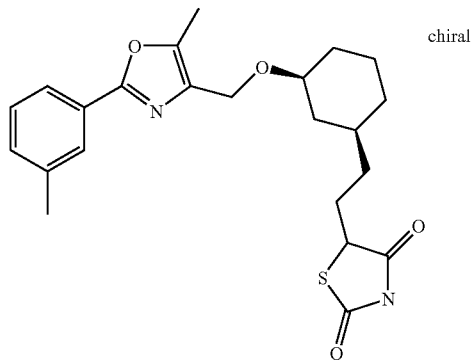

$C_{23}H_{28}N_2O_4S$ (428.55), MS(ESI): 429 (M+H⁺).

EXAMPLE XLVIII

The compound 5-(2-{cis-3-[5-ethyl-2-(4-isopropylphenyl)oxazol-4-ylmethoxy]cyclohexyl}ethyl)thiazolidine-2,4-dione from Example XLIV was separated by chromatography on a chiral phase into the compounds 5-(2-{(1s,3S)-3-[5-ethyl-2-(4-isopropylphenyl)oxazol-4-ylmethoxy]cyclohexyl}ethyl)thiazolidine-2,4-dione and 5-(2-{(1R,3R)-3-[5-ethyl-2-(4-isopropylphenyl)oxazol-4-ylmethoxy]cyclohexyl}ethyl)thiazolidine-2,4-dione.

5-(2-{(1s,3S)-3-[5-ethyl-2-(4-isopropylphenyl)oxazol-4-ylmethoxy]cyclohexyl}ethyl)thiazolidine-2,4-dione

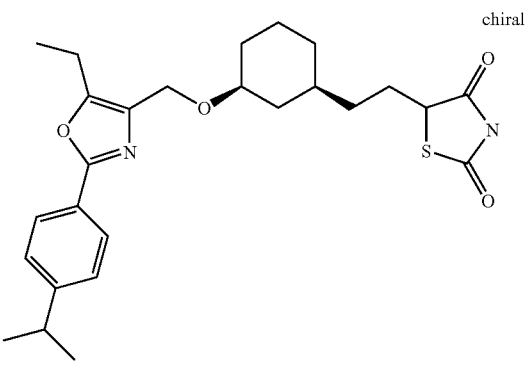

C26H34N2O4S (470.64), MS(ESI): 471 (M+H⁺).

5-(2-{(1R,3R)-3-[5-ethyl-2-(4-isopropylphenyl)oxazol-4-ylmethoxy]cyclohexyl}ethyl)thiazolidine-2,4-dione

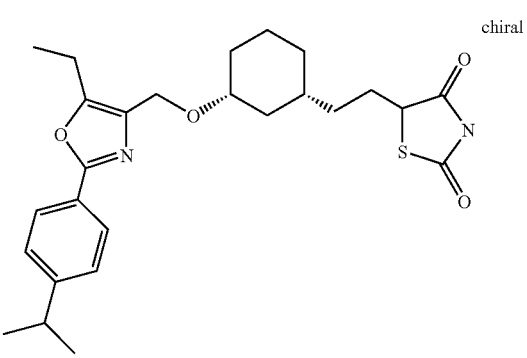

C26H34N2O4S (470.64), MS(ESI): 471 (M+H⁺).

EXAMPLE XLIX

The compound 5-{2-[cis-3-(5-methyl-2-p-tolyloxazol-4-ylmethoxy)cyclohexyl]ethyl}thiazolidine-2,4-dione from Example XXXIII was separated by chromatography on a chiral phase into the compounds 5-{2-[(1S,3S)-3-(5-methyl-2-p-tolyloxazol-4-ylmethoxy)cyclohexyl]ethyl}thiazolidine-2,4-dione and 5-{2-[(1R,3R)-3-(5-methyl-2-p-tolyloxazol-4-ylmethoxy)cyclohexyl]ethyl}thiazolidine-2,4-dione.

5-{2-[(1S,3S)-3-(5-methyl-2-p-tolyloxazol-4-yl-methoxy)cyclohexyl]ethyl}-thiazolidine-2,4-dione

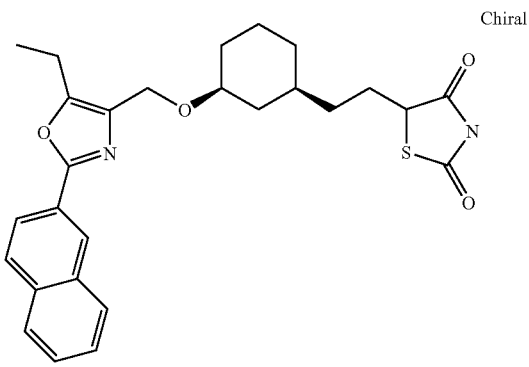

$C_{23}H_{28}N_2O_4S$ (428.55), MS(ESI): 429 (M+H$^+$).

5-{2-[(1R,3R)-3-(5-methyl-2-p-tolyloxazol-4-yl-methoxy)cyclohexyl]ethyl}-thiazolidine-2,4-dione

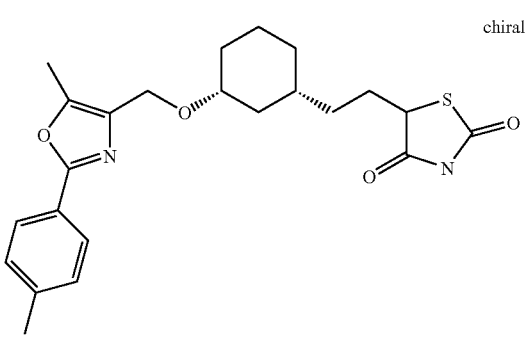

$C_{23}H_{28}N_2O_4S$ (428.55), MS(ESI): 429 (M+H$^+$).

EXAMPLE L 5-(2-{(1S,3S)-3-[2-(3,4-dimethylphenyl)-5-ethyloxazol-4-ylmethoxy]cyclohexyl}ethyl)thiazolidine-2,4-dione ((1S,3S)-3-allylcyclohexanol

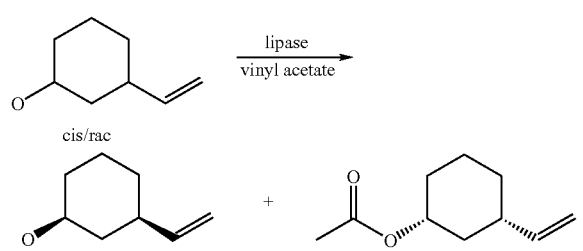

50 g of cis-3-allylcyclohexanol are dissolved in 200 ml vinyl acetate, and 3 g of lipase (Novozym) added. The mixture is stirred at RT until a conversion of 58% is reached (the conversion is monitored by GC). The enzyme is filtered off and the vinyl acetate is removed under reduced pressure. The resulting residue is purified chromatographically on silica gel. This gives 17 g of (1S, 3S)-3-allylcyclohexanol as a colorless oil.

C8H14O (126.20), Rf (n-heptane:ethyl acetate=1:1) =0.46.

5-(2-{(1S,3S)-3-[2-(3,4-dimethylphenyl)-5-ethyloxazol-4-ylmethoxy]cyclohexyl}ethyl)thiazolidine-2,4-dione Analogously to Example XXVIII and Example XXXI (1S,3S)-3-allylcyclohexanol, thiazolidinedione and 4-iodomethyl-5-ethyl-2-(3,4-dimethylphenyl)oxazol gave the compound 5-(2-{(1S,3S)-3-[2-(3,4-dimethylphenyl)-5-ethyloxazol-4-ylmethoxy]cyclohexyl}ethyl)thiazolidine-2,4-dione

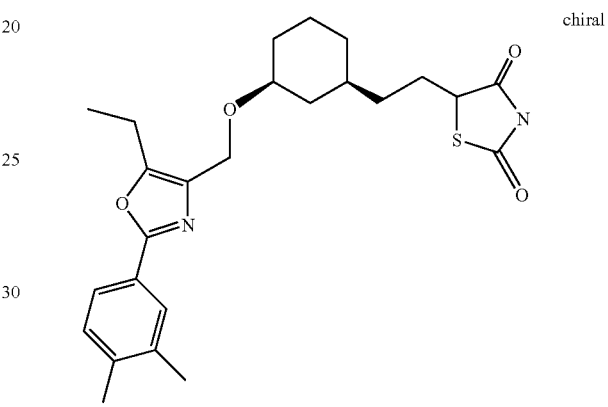

$C_{25}H_{32}N_2O_4S$ (456.61), MS(ESI): 457 (M+H$^+$).

EXAMPLE LI 5-(2-{(1S,3S)-3-[5-Ethyl-2-(4-trifluoromethylphenyl)oxazol-4-ylmethoxy]-cyclohexyl}ethyl)thiazolidine-2,4-dione Analogously to Example XXVIII and Example XXXI, (1S,3S)-3-allylcyclohexanol, thiazolidinedione and 4-iodomethyl-5-ethyl-2-(4-trifluoromethylphenyl)oxazole gave the compound 5-(2-{(1S,3S)-3-[5-ethyl-2-(4-trifluoromethylphenyl)oxazol-4-ylmethoxy]cyclohexyl}ethyl)thiazolidine-2,4-dione.

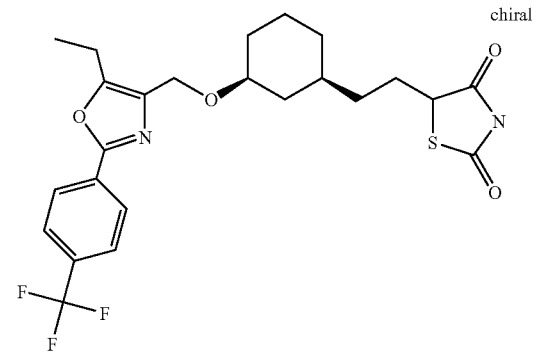

C24H27F3N2O4S (496.55), MS(ESI): 497 (M+H$^+$).

EXAMPLE LII

5-{2-[(1S,3S)-3-(5-Ethyl-2-naphthalen-2-yl-oxazol-4-ylmethoxy)cyclohexyl]ethyl}-thiazolidine-2,4-dione Analogously to Example XXVIII and Example XXXI (1S,3S)-3-allyl-cyclohexanol, thiazolidinedione and 5-ethyl-4-iodomethyl-2-naphthalen-2-yloxazole gave the compound 5-{2-[(1S,3S)-3-(5-ethyl-2-naphthalen-2-yloxazol-4-ylmethoxy)cyclohexyl]ethyl}thiazolidine-2,4-dione.

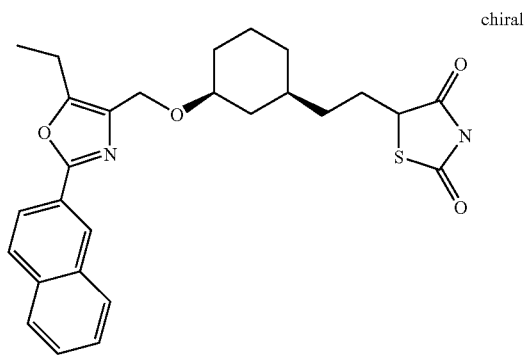

C27H30N2O4S (478.62), MS(ESI): 479 (M+H+).

EXAMPLE LIII 5-(2-{(1S,3S)-3-[5-Ethyl-2-(3-trifluoromethylphenyl)oxazol-4-ylmethoxy]-cyclohexyl}ethyl)thiazolidine-2,4-dione Analogously to Example XXVIII and Example XXXI (1S,3S)-3-allylcyclohexanol, thiazolidinedione and 4-iodomethyl-5-ethyl-2-(3-trifluoromethylphenyl)oxazole gave the compound 5-(2-{(1S,3S)-3-[5-ethyl-2-(3-trifluoromethylphenyl)-oxazol-4-ylmethoxy]cyclohexyl}ethyl)thiazolidine-2,4-dione.

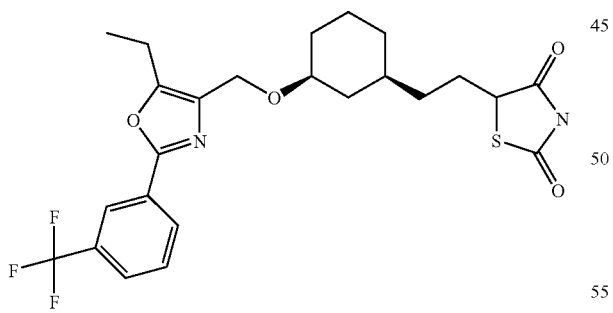

C24H27F3N2O4S (496.55), MS(ESI): 497 (M+H+).

BEISPIEL LIV 5-(2-{(1S,3S)-3-[5-Ethyl-2-(4-tert-butylphenyl)oxazol-4-ylmethoxy]cyclohexyl}-ethyl)thiazolidine-2,4-dione Analogously to Example XXVIII and Example XXXI (1S,3S)-3-allylcyclohexanol, thiazolidinedione and 4-iodomethyl-5-ethyl-2-(4-tert-butylphenyl)oxazole gave the compound 5-(2-{(1S,3S)-3-[5-ethyl-2-(4-tert-butylphenyl)oxazol-4-ylmethoxy]cyclohexyl}ethyl)thiazolidine-2,4-dione.

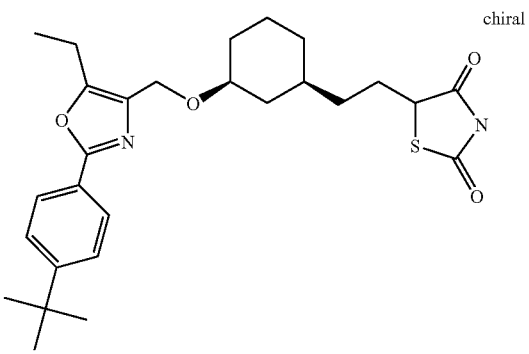

C27H36N2O4S (484.66), MS(ESI): 485 (M+H+).

EXAMPLE LV 5-(2-{(1S,3S)-3-[5-Isopropyl-2-(3,4-dimethylphenyl)oxazol-4-ylmethoxy]-cyclohexyl}ethyl)thiazolidine-2,4-dione Analogously to Example XXVIII and Example XXXI (1S,3S)-3-allylcyclohexanol, thiazolidinedione and 4-iodomethyl-5-isopropyl-2-(3,4-dimethylphenyl)oxazole gave the compound 5-(2-{(1S,3S)-3-[5-isopropyl-2-(3,4-dimethylphenyl)oxazol-4-ylmethoxy]cyclohexyl}ethyl)thiazolidine-2,4-dione.

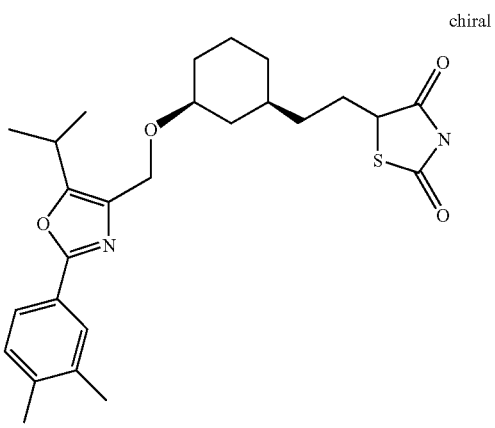

C26H34N2O4S (470.64), MS(ESI): 471 (M+H+).

EXAMPLE LVI 5-(2-{(1S,3S)-3-[5-Ethyl-2-(4-isobutylphenyl)oxazol-4-ylmethoxy]cyclohexyl}ethyl)-thiazolidine-2,4-dione Analogously to Example XXVIII and Example XXXI (1S,3S)-3-allylcyclohexanol, thiazolidinedione and 4-iodomethyl-5-ethyl-2-(4-isobutylphenyl)oxazole gave the compound 5-(2-{(1S,3S)-3-[5-ethyl-2-(4-isobutylphenyl)oxazol-4-ylmethoxy]cyclohexyl}ethyl)thiazolidin-2,4-dione.

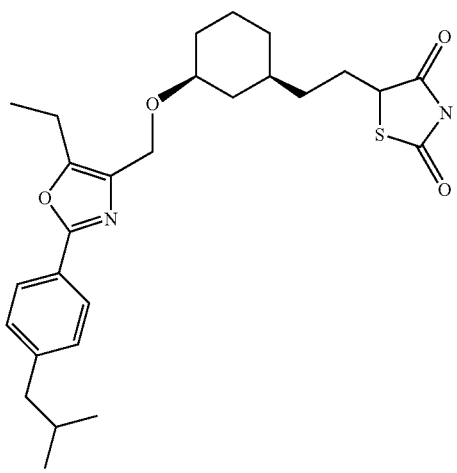

C27H36N2O4S (484.66), MS(ESI): 485 (M+H⁺).

EXAMPLE LVII 5-(2-{(1S,3S)-3-[5-Isopropyl-2-(3-trifluoromethylphenyl)oxazol-4-ylmethoxy]-cyclohexyl}ethyl)thiazolidine-2,4-dione Analogously to Example XXVIII and Example XXXI (1S,3S)-3-allylcyclohexanol, thiazolidinedione and 4-iodomethyl-5-isopropyl-2-(3-trifluormethylphenyl)oxazole gave the compound 5-(2-{(1S,3S)-3-[5-isopropyl-2-(3-trifluoromethylphenyl)oxazol-4-ylmethoxy]cyclohexyl}ethyl)thiazolidine-2,4-dione.

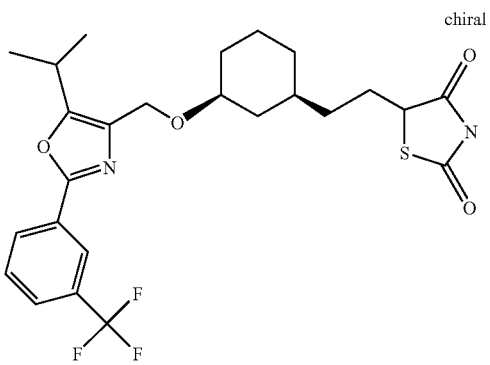

C25H29F3N2O4S (510.58), MS(ESI): 511 (M+H⁺).

EXAMPLE LVIII 5-(2-{(1S,3S)-3-[5-Isopropyl-2-(4-tert-butylphenyl)oxazol-4-ylmethoxy]cyclohexyl}-ethyl)thiazolidine-2,4-dione Analogously to Example XXVIII and Example XXXI (1S,3S)-3-allylcyclohexanol, thiazolidinedione and 4-iodomethyl-5-isopropyl-2-(4-tert-butylphenyl)oxazol gave the following compound 5-(2-{(1S,3S)-3-[5-isopropyl-2-(4-tert-butylphenyl)oxazol-4-ylmethoxy]cyclohexyl}ethyl)thiazolidine-2,4-dione.

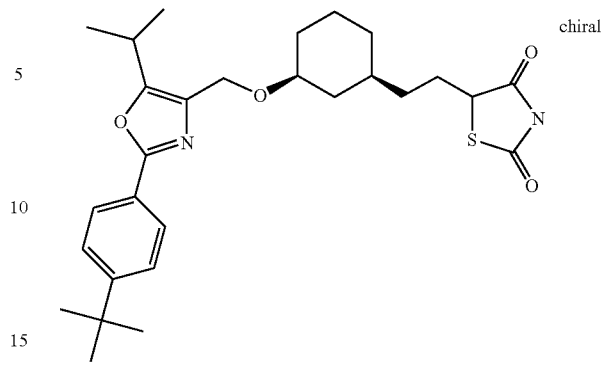

C28H38N2O4S (498.69), MS(ESI): 499 (M+H⁺).

EXAMPLE LIX 5-(2-{(1S,3S)-3-[5-Isopropyl-2-(4-isobutylphenyl)oxazol-4-ylmethoxy]cyclohexyl}-ethyl)thiazolidine-2,4-dione Analogously to Example XXVIII and Example XXXI (1S,3S)-3-allylcyclohexanol, thiazolidinedione and 4-iodomethyl-5-isopropyl-2-(4-isobutylphenyl)oxazole gave the compound 5-(2-{(1S,3S)-3-[5-isopropyl-2-(4-isobutylphenyl)oxazol-4-ylmethoxy]cyclohexyl}ethyl)thiazolidine-2,4-dione.

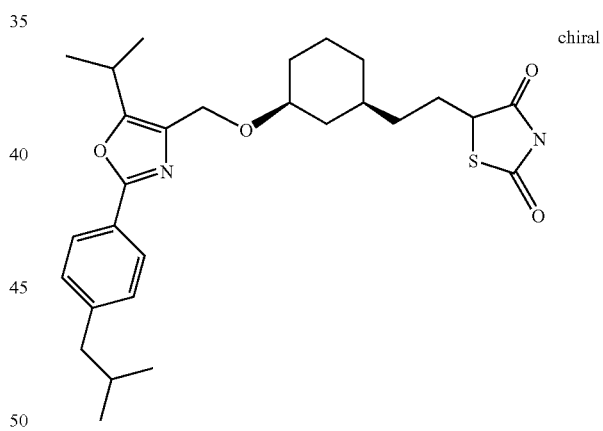

C28H38N2O4S (498.69), MS(ESI): 499 (M+H⁺).

EXAMPLE LX 5-(2-{(1S,3S)-3-[5-Isopropyl-2-(4-trifluoromethylphenyl)oxazol-4-ylmethoxy]-cyclohexyl}ethyl)thiazolidine-2,4-dione Analogously to Example XXVIII and Example XXXI (1S,3S)-3-allylcyclohexanol, thiazolidinedione and 4-iodomethyl-5-isopropyl-2-(4-trifluoromethylphenyl)oxazole gave the compound 5-(2-{(1S,3S)-3-[5-isopropyl-2-(4-trifluoromethylphenyl)oxazol-4-ylmethoxy]cyclohexyl}ethyl)thiazolidine-2,4-dione.

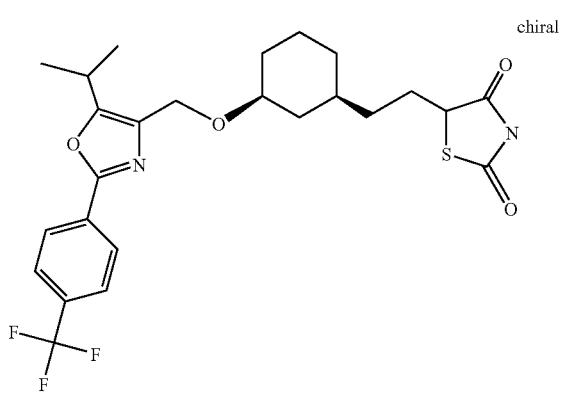

C25H29F3N2O4S (510.58), MS(ESI): 511 (M+H⁺).

EXAMPLE LXI

5-{2-[(1S,3S)-3-(5-Isopropyl-2-naphthalen-2-yloxazol-4-ylmethoxy)cyclohexyl]-ethyl}thiazolidine-2,4-dione Analogously to Example XXVIII and Example XXXI (1S,3S)-3-allylcyclohexanol, thiazolidinedione and 5-isopropyl-4-iodomethyl-2-naphthalen-2-yloxazole gave the compound 5-{2-[(1S,3S)-3-(5-isopropyl-2-naphthalen-2-yloxazol-4-ylmethoxy)cyclohexyl]ethyl}thiazolidine-2,4-dione.

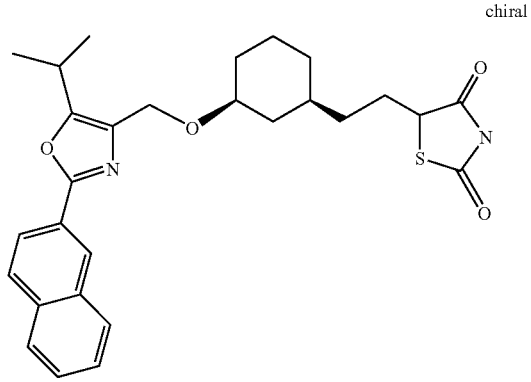

C28H32N2O4S (492.64), MS(ESI): 493 (M+H⁺).

EXAMPLE LXII 5-(2-{cis-3-[2-(3-Methoxyphenyl)-5-methyloxazol-4-ylmethoxy]cyclohexyl}ethyl)-3-methylthiazolidine-2,4-dione Analogously to Example XXVIII and Example XXXI cis-3-allylcyclohexanol, 3-methylthiazolidinedione and 4-iodomethyl-5-methyl-2-(3-methoxyphenyl)oxazole gave the compound 5-(2-{cis-3-[2-(3-methoxyphenyl)-5-methyloxazol-4-ylmethoxy]cyclohexyl}ethyl)-3-methylthiazolidine-2,4-dione.

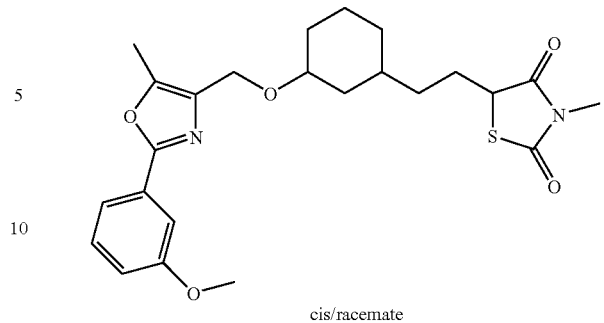

C24H30N2O5S (458.58), MS(ESI): 459 (M+H⁺).

BEISPIEL LXIII 5-(2-{cis-3-[2-(3-Methoxyphenyl)-5-methyloxazol-4-ylmethoxy]cyclohexyl}ethyl)-3-phenylthiazolidine-2,4-dione Analogously to Example XXVIII and Example XXXI cis-3-allylcyclohexanol, 3-phenylthiazolidinedione and 4-iodomethyl-5-methyl-2-(3-methoxyphenyl)oxazole gave the compound 5-(2-{cis-3-[2-(3-methoxyphenyl)-5-methyloxazol-4-ylmethoxy]cyclohexyl}ethyl)-3-phenylthiazolidine-2,4-dione.

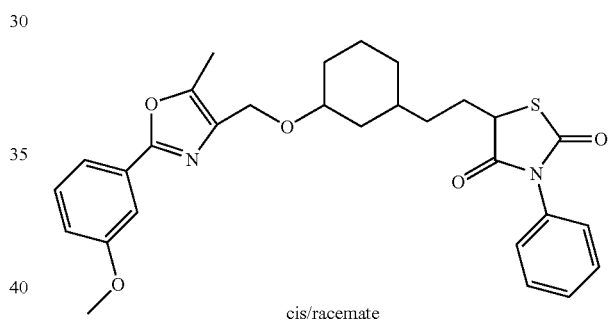

C29H32N2O5S (520.65), MS(ESI): 521 (M+H⁺).

EXAMPLE LXIV 5-(2-{cis-3-[2-(4-Methylphenyl)-5-methyloxazol-4-ylmethoxy]cyclohexyl}ethyl)-3-methylthiazolidine-2,4-dione Analogously to Example XXVIII and Example XXXI cis-3-allylcyclohexanol, 3-methylthiazolidinedione and 4-iodomethyl-5-methyl-2-(4-methylphenyl)oxazole gave the compound 5-(2-{cis-3-[2-(4-methylphenyl)-5-methyloxazol-4-ylmethoxy]cyclohexyl}ethyl)-3-methylthiazolidine-2,4-dione.

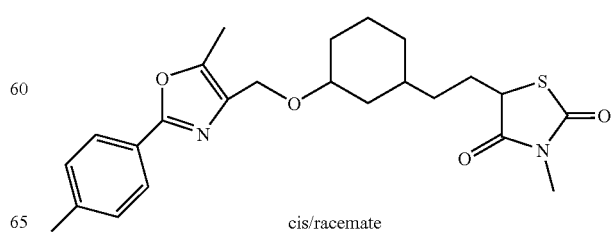

C24H30N2O4S (442.58), MS(ESI): 443 (M+H⁺).

EXAMPLE LXV 5-(2-{cis-3-[2-(4-Methylphenyl)-5-methyloxazol-4-ylmethoxy]cyclohexyl}ethyl)-3-benzylthiazolidine-2,4-dione Analogously to Example XXVIII and Example XXXI cis-3-allylcyclohexanol, 3-benzylthiazolidinedione and 4-iodomethyl-5-methyl-2-(4-methylphenyl)oxazole gave the compound 5-(2-{cis-3-[2-(4-methylphenyl)-5-methyloxazol-4-ylmethoxy]cyclohexyl}ethyl)-3-benzylthiazolidine-2,4-dione.

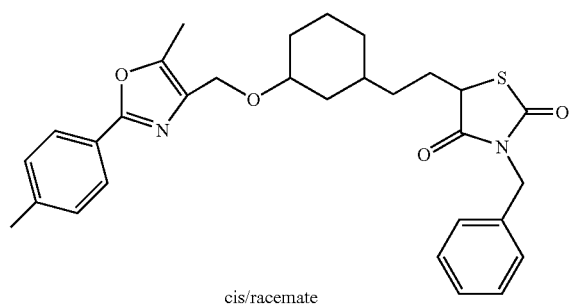

cis/racemate

C30H34N2O4S (518.58), MS(ESI): 519 (M+H$^+$).

EXAMPLE LXVI 5-(2-{cis-3-[2-(3-Methoxyphenyl)-5-isopropyloxazol-4-ylmethoxy]cyclohexyl}ethyl)-3-methylthiazolidine-2,4-dione Analogously to Example XXVIII and Example XXXI cis-3-allylcyclohexanol, 3-methylthiazolidinedione and 4-iodomethyl-5-isopropyl-2-(3-methoxyphenyl)-oxazole gave the compound 5-(2-{cis-3-[2-(3-methoxyphenyl)-5-isopropyloxazol-4-ylmethoxy]cyclohexyl}ethyl)-3-methylthiazolidine-2,4-dione.

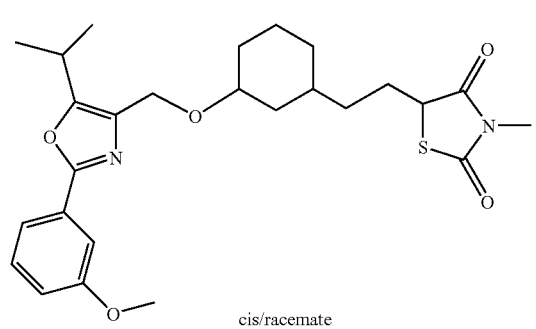

cis/racemate

C26H34N2O5S (486.64), MS(ESI): 487 (M+H$^+$).

EXAMPLE LXVII 5-(2-{cis-3-[2-(3-Methoxyphenyl)-5-phenyloxazol-4-ylmethoxy]cyclohexyl}ethyl)-3-methylthiazolidine-2,4-dione Analogously to Example XXVIII and Example XXXI cis-3-allylcyclohexanol, 3-methylthiazolidinedione and 4-iodomethyl-5-phenyl-2-(3-methoxyphenyl)oxazole gave the compound 5-(2-{cis-3-[2-(3-methoxyphenyl)-5-phenyloxazol-4-ylmethoxy]cyclohexyl}ethyl)-3-methylthiazolidine-2,4-dione.

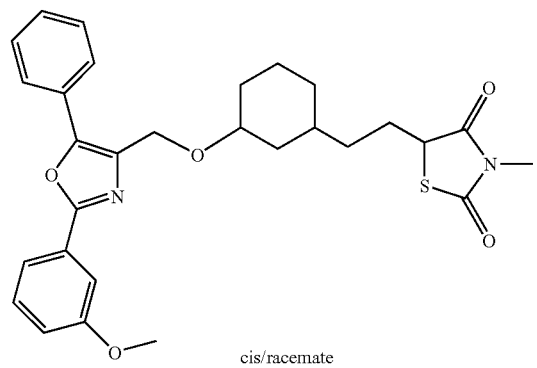

cis/racemate

C29H32N2O5S (520.65), MS(ESI): 521 (M+H$^+$).

EXAMPLE LXVIII 5-(2-{cis-3-[2-(3-Methoxyphenyl)-5-phenyloxazol-4-ylmethoxy]cyclohexyl}ethyl)-3-phenylthiazolidine-2,4-dione Analogously to Example XXVIII and Example XXXI cis-3-allylcyclohexanol, 3-phenylthiazolidinedione and 4-iodomethyl-5-phenyl-2-(3-methoxyphenyl)oxazole gave the compound 5-(2-{cis-3-[2-(3-methoxyphenyl)-5-phenyloxazol-4-ylmethoxy]cyclohexyl}ethyl)-3-phenylthiazolidine-2,4-dione.

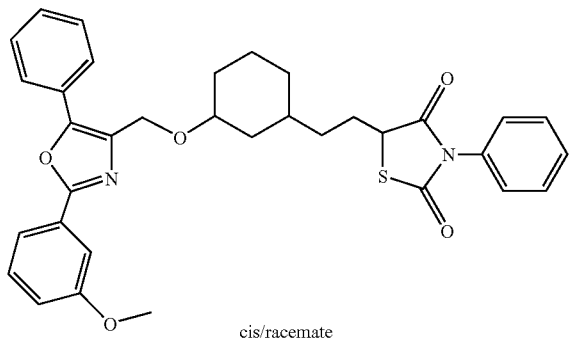

cis/racemate

C34H34N2O5S (582.72), MS(ESI): 583 (M+H$^+$).

We claim:

1. A compound of the formula I

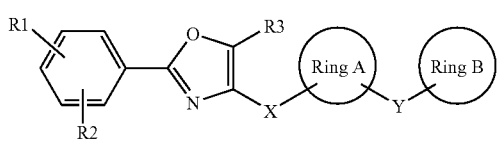

I wherein

Ring A is ($C_6$)-cycloalkanediyl $R_1$, $R_2$ are each independently H, F, Br, $CF_3$, $OCF_3$, ($C_1$–$C_6$)-alkyl, O—($C_1$–$C_6$)-alkyl, $SCF_3$, $SF_5$, $OCF_2$—$CHF_2$, O-phenyl, OH, or $NO_2$; or $R_1$ and $R_2$, taken together with the carbon atoms of the phenyl ring to which they are attached, form a fused, unsaturated or completely or partially saturated bicyclic ($C_9$–$C_{12}$)-aryl;

R3 is H, $CF_3$, ($C_1$–$C_6$)-alkyl, ($C_1$–$C_6$)-alkoxy, ($C_3$–$C_8$)-cycloalkyl or phenyl;

X is ($C_1$–$C_6$)-alkanediyl, wherein one or more carbon atoms therein is optionally replaced by an oxygen atom;

Y is ($C_1$–$C_6$)-alkanediyl or ($C_1$–$C_6$)-alkenediyl, wherein one or more carbon atoms therein is optionally replaced by O, CO, S, SO or $SO_2$, and wherein said ($C_1$–$C_6$)-alkanediyl and ($C_1$–$C_6$)-alkenediyl groups are optionally substituted by OH;

Ring B is a group selected from (a), (b) or (c):

(a) phenyl optionally mono- or disubstituted by $NO_2$, Cl, CN, ($C_1$–$C_6$)-alkyl or ($C_1$–$C_6$)-alkoxy (b) tetrazole (c) pyrrolidin-2-one wherein the pyrrolidinyl ring of said pyrrolidin-2-one group contains an additional nitrogen atom or a sulfur atom and is substituted by oxo or thioxo, and is optionally substituted on a nitrogen atom therein by R4;

R4 is ($C_1$–$C_6$)-alkyl, phenyl or benzyl;

and pharmaceutically acceptable salts thereof.

2. The compound of claim 1 wherein:

Ring A is ($C_6$)-cycloalkanediyl;

R1, R2 are each independently H, F, Br, $CF_3$, $OCF_3$, ($C_1$–$C_6$)-alkyl, O—($C_1$–$C_6$)-alkyl, $SCF_3$, SF5, OCF2—CHF2, O-phenyl, OH or NO2; or $R_1$ and $R_2$, taken together with the carbon atoms of the phenyl ring to which they are attached, form a fused, unsaturated or completely or partially saturated bicyclic ($C_9$–$C_{12}$)-aryl;

R3 is H, $CF_3$, ($C_1$–$C_6$)-alkyl, ($C_3$–$C_8$)-cycloalkyl or phenyl;

X is ($C_1$–$C_6$)-alkanediyl, wherein one carbon atom therein is optionally replaced by an oxygen atom;

Y is ($C_1$–$C_6$)-alkanediyl or ($C_1$–$C_6$)-alkenediyl, wherein one or two carbon atoms of said ($C_1$–$C_6$)-alkanediyl and ($C_1$–$C_6$)-alkenediyl groups are optionally replaced by O, CO, S, SO or $SO_2$, and wherein said ($C_1$–$C_6$)-alkanediyl and ($C_1$–$C_6$)-alkenediyl groups are optionally substituted by OH;

Ring B is a group selected from (a), (b) or (c):

(a) phenyl optionally mono- or disubstituted by $NO_2$, Cl, CN, ($C_1$–$C_6$)-alkyl or ($C_1$–$C_6$)-alkoxy (b) tetrazole (c) pyrrolidin-2-one wherein the pyrrolidinyl ring of said pyrrolidin-2-one group contains an additional nitrogen atom or a sulfur atom in the 4-position and is substituted by oxo or thioxo in the 5-position, and is optionally substituted on the nitrogen atom in the 1-position by R4;

R4 is ($C_1$–$C_6$)-alkyl, phenyl or benzyl;

and pharmaceutically acceptable salts thereof.

3. The compound of claim 2 wherein:

Ring A is ($C_6$)-cycloalkanediyl;

$R_1$, $R_2$ are each independently H, F, Br, $CF_3$, $OCF_3$, ($C_1$–$C_6$)-alkyl, O—($C_1$–$C_6$)-alkyl, $SCF_3$, $SF_5$, $OCF_2$—$CHF_2$, O-phenyl, OH or $NO_2$; or R₁ and R₂, taken together with the carbon atoms of the phenyl ring to which they are attached, form a fused, unsaturated or completely or partially saturated bicyclic ($C_9$–$C_{12}$)-aryl ;

R3 is H, $CF_3$, ($C_1$–$C_6$)-alkyl, ($C_3$–$C_8$)-cycloalkyl or phenyl;

X is ($C_1$–$C_6$)-alkanediyl, wherein the carbon atom in the 1-position is replaced by an oxygen atom;

Y is ($C_1$–$C_6$)-alkanediyl or ($C_1$–$C_6$)-alkenediyl, wherein one or two carbon atoms of said ($C_1$–$C_6$)-alkanediyl and ($C_1$–$C_6$)-alkenediyl groups are optionally replaced by O, CO or $SO_2$, and wherein said ($C_1$–$C_6$)-alkanediyl and ($C_1$–$C_6$)-alkenediyl groups are optionally substituted by OH;

Ring B is a group selected from (a), (b) or (c):
(a) phenyl optionally mono- or disubstituted by $NO_2$, $Cl$, $CN$, ($C_1$–$C_6$)-alkyl or ($C_1$–$C_6$)-alkoxy
(b) tetrazole
(c) pyrrolidin-2-one wherein the pyrrolidinyl ring of said pyrrolidin-2-one group contains an additional nitrogen atom or a sulfur atom in the 4-position and is substituted by oxo or thioxo in the 5-position, and is optionally substituted on the nitrogen atom in the 1-position by R4;

R4 is ($C_1$–$C_6$)-alkyl, phenyl or benzyl;
and pharmaceutically acceptable salts thereof.

4. The compound of claim 3 wherein:
Ring A is cyclohexane-1,3-diyl;
R₁, R₂ are each independently H, F, Br, $CF_3$, $OCF_3$, ($C_1$–$C_6$)-alkyl, O—($C_1$–$C_6$)-alkyl, $SCF_3$, $SF_5$, $OCF_2$—$CHF_2$, O-phenyl, OH or $NO_2$; or
R1 and R2, taken together with the carbon atoms of the phenyl ring to which they are attached, form a fused, unsaturated bicyclic ($C_9$–$C_{10}$)-aryl;

R3 is H, $CF_3$, ($C_1$–$C_6$)-alkyl, ($C_3$–$C_6$)-cycloalkyl or phenyl;

X is $CH_2$—O;

Y is ($C_1$–$C_4$)-alkanediyl, O—($C_1$–$C_4$)-alkenediyl, ($C_1$–$C_4$)-alkenediyl, O—($C_1$–$C_4$)-alkenediyl, O—$SO_2$ or O—CO, wherein said ($C_1$–$C_4$)-alkanediyl group is optionally substituted by OH;

Ring B is a group selected from (a), (b) or (c):
(a) phenyl optionally mono- or disubstituted by $NO_2$, $Cl$, $CN$, ($C_1$–$C_6$)-alkyl or ($C_1$–$C_6$)-alkoxy
(b) tetrazole
(c) thiazolidin-1,4-dione optionally substituted by R4 on the nitrogen in the 3-position-atom;

R4 is ($C_1$–$C_6$)-alkyl, phenyl or benzyl;
and pharmaceutically acceptable salts thereof.

5. The compound of claim 4 wherein:
Ring A is cyclohexane-1,3-diyl;
R₁, R₂ are each independently H, F, Br, $CF_3$, ($C_1$–$C_6$)-alkyl or O—($C_1$–$C_6$)-alkyl; or
R₁ and R₂, taken together with the carbon atoms of the phenyl ring to which they are attached, form naphthyl;

R3 is ($C_1$–$C_6$)-alkyl, ($C_5$–$C_6$)-cycloalkyl or phenyl;

X is $CH_2$—O;

Y is ($C_1$–$C_4$)-alkanediyl, O—($C_1$–$C_4$)-alkanediyl, ($C_1$–$C_4$)-alkenediyl, O—($C_1$–$C_4$)-alkenediyl, O—$SO_2$ or O—CO, where said ($C_1$–$C_4$)-alkanediyl group is optionally substituted by OH;

Ring B is a group selected from (a), (b) or (c):
(a) phenyl optionally mono- or disubstituted by $NO_2$, $Cl$, $CN$, ($C_1$–$C_6$)-alkyl or ($C_1$–$C_6$)-alkoxy
(b) tetrazole
(c) thiazolidin-2,4-dione optionally substituted by R4 on the nitrogen in the 3-position;

R4 is ($C_1$–$C_6$)-alkyl, phenyl or benzyl;
and pharmaceutically acceptable salts thereof.

6. The compound of claim 5 wherein:
R2 is hydrogen; and
R1 is attached to the carbon of the phenyl ring that is meta- or para- to the carbon by which the phenyl ring is attached to the oxazole ring.

7. The compound of claim 6 wherein:
Y is —$CH_2$—$CH_2$—.

8. A pharmaceutical composition comprising a pharmaceutically acceptable carrier and one or more compounds of claim 1.

9. The pharmaceutical composition of claim 8 further comprising at least one additional active ingredient.

10. The pharmaceutical composition of claim 9 wherein said additional active ingredient is an antidiabetic.

11. The pharmaceutical composition of claim 9 wherein said additional active ingredient is a lipid modulator.

12. A method of treating diabetes mellitus including the prevention of the squelae associated therewith comprising administering to a patient in need thereof a therapeutically effective amount of a compound of claim 1.

13. A method of treating dyslipidemia and squelae associated therewith comprising administering to a patient in need thereof a therapeutically effective amount of a compound of claim 1.

* * * * *